US012171873B2

(12) United States Patent
Lay et al.

(10) Patent No.: US 12,171,873 B2
(45) Date of Patent: *Dec. 24, 2024

(54) DEVICES AND METHODS FOR DELIVERY OF SUBSTANCES TO ANIMALS

(71) Applicant: Ruminant Biotech Corp Limited, Hamilton (NZ)

(72) Inventors: Mark Christopher Lay, Hamilton (NZ); Hayden Peter Thomas, Hamilton (NZ); Neil Richard Gladden, Hamilton (NZ); David Leslie Hayman, Hamilton (NZ); Geoffrey Earle Corbett, Hamilton (NZ); Prabhat Bhusal, Hamilton (NZ)

(73) Assignee: Ruminant Biotech Corp Limited, Hamilton (NZ)

(*) Notice: Subject to any disclaimer, the term of this patent is extended or adjusted under 35 U.S.C. 154(b) by 7 days.

This patent is subject to a terminal disclaimer.

(21) Appl. No.: 17/987,983

(22) Filed: Nov. 16, 2022

(65) Prior Publication Data

US 2023/0083835 A1 Mar. 16, 2023

Related U.S. Application Data

(63) Continuation of application No. 17/544,445, filed on Dec. 7, 2021, now Pat. No. 11,529,310.

(30) Foreign Application Priority Data

Dec. 8, 2020 (NZ) .......................................... 770786
Mar. 30, 2021 (AU) .................................. 2021900932
Aug. 25, 2021 (AU) .................................. 2021221810

(51) Int. Cl.
*A61K 33/00* (2006.01)
*A61K 9/00* (2006.01)
(Continued)

(52) U.S. Cl.
CPC ............ *A61K 9/0068* (2013.01); *A61K 33/00* (2013.01); *A61K 47/34* (2013.01); *A61K 47/44* (2013.01)

(58) Field of Classification Search
CPC ...... A61K 9/0068; A61K 33/00; A61K 47/34; A61K 47/44; A61K 9/4808; A61K 9/4875; A61K 31/02; Y02P 60/22
See application file for complete search history.

(56) References Cited

U.S. PATENT DOCUMENTS 3,660,562 A 5/1972 Grass et al.
4,251,506 A 2/1981 Laby
(Continued)

FOREIGN PATENT DOCUMENTS

AU 4230972 A 11/1973
AU 498884 B2 3/1979
(Continued)

OTHER PUBLICATIONS

Machado et al. (Microb Ecol 2018;75:811-818) (Year: 2018).*
(Continued)

*Primary Examiner* — Ernst V Arnold
(74) *Attorney, Agent, or Firm* — Fish & Richardson P.C.

(57) ABSTRACT

The invention provides a delayed release dosage form and a bolus configured for administration to an animal, wherein the dosage form and the bolus is configured to release a hydrophobic substance to the animal over a period of time. Preferably the hydrophobic substance is a haloform. Also provided is the use of the delayed release dosage form or bolus of the invention to reduce methane production in a ruminant animal. Also provided is the method of manufacturing a bolus of the invention.

46 Claims, 21 Drawing Sheets

(51) Int. Cl.
  *A61K 47/34*  (2017.01)
  *A61K 47/44*  (2017.01)

(56) References Cited

U.S. PATENT DOCUMENTS

| | | | |
|---|---|---|---|
| 4,416,659 A | 11/1983 | Simpson et al. | |
| 4,955,881 A * | 9/1990 | Eckenhoff | A61M 31/002 |
| | | | 604/890.1 |
| 5,074,857 A | 12/1991 | Shepherd et al. | |
| 5,807,594 A * | 9/1998 | King | A23K 40/35 |
| | | | 424/490 |
| 5,985,314 A | 11/1999 | Porter | |
| 6,391,331 B1 | 5/2002 | Allen et al. | |
| 6,689,376 B2 | 2/2004 | Allen et al. | |
| 6,764,691 B2 | 7/2004 | Allen et al. | |
| 7,354,870 B2 * | 4/2008 | Luan | B33Y 10/00 |
| | | | 438/750 |
| 8,771,723 B2 | 7/2014 | Perdok et al. | |
| 8,784,871 B2 | 7/2014 | Duval et al. | |
| 8,993,009 B2 | 3/2015 | Smith | |
| 9,266,814 B2 | 2/2016 | Duval et al. | |
| 9,358,218 B2 | 6/2016 | Vuorenmaa et al. | |
| 9,365,489 B2 | 6/2016 | Duval et al. | |
| 9,902,685 B2 | 2/2018 | Duval et al. | |
| 9,980,995 B2 | 5/2018 | Machado et al. | |
| 9,993,507 B2 | 6/2018 | Embree et al. | |
| 10,154,981 B2 | 12/2018 | Duval et al. | |
| 10,159,265 B2 | 12/2018 | Teres et al. | |
| 10,272,123 B2 | 4/2019 | Smith | |
| 10,293,006 B2 | 5/2019 | Embree et al. | |
| 10,398,154 B2 | 9/2019 | Embree et al. | |
| 10,440,975 B2 | 10/2019 | Park et al. | |
| 10,448,658 B2 | 10/2019 | Embree et al. | |
| 11,529,310 B2 * | 12/2022 | Lay | A61K 9/0068 |
| 12,115,248 B2 * | 10/2024 | Lay | A61K 47/44 |
| 2002/0037317 A1 | 3/2002 | Porter | |
| 2012/0225841 A1 | 9/2012 | Lowe et al. | |
| 2016/0339067 A1* | 11/2016 | Machado | A23K 50/10 |
| 2018/0271922 A1 | 9/2018 | Machado et al. | |
| 2018/0310592 A1 | 11/2018 | Embree et al. | |
| 2019/0174793 A1 | 6/2019 | Tomkins et al. | |
| 2020/0121730 A1 | 4/2020 | Mitteness | |
| 2020/0123588 A1 | 4/2020 | Mizrahi | |
| 2020/0138056 A1 | 5/2020 | Graz et al. | |
| 2020/0170281 A1 | 6/2020 | Graz et al. | |
| 2020/0229465 A1 | 7/2020 | Duval et al. | |
| 2021/0128479 A1 | 5/2021 | Cheng et al. | |
| 2022/0175670 A1 | 6/2022 | Lay et al. | |
| 2023/0085030 A1 | 3/2023 | Lay et al. | |

FOREIGN PATENT DOCUMENTS

| | | |
|---|---|---|
| AU | 6216480 A | 3/1981 |
| AU | 6216780 A | 3/1981 |
| AU | 515739 B2 | 4/1981 |
| AU | 517490 B2 | 8/1981 |
| AU | 7100281 A | 12/1981 |
| AU | 520409 B2 | 1/1982 |
| AU | 7778281 A | 3/1982 |
| AU | 7958282 A | 7/1982 |
| AU | 529027 B2 | 5/1983 |
| AU | 9010882 A | 5/1983 |
| AU | 1304383 A | 10/1983 |
| AU | 1671283 A | 1/1984 |
| AU | 535573 B1 | 3/1984 |
| AU | 2823284 A | 11/1984 |
| AU | 2964984 A | 12/1984 |
| AU | 3728185 A | 7/1985 |
| AU | 4312385 A | 12/1985 |
| AU | 548834 B2 | 1/1986 |
| AU | 549557 B2 | 1/1986 |
| AU | 552361 B2 | 5/1986 |
| AU | 555998 B2 | 10/1986 |
| AU | 5848386 A | 12/1986 |
| AU | 558009 | 1/1987 |
| AU | 6088086 A | 2/1987 |
| AU | 6102086 A | 2/1987 |
| AU | 6113686 A | 2/1987 |
| AU | 559938 B2 | 3/1987 |
| AU | 6479186 A | 5/1987 |
| AU | 564372 B2 | 8/1987 |
| AU | 6829787 A | 8/1987 |
| AU | 6886987 A | 8/1987 |
| AU | 6981987 A | 9/1987 |
| AU | 566109 B2 | 10/1987 |
| AU | 7050587 A | 10/1987 |
| AU | 7063687 A | 10/1987 |
| AU | 7171887 A | 10/1987 |
| AU | 567968 B2 | 12/1987 |
| AU | 569335 B2 | 1/1988 |
| AU | 7442787 A | 1/1988 |
| AU | 571922 B2 | 4/1988 |
| AU | 577096 B2 | 9/1988 |
| AU | 579320 B2 | 11/1988 |
| AU | 580782 B2 | 2/1989 |
| AU | 581021 B2 | 2/1989 |
| AU | 585044 B2 | 6/1989 |
| AU | 2681088 A | 6/1989 |
| AU | 2691388 A | 6/1989 |
| AU | 2377288 A | 7/1989 |
| AU | 2937989 A | 8/1989 |
| AU | 588828 B2 | 9/1989 |
| AU | 3107089 A | 9/1989 |
| AU | 595033 B2 | 3/1990 |
| AU | 4614589 A | 6/1990 |
| AU | 598938 B2 | 7/1990 |
| AU | 5052290 A | 9/1990 |
| AU | 5124790 A | 9/1990 |
| AU | 602818 B2 | 10/1990 |
| AU | 5079290 A | 10/1990 |
| AU | 5374090 A | 10/1990 |
| AU | 5426990 A | 11/1990 |
| AU | 5523490 A | 11/1990 |
| AU | 605482 B2 | 1/1991 |
| AU | 5880290 A | 1/1991 |
| AU | 5912190 A | 1/1991 |
| AU | 6486390 A | 4/1991 |
| AU | 609995 B2 | 5/1991 |
| AU | 611060 B2 | 5/1991 |
| AU | 613039 B2 | 7/1991 |
| AU | 7156991 A | 8/1991 |
| AU | 615599 B2 | 10/1991 |
| AU | 7208791 A | 10/1991 |
| AU | 7581391 A | 10/1991 |
| AU | 618589 B2 | 1/1992 |
| AU | 619454 B2 | 1/1992 |
| AU | 623335 B2 | 5/1992 |
| AU | 627845 B2 | 9/1992 |
| AU | 633617 B2 | 2/1993 |
| AU | 633741 B2 | 2/1993 |
| AU | 633926 B2 | 2/1993 |
| AU | 2420092 A | 3/1993 |
| AU | 636478 B2 | 4/1993 |
| AU | 637043 B2 | 5/1993 |
| AU | 643219 B2 | 11/1993 |
| AU | 3739993 A | 11/1993 |
| AU | 644231 B2 | 12/1993 |
| AU | 644462 B2 | 12/1993 |
| AU | 645518 B2 | 1/1994 |
| AU | 653425 B2 | 9/1994 |
| AU | 7652394 A | 4/1995 |
| AU | 659220 B2 | 5/1995 |
| AU | 660442 B2 | 6/1995 |
| AU | 661345 B2 | 7/1995 |
| AU | 665844 B2 | 1/1996 |
| AU | 666394 B2 | 2/1996 |
| AU | 666674 B2 | 2/1996 |
| AU | 669435 B2 | 6/1996 |
| AU | 672520 B2 | 10/1996 |
| AU | 682150 B2 | 9/1997 |
| AU | 682764 B2 | 10/1997 |
| AU | 682827 B2 | 10/1997 |
| AU | 687062 B2 | 2/1998 |
| AU | 690188 B2 | 4/1998 |

(56) References Cited

FOREIGN PATENT DOCUMENTS

| | | |
|---|---|---|
| AU | 691313 B2 | 5/1998 |
| AU | 693302 B2 | 6/1998 |
| AU | 1277497 A | 6/1998 |
| AU | 697144 B2 | 10/1998 |
| AU | 6065498 A | 10/1998 |
| AU | 6577998 A | 11/1998 |
| AU | 7250998 A | 11/1998 |
| AU | 702320 B2 | 2/1999 |
| AU | 8898998 A | 3/1999 |
| AU | 706697 B2 | 6/1999 |
| AU | 1696899 A | 6/1999 |
| AU | 708219 B2 | 7/1999 |
| AU | 726813 B2 | 11/2000 |
| AU | 727753 B2 | 12/2000 |
| AU | 6742100 A | 3/2001 |
| AU | 733021 B2 | 5/2001 |
| AU | 734462 B2 | 6/2001 |
| AU | 734727 B2 | 6/2001 |
| AU | 737586 B2 | 8/2001 |
| AU | 740551 B2 | 11/2001 |
| AU | 741760 B2 | 12/2001 |
| AU | 752856 B2 | 10/2002 |
| AU | 755686 B2 | 12/2002 |
| AU | 2002315568 A1 | 3/2003 |
| AU | 2002324712 A1 | 3/2003 |
| AU | 760814 B2 | 5/2003 |
| AU | 2003101051 A4 | 2/2004 |
| AU | 2001257622 B2 | 4/2004 |
| AU | 2004208580 A1 | 8/2004 |
| AU | 2001239893 B2 | 11/2004 |
| AU | 778528 B2 | 12/2004 |
| AU | 2001260829 B2 | 12/2004 |
| AU | 780141 B2 | 3/2005 |
| AU | 2002100728 B9 | 3/2005 |
| AU | 2002256333 B2 | 4/2005 |
| AU | 781718 B2 | 6/2005 |
| AU | 781796 B2 | 6/2005 |
| AU | 2004210544 C1 | 7/2005 |
| AU | 783062 B2 | 9/2005 |
| AU | 783538 B2 | 11/2005 |
| AU | 2005209631 A1 | 3/2006 |
| AU | 2004283635 B2 | 5/2006 |
| AU | 2002337974 B2 | 6/2006 |
| AU | 2003218722 B2 | 8/2006 |
| AU | 2002332990 B2 | 5/2007 |
| AU | 2007305271 A1 | 4/2008 |
| AU | 2002344685 B2 | 5/2008 |
| AU | 2006202021 B2 | 9/2008 |
| AU | 2004210542 C1 | 1/2009 |
| AU | 2006223699 B2 | 2/2009 |
| AU | 2004253248 B2 | 6/2010 |
| AU | 2005267738 B2 | 1/2011 |
| AU | 2006297477 B2 | 2/2011 |
| AU | 2005232671 B2 | 3/2011 |
| AU | 2006235703 B2 | 6/2011 |
| AU | 2006306883 B2 | 2/2012 |
| AU | 2010277872 A1 | 2/2012 |
| AU | 2010296886 A1 | 4/2012 |
| AU | 2004292397 C1 | 11/2012 |
| AU | 2012278918 A1 | 4/2013 |
| AU | 2011347802 B2 | 5/2013 |
| AU | 2012203345 B2 | 7/2013 |
| AU | 2013242835 A1 | 10/2013 |
| AU | 2008258881 B2 | 12/2013 |
| AU | 2009320500 B2 | 9/2014 |
| AU | 2013239252 B2 | 9/2014 |
| AU | 2012260799 B2 | 8/2015 |
| AU | 2014263135 B2 | 2/2016 |
| AU | 2016200312 A1 | 2/2016 |
| AU | 2014324161 A1 | 4/2016 |
| AU | 2016415998 A1 | 7/2016 |
| AU | 2012346157 B2 | 8/2016 |
| AU | 2015271808 A1 | 12/2016 |
| AU | 2010277872 C1 | 1/2017 |
| AU | 2014201152 C1 | 1/2017 |
| AU | 2015301596 A1 | 2/2017 |
| AU | 2012269805 B2 | 3/2017 |
| AU | 2015335946 A1 | 5/2017 |
| AU | 2012305915 B2 | 9/2017 |
| AU | 2016274888 A1 | 1/2018 |
| AU | 2016213866 B2 | 3/2018 |
| AU | 2013205966 A1 | 5/2018 |
| AU | 2015211711 B2 | 5/2018 |
| AU | 2016419441 A1 | 5/2018 |
| AU | 2017268840 A1 | 11/2018 |
| AU | 2018229465 A1 | 4/2019 |
| AU | 2018212273 A1 | 9/2019 |
| AU | 2018260557 A1 | 11/2019 |
| AU | 2018338745 A1 | 4/2020 |
| AU | 2018362266 A1 | 6/2020 |
| AU | 2018383221 A1 | 7/2020 |
| AU | 2020210180 A1 | 8/2020 |
| AU | 2019224928 A1 | 9/2020 |
| AU | 2016365123 B2 | 11/2020 |
| AU | 2019272711 A1 | 11/2020 |
| AU | 2019279916 B2 | 11/2020 |
| AU | 2020244597 A1 | 11/2020 |
| AU | 2022100024 | 5/2022 |
| CA | 2486585 C | 7/2012 |
| CA | 2725380 C | 8/2013 |
| CA | 2947246 A1 | 11/2015 |
| CA | 3042497 A1 | 5/2017 |
| CA | 3065004 A1 | 12/2018 |
| CA | 3109527 A1 | 2/2020 |
| CA | 3112317 A1 | 3/2020 |
| CA | 3112369 A1 | 3/2020 |
| CA | 3014897 C | 12/2020 |
| EP | 0 164 241 A2 | 12/1985 |
| EP | 0 219 458 B1 | 4/1987 |
| EP | 0333311 | 1/1989 |
| EP | 1 443 898 B1 | 1/2009 |
| EP | 1 965 809 B1 | 9/2009 |
| EP | 2 361 053 A1 | 8/2011 |
| EP | 2 158 484 B1 | 11/2011 |
| EP | 2 432 478 A2 | 3/2012 |
| EP | 1 868 566 B1 | 3/2013 |
| EP | 2 291 072 B1 | 7/2013 |
| EP | 2 453 760 B1 | 9/2013 |
| EP | 2 653 031 A1 | 10/2013 |
| EP | 2 654 455 B1 | 10/2013 |
| EP | 1 542 543 B1 | 11/2013 |
| EP | 2 588 855 B1 | 3/2014 |
| EP | 2 720 532 A1 | 4/2014 |
| EP | 2 767 289 A1 | 8/2014 |
| EP | 2 767 289 B1 | 8/2014 |
| EP | 2 558 855 B1 | 10/2014 |
| EP | 2 566 319 B1 | 12/2014 |
| EP | 2 830 434 B1 | 2/2015 |
| EP | 2 709 442 B1 | 3/2015 |
| EP | 2 724 670 B1 | 6/2015 |
| EP | 2 630 484 B1 | 7/2015 |
| EP | 2 573 165 B1 | 10/2015 |
| EP | 2 905 013 B1 | 8/2016 |
| EP | 2 306 846 B1 | 11/2016 |
| EP | 2 306 847 B1 | 11/2016 |
| EP | 3 102 219 B1 | 12/2016 |
| EP | 3 104 885 B1 | 12/2016 |
| EP | 3 105 581 A1 | 12/2016 |
| EP | 3 151 679 A1 | 4/2017 |
| EP | 2 493 287 B1 | 10/2017 |
| EP | 3 253 228 A1 | 12/2017 |
| EP | 3 258 948 A1 | 12/2017 |
| EP | 3 273 793 A2 | 1/2018 |
| EP | 2 536 295 B1 | 4/2018 |
| EP | 3 307 158 A1 | 4/2018 |
| EP | 3 327 030 A1 | 5/2018 |
| EP | 2 629 602 B1 | 7/2018 |
| EP | 3 389 489 A1 | 10/2018 |
| EP | 3 399 872 A1 | 11/2018 |
| EP | 3 403 493 A1 | 11/2018 |
| EP | 3 416 501 A1 | 12/2018 |
| EP | 3 451 851 A1 | 3/2019 |
| EP | 2 214 481 B1 | 5/2019 |
| EP | 2 994 900 B1 | 7/2019 |

(56) References Cited

FOREIGN PATENT DOCUMENTS

| | | | |
|---|---|---|---|
| EP | 3 540 679 A1 | 9/2019 |
| EP | 3 558 027 A1 | 10/2019 |
| EP | 3 570 683 A1 | 11/2019 |
| EP | 3 614 921 A1 | 3/2020 |
| EP | 3 618 640 A1 | 3/2020 |
| EP | 3 628 169 A1 | 4/2020 |
| EP | 3 650 035 A1 | 5/2020 |
| EP | 3 654 939 A1 | 5/2020 |
| EP | 1 545 464 B1 | 9/2020 |
| EP | 3 450 974 B1 | 11/2020 |
| EP | 3 743 051 A1 | 12/2020 |
| EP | 3 766 359 A1 | 1/2021 |
| EP | 3 784 647 A1 | 3/2021 |
| GB | 1 445 560 A | 8/1976 |
| GB | 2 353 707 A | 3/2001 |
| GB | 2 408 453 B | 6/2006 |
| GB | 2 425 259 B | 9/2008 |
| GB | 2 477 236 A | 7/2011 |
| GB | 2 510 826 B | 8/2014 |
| IE | 20130280.9 A1 | 9/2014 |
| IE | 86582 B1 | 9/2015 |
| NZ | 119910 | 5/1958 |
| NZ | 167001 | 9/1973 |
| NZ | 173487 | 1/1976 |
| NZ | 187228 A | 2/1981 |
| NZ | 187365 A | 3/1981 |
| NZ | 188277 A | 3/1981 |
| NZ | 188280 A | 4/1981 |
| NZ | 190386 A | 4/1981 |
| NZ | 191587 A | 10/1981 |
| NZ | 188278 A | 3/1982 |
| NZ | 192048 A | 3/1982 |
| NZ | 191509 A | 12/1982 |
| NZ | 194682 A | 5/1983 |
| NZ | 194901 A | 7/1983 |
| NZ | 197313 A | 7/1984 |
| NZ | 197543 A | 12/1984 |
| NZ | 200714 A | 12/1984 |
| NZ | 203102 A | 5/1985 |
| NZ | 204511 A | 9/1985 |
| NZ | 204615 A | 4/1986 |
| NZ | 207783 A | 6/1986 |
| NZ | 201891 A | 11/1986 |
| NZ | 210757 A | 11/1986 |
| NZ | 204879 A | 12/1986 |
| NZ | 207953 A | 2/1987 |
| NZ | 208513 A | 6/1987 |
| NZ | 209913 A | 8/1987 |
| NZ | 212181 A | 11/1987 |
| NZ | 210601 A | 1/1988 |
| NZ | 211320 A | 2/1988 |
| NZ | 213281 A | 3/1988 |
| NZ | 217092 A | 6/1988 |
| NZ | 212100 A | 7/1988 |
| NZ | 213400 A | 7/1988 |
| NZ | 220024 A | 5/1989 |
| NZ | 216865 A | 7/1989 |
| NZ | 216991 A | 9/1989 |
| NZ | 222043 A | 9/1989 |
| NZ | 220178 A | 10/1989 |
| NZ | 221426 | 11/1989 |
| NZ | 216477 | 12/1989 |
| NZ | 222557 A | 12/1989 |
| NZ | 221071 A | 3/1990 |
| NZ | 222899 A | 4/1990 |
| NZ | 219300 A | 6/1990 |
| NZ | 226595 A | 8/1990 |
| NZ | 219493 A | 9/1990 |
| NZ | 229808 A | 12/1990 |
| NZ | 228322 A | 2/1991 |
| NZ | 232321 A | 2/1991 |
| NZ | 227329 A | 6/1991 |
| NZ | 227772 A | 6/1991 |
| NZ | 224981 A | 7/1991 |
| NZ | 227237 A | 8/1991 |
| NZ | 234227 A | 8/1991 |
| NZ | 230877 A | 9/1991 |
| NZ | 233686 A | 9/1991 |
| NZ | 233368 A | 11/1991 |
| NZ | 231758 A | 1/1992 |
| NZ | 234580 A | 5/1992 |
| NZ | 236627 A | 5/1992 |
| NZ | 228382 A | 8/1992 |
| NZ | 238612 A | 10/1992 |
| NZ | 235076 A | 2/1993 |
| NZ | 243890 A | 3/1993 |
| NZ | 233314 A | 4/1993 |
| NZ | 232607 A | 5/1993 |
| NZ | 237384 A | 6/1993 |
| NZ | 240222 A | 3/1994 |
| NZ | 248672 A | 4/1994 |
| NZ | 243105 A | 7/1994 |
| NZ | 242937 A | 9/1994 |
| NZ | 245076 A | 9/1994 |
| NZ | 242225 A | 2/1995 |
| NZ | 244501 A | 7/1995 |
| NZ | 250183 A | 9/1995 |
| NZ | 255579 A | 3/1996 |
| NZ | 260514 A | 5/1996 |
| NZ | 264061 A | 6/1996 |
| NZ | 270639 A | 6/1996 |
| NZ | 253999 A | 7/1996 |
| NZ | 280398 A | 12/1996 |
| NZ | 280886 A | 1/1997 |
| NZ | 278977 A | 3/1997 |
| NZ | 299436 A | 3/1997 |
| NZ | 280067 A | 4/1997 |
| NZ | 290045 A | 8/1997 |
| NZ | 278770 A | 9/1997 |
| NZ | 289179 A | 12/1997 |
| NZ | 314295 A | 7/1998 |
| NZ | 330507 A | 7/1998 |
| NZ | 288144 A | 12/1998 |
| NZ | 329770 A | 1/2000 |
| NZ | 502119 A | 6/2000 |
| NZ | 326953 A | 3/2001 |
| NZ | 336074 A | 10/2001 |
| NZ | 504631 A | 2/2002 |
| NZ | 503571 A | 4/2003 |
| NZ | 516423 A | 7/2003 |
| NZ | 516083 A | 8/2003 |
| NZ | 514279 A | 2/2004 |
| NZ | 526939 A | 11/2004 |
| NZ | 530317 A | 10/2005 |
| NZ | 529177 A | 12/2005 |
| NZ | 531672 A | 8/2006 |
| NZ | 535167 A | 8/2006 |
| NZ | 538016 A | 8/2006 |
| NZ | 538087 A | 4/2007 |
| NZ | 535258 A | 8/2007 |
| NZ | 538813 A | 9/2007 |
| NZ | 554633 A | 11/2008 |
| NZ | 547418 A | 4/2009 |
| NZ | 572035 A | 2/2010 |
| NZ | 572736 A | 3/2010 |
| NZ | 573142 A | 3/2010 |
| NZ | 573143 A | 3/2010 |
| NZ | 563055 A | 4/2010 |
| NZ | 576414 A | 8/2010 |
| NZ | 581768 A | 6/2011 |
| NZ | 579803 A | 9/2011 |
| NZ | 578771 A | 10/2011 |
| NZ | 594862 A | 11/2011 |
| NZ | 590284 A | 5/2012 |
| NZ | 573656 A | 6/2012 |
| NZ | 596143 A | 8/2012 |
| NZ | 593497 A | 1/2013 |
| NZ | 589429 A | 2/2013 |
| NZ | 610896 | 8/2013 |
| NZ | 600516 A | 1/2014 |
| NZ | 602979 A | 5/2014 |
| NZ | 617849 A | 5/2015 |
| NZ | 610031 A | 6/2015 |
| NZ | 610343 A | 7/2015 |

(56) References Cited

FOREIGN PATENT DOCUMENTS

| | | |
|---|---|---|
| NZ | 708284 A | 10/2015 |
| NZ | 630295 | 12/2015 |
| NZ | 708374 | 3/2016 |
| NZ | 714513 A | 6/2016 |
| NZ | 629374 A | 11/2016 |
| NZ | 727563 A | 5/2018 |
| NZ | 722336 A | 2/2021 |
| NZ | 739154 A | 2/2021 |
| NZ | 750914 A | 3/2021 |
| WO | WO 8906943 | 8/1989 |
| WO | WO-95/19763 A1 | 7/1995 |
| WO | WO-96/14062 A1 | 5/1996 |
| WO | WO-2005/082270 A1 | 9/2005 |
| WO | WO 2011014078 | 2/2011 |
| WO | WO-2014/200365 A1 | 12/2014 |
| WO | WO-2015/109362 A2 | 7/2015 |
| WO | WO-2015/109362 A3 | 7/2015 |
| WO | WO 2016102931 | 6/2016 |
| WO | WO-2017/095821 A1 | 6/2017 |
| WO | WO-2017/103239 A1 | 6/2017 |
| WO | WO-2017/119959 A1 | 7/2017 |
| WO | WO-2017/120495 A1 | 7/2017 |
| WO | WO-2018/018062 A1 | 2/2018 |
| WO | WO-2018/153702 A1 | 8/2018 |
| WO | WO-2018/197620 A1 | 11/2018 |
| WO | WO-2018/201139 A1 | 11/2018 |
| WO | WO-2018/236894 A1 | 12/2018 |
| WO | WO-2019/032144 A1 | 2/2019 |
| WO | WO-2019/043091 A1 | 3/2019 |
| WO | WO-2019/089333 A1 | 5/2019 |
| WO | WO-2019/145345 A1 | 8/2019 |
| WO | WO-2019/206892 A1 | 10/2019 |
| WO | WO-2020/055270 A1 | 3/2020 |
| WO | WO-2020/113279 A1 | 6/2020 |
| WO | WO-2020/245303 A1 | 12/2020 |
| WO | WO 2021005202 | 1/2021 |
| WO | WO-2021/116395 A1 | 6/2021 |
| WO | WO 2021163148 | 8/2021 |
| WO | WO 2021205420 | 10/2021 |
| WO | WO-2022/136857 A1 | 6/2022 |
| WO | WO 2022124914 | 6/2022 |
| WO | WO 2022136857 | 6/2022 |
| WO | WO 2022218967 | 10/2022 |
| WO | WO 2022221925 | 10/2022 |
| WO | WO 2023163600 | 8/2023 |
| WO | WO 2023247942 | 12/2023 |
| WO | WO 2024011207 | 1/2024 |

OTHER PUBLICATIONS

Cardinal, "Intraruminal controlled release boluses", Controlled Release Veterinary Drug Delivery, pp. 51-82.
Morais et al., "Seaweed Potential in the Animal Feed: A Review", J. Marine Sci. & Eng. 2020, vol. 8(8), 559 (Jul. 25, 2020).
Thompson and Rowntree, "Invited Review: Methane sources, quantification, and mitigation in grazing beef systems", Applied Animal Science; vol. 36, Issue 4, Aug. 2020, pp. 556-573 (Jul. 25, 2020).
Statement of Grounds and Particulars dated Aug. 2, 2023 in corresponding AU patent application No. 2021221810.
International Preliminary Report on Patentability in International Appln. No. PCT/NZ2021/050216, mailed on Jun. 13, 2023, 7 pages.
Abbott et al., "Seaweed and Seaweed Bioactives for Mitigation of Enteric Methane: Challenges and Opportunities", Animals, Dec. 18, 2020, pp. 1-28, vol. 10.
Author Unknown, "Environmental Stress Cracking Test Results", NatureWorks LLC, 4 pages.
Author Unknown, "Part III Consumer Information: Sandoz Diclofenac", Sep. 30, 2014, pp. 34-38, Sandoz Canada Inc.
Author Unknown, "The answer to livestock that burp methane may be seaweed", Nov. 2, 2019 edition,[online], [retrieved online Dec. 10, 2021], 6 pages.
Author Unknown, "CH4 Global", [online], [retrieved Dec. 10, 2021] 15 pages.
Author Unknown, "Reducing New Zealand's Agricultural Greenhouse Gases: Methane Inhibitors", Jul. 2017, 8 pages [online], produced by New Zealand Agricultural Greenhouse Gas Research Centre (NZAGRC) & Pastoral Greenhouse Gas Research Consortium (PGgRc).
Author Unknown, "Rumensin Anti-Bloat Capsule" www.nzfarmsource.co.nz, 4 pages [online], product # 238974, [retrieved online Dec. 10, 2021].
Author Unknown, Product Data: Corbion Purac—Luminy L130; rev.no.4 dated Dec. 22, 2016, 3 pages.
Beauchemin et al., (Animal 2020;14(S1):2-16) (Year: 2020).
Berghuis et al., "Hydrogenotrophic methanogenesis in archaeal phylum Verstraetearchaeota reveals the shared ancestry of all methanogens" PNAS, Mar. 12, 2019, pp. 5037-5044, vol. 116, No. 11.
Carpenter et al., "Bromoform in tropical Atlantic air from 24 degrees N to 24 degrees S", Geophysical Research Letters, 2007, pp. 1-5, vol. 32, L11810, the American Geophysical Union.
Denman et al., "Quantitation and diversity analysis of ruminal methanogenic populations in response to the antimethanogenic compound bromochloromethane", Federation of European Microbiological Societies, Nov. 2007, pp. 313-322, vol. 62, Blackwell Publishing Ltd.
Edited by Hardee E Gregory & Baggot J Desmond: "Development and Formulation of Veterinary Dosage Forms", vol. 88, 2nd edition, published by Marcel Dekker, Inc.
Examination Report No. 1, issued in related AU Application No. 2021221810, mailed Jan. 24, 2022.
Getabalew et al. (Journal of Veterinary Medicine and Animal Sciences 2020;3(1):5 pages). (Year: 2020).
Gorrasi et al., "Effect of PLA grades and morphologies on hydrolytic degradation at composting temperature: Assessment of structural modification and kinetic parameters", Polymer Degradation and Stability, 2013, p. 1006-1014, vol. 98, Elsevier Ltd.
Haisan et al., "The effects of feeding 3-nitrooxypropanol on methane emissions and productivity of Holstein cows in mid lactation", Journal of Dairy Science, 2014, pp. 3110-3119, vol. 97, No. 5, American Dairy Science Association.
Hristov et al., "An inhibitor persistently decreased enteric methane emission from dairy cows with no negative effect on milk production", PNAS, Aug. 25, 2015, pp. 10663-10668, vol. 112, No. 34.
Hutching, "Nz scientists say seaweed cure for methane emissions comes up short", Business, Dec. 30, 2016, 10 pages [online], [retrieved online May 25, 2020].
International Search Report & Written Opinion of the International Searching Authority issued in PCT Application No. PCT/NZ2021/050216, mailed Feb. 28, 2022.
Kinley et al., "Mitigating the Carbon Footprint and Improving productivity of Ruminant Livestock Agriculture Using a Red Seaweed", Journal of Cleaner Production, Mar. 2, 2020, pp. 1-10, vol. 259, Elsevier Ltd.
Kinley, "Asparagopsis feedlot feeding trial", Final Report, Meat & Livestock Australia, May 31, 2018, 42 pages [online], CSIRO, published by Meat and Livestock Australia Limited.
Kurt, "Enteric Fermentation/Enteric Methane" [retrieved from internet on Jan. 17, 2022] <URL: https://arpa-e.energy.gov/sites/default/files/Session%201.1%20-%20Kurt_0.pdf>, available from Oct. 20, 2020, 13 pages.
Lan et al., "Ruminal methane production: Associated microorganisms and the potential of applying hydrogen-utilizing bacteria for mitigation" Science of the Total Environment, pp. 1270-1283, vol. 654, Elsevier B.V.
Lanigan, "Metabolism of Pyrrolizidine Alkaloids in the Ovine Rumen", Australian Journal of Agricultural Research, 1972, pp. 1085-1091, vol. 23.
Lili et al., "Asparagopsis taxiformis decreases enteric methane production from sheep", Animal Production Science, Aug. 2016, pp. A-H, Csiro Publishing.
Mitsumori et al., "Responses in digestion, rumen fermentation and microbial populations to inhibition of methane formation by a halogenated methane analogue", British Journal of Nutrition, 2012, pp. 482-491, vol. 108.

(56) References Cited

OTHER PUBLICATIONS

Non-Final Office Action on U.S. Appl. No. 17/544,445 dated Apr. 15, 2022.
Notice of Allowance on U.S. Appl. No. 17/544,445 dated Aug. 10, 2022.
Odongo et al. (J Dairy Sci 2007;90: 1781-1788). (Year: 2007).
Patra et al., "Rumen methanogens and mitigation of methane emission by anti-methanogenic compounds and substances" Journal of Animal Science and Biotechnology, 2017, pp. 1-18, vol. 8, No. 13.
Rennie et al., "Farmers Weekly", Nov. 2, 2020, vol. 19, No. 42, 72 pages.
Romero-Perez et al., "Effects of 3-nitrooxypropanol on methane production using the rumen simulation technique (Rusitec)", Animal Feed Science and Technology, 2015, pp. 98-109, vol. 209, Elsevier B.V.
Roque et al., "Effect of the macroalgae Asparagopsis taxiformis on methane production and rumen microbiome assemblage", Animal Microbiome, 2019, pp. 1-14, vol. 1, No. 3.
Roque et al., "Inclusion of Asparagopsis armata in lactating dairy cows' diet reduces enteric methane emission by over 50 percent", Journal of Cleaner Production, 2019, pp. 132-138, vol. 234, Elsevier Ltd.
Schwartz et al., "Drug Release from Wax matrices I", Journal of Pharmaceutical Sciences, Feb. 1968, pp. 274-277, vol. 57, No. 2.
Siepmann et al., "Modeling of diffusion controlled drug delivery", Journal of Controlled Release, 2012, pp. 351-362, vol. 161, Elsevier B.V.
Smith, "Seaweed helps cut methane emissions", Jul. 2017, [online], [retrieved online Apr. 21, 2021], 8 pages.
Sturges et al., "Bromoform as a source of stratospheric bromine", Geophysical Research Letters, Jul. 15, 2000, pp. 2081-2084, vol. 27, No. 14, The American Geophysical Union.
Sturges et al., "Bromoform emission from artic ice algae", Nature, Aug. 20, 1992, pp. 660-662, vol. 358, Nature Publishing Group.
Tegtmeier et al., "Oceanic bromoform emissions weighted by their ozone depletion potential", Atmospheric Chemistry and Physics, 2015, pp. 13647-13663, vol. 16, Copernicus Publications on behalf of the European Geosciences Union.
Tsuji et al., "Stereocomplex formation between enantiomeric poly (lactic acid)s. XI Mechanical Properties and morphology of solution-cast films" Polymer, 1999, pp. 6699-6708, vol. 40, Elsevier Science Ltd.
Uchida et al. "Adsorption removal of chloroform and bromoform by activated carbon fiber", Toxicological & Environmental Chemistry, 1997, pp. 227-231, vol. 63, Nos. 1-4, OPA (Overseas Publishers Association), Amsterdam B.V.
Ungerfeld, "Inhibition of Rumen Methanogenesis and Ruminant Productivity: A Meta-Analysis", Frontiers in Veterinary Science, Jun. 19, 2018, pp. 1-13, vol. 5, Article 113.
Ungerfeld, Em (Frontiers in Veterinary Science 2018;5:13 pages) (Year: 2018).
US Office Action on U.S. Appl. No. 17/544,445 dated Feb. 10, 2022.
Vandamme et al., "Issues and Challenges in Developing Ruminal Drug Delivery Systems", Advanced Drug Delivery Reviews, Apr. 12, 2004, pp. 1415-1436, vol. 56, Elsevier B.V.
Weidner et al., "Thermal and Morphological Properties of Poly(L-Lactic Acid)/POly(D-Lactic Acid)-B-Polycaprolactone Diblock Copolymer Blends", Materials, 2020, pp. 1-18, vol. 13.
Yonezawa et al., "Release from or through a wax matrix system II. Basic properties of release from or through the Wax Matrix Layer", Chemical and Pharmaceutical Bulletin, Feb. 2002, pp. 220-224, vol. 50, No. 2, Pharmaceutical Society of Japan.
Zhou et al., "Bromoform and dibromomethane measurements in the seacoast region, 2002-2004", Journal of Geophysical Research, 2008, pp. 1-19, vol. 113, D08305, The American Geophysical Union.
International Written Opinion of the International Search Authority issued in PCT Application No. PCT/AU2022/050836, mailed Sep. 16, 2022.
Grainger et al., "Can enteric methane emissions from ruminants be lowered without lowering their production?" Anim. Feed Sci. Technol., Jun. 2011, 166-167:308-320.
Henderson et al., "Enzyme- and gene-based approaches for developing methanogen-specific compounds to control ruminant methane emissions: a review," Animal Production Science, Apr. 2016, 58(6):1017-1026.
McGinn et al., "Assessment of the SF6 tracer technique for measuring enteric methane emissions from cattle," J. Environ. Qual., Aug. 2006, 35(5):1686-1691.
Office Action in U.S. Appl. No. 17/987,989, dated Apr. 2, 2024, 9 pages.
Aliotta et al., "A Brief Review of Poly (Butylene Succinate) (PBS) and Its Main Copolymers: Synthesis, Blends, Composites, Biodegradability, and Applications," Polymers (Basel), Feb. 2022, 14(4):844, 23 pages.
Coiai et al., "Binary Green Blends of Poly(lactic acid) with Poly(butylene adipate-co-butylene terephthalate) and Poly(butylene succinate-co-butylene adipate) and Their Nanocomposites," Polymers (Basel), Jul. 2021, 13(15):2489, 32 pages.
Hajnal et al., "Dairy Cattle Rumen Bolus Developments with Special Regard to the Applicable Artificial Intelligence (AI) Methods," Sensors (Basel), Sep. 2022, 22(18):6812, 16 pages.
Zhao et al., "Super tough poly(lactic acid) blends: a comprehensive review," RSC Advances, Jan. 2020, 10(22):13316-13368.
Byford et al., "A Sustained-release Oxytetracycline Bolus for Ruminants," Bovine Practitioner, Nov. 1980, 15:91-94.
Byford, "Prophylaxis and control of vector borne anaplasmosis with sustained-release boluses," Thesis for the degree of Master of Science, Oklahoma State University, May 1980, 84 pages.
Conrad et al., "Controlled sustained delivery of monensin in cattle: the Monensin R.D.D," Journal of Controlled Release, Jul. 1989, 9(2):133-147.
Controlled Release Veterinary Delivery, 1st ed., Rathbone M.J. & Gurny R. (Eds.), Jul. 2000, Chapters 2 and 3, 66 pages.
Formulation of Veterinary Dosage Forms, 1st ed., Blodinger (ed.), 1983, Chapters 2-4, 134 pages.
Honan et al., "Feed additives as a strategic approach to reduce enteric methane production in cattle: modes of action, effectiveness and safety," Animal Production Science, Feb. 2021, 62:1303-1317.
McGurrin et al., "Anti-methanogenic potential of seaweeds and seaweed-derived compounds in ruminant feed: current perspectives, risks and future prospects," Journal of Animal Science and Biotechnology, Dec. 2023, 14:145, 27 pages.
Opposition, "Declaration of Stephen Page," Exhibit 1 in Australian Appln. No. 2022100024, dated May 8, 2024, 107 pages.
Riner, "Sustained-release ruminal boluses and factors determining their release rates," Thesis for the degree of Doctor of Philosophy, Oklahoma State University, Dec. 1981, 97 pages.
Statement of Grounds and Particulars dated May 21, 2024, in corresponding AU patent application No. 2022100024, 36 pages.
Teel, "A sustained-release systemic acaracide bolus for tick control in bovine," Thesis for the degree of Doctor of Philosophy, Oklahoma State University, May 1978, 127 pages.
Thombre et al., "A delivery device containing a poorly water-soluble drug in a hydrophobic medium: ruminal delivery application," Journal of Controlled Release, 1992, 18(3):221-233.
Tomkins et al., "A bromochloromethane formulation reduces enteric methanogenesis in cattle fed grain-based diets," Animal Production Science, Nov. 2009, 49(12):1053-1058.
Vandamme et al., "Controlled release of levamisole from poly-(ε-caprolactone) matrices: III. Effects of molecular weight and polymer coating on drug release," International Journal of Pharmaceutics, Dec. 1996, 145(1-2):77-86.
Patent Examination Report in New Zealand Appln. No. 796269, dated May 24, 2024, 3 pages.
Office Action in Russian Appln. No. 2023117918, dated Aug. 23, 2024, 27 pages (with English translation).
Biomaterials Science: An Introduction to Materials in Medicine, 3rd ed., Ratner (ed.), Oct. 2012, Chapter 1, 30 pages.
Introduction to Polymers, 3rd ed., Young (ed.), Mar. 2013, Chapter 18, 20 pages.

(56) References Cited

OTHER PUBLICATIONS

Polymer Blends and Composites, 1st ed., Manson (ed.), 1976, Chapter 2, 68 pages.
Statement of Grounds and Particulars dated Aug. 22, 2024 in corresponding AU patent application No. 2023200195, 36 pages.
Su et al., "Uncompatibilized PBAT/PLA Blends: Manufacturability, Miscibility and Properties," Materials, Oct. 2020, 13:4897, 17 pages.
Office Action in Australian Appln. No. 2023200195, dated Feb. 28, 2024, 4 pages.
Office Action in Australian Appln. No. 2023200196, dated Feb. 28, 2024, 4 pages.
Notice of Allowance in U.S. Appl. No. 17/987,989, dated Sep. 19, 2024, 8 pages.

* cited by examiner

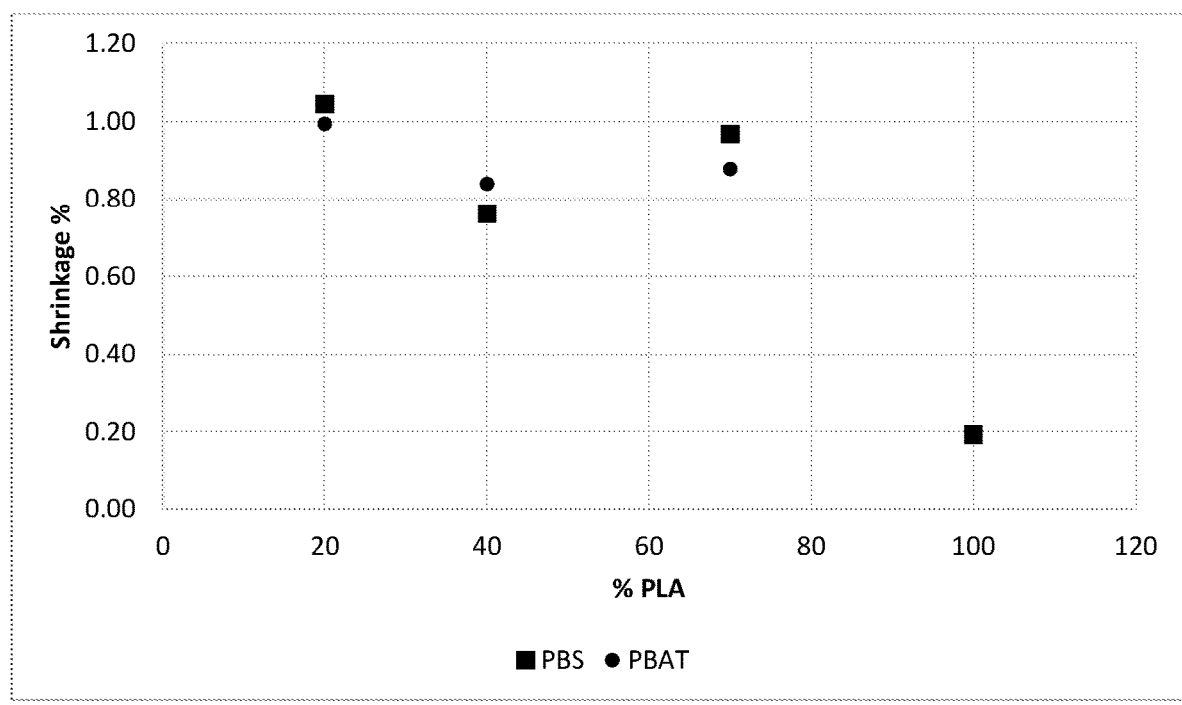

DEVICES AND METHODS FOR DELIVERY OF SUBSTANCES TO ANIMALS

CROSS-REFERENCE TO RELATED PATENT APPLICATIONS

The present application is a continuation of U.S. patent application Ser. No. 17/544,445, filed Dec. 7, 2021, which claims priority under 35 U. S. C. § 119 to New Zealand Application No. 770786, filed Dec. 8, 2020, Australian Application No. 2021900932, filed Mar. 30, 2021, and Australian Application No. 2021221810, filed Aug. 25, 2021, the contents of which are hereby incorporated by reference in their entireties.

FIELD OF INVENTION

The present invention relates to improvements in devices and methods for animal production and delivery of substances to animals, and in particular to devices and methods for administering at least one advantageous substance to an animal, and methods of manufacturing the devices.

BACKGROUND TO THE INVENTION

In farming it is often necessary to deliver substances to animals. This can be for any of various purposes, including but not limited to treatment or prevention of disease and to increase animal production.

There are various devices and methods to deliver substances such as medicament to animals. However, one class of compounds that are difficult to deliver to animals are hydrophobic compounds. The properties of these compounds present challenges to developing technology for the controlled release of these hydrophobic substances, particularly via an animal's stomach.

One specific purpose to administer substances to animals is to reduce the adverse effects of agriculture. For instance, various methane and nitrification inhibitors are known to be administered to animals to reduce or mitigate the adverse effects of the methane and nitrate containing compounds produced by the animals.

However, despite current efforts, climate change is creating a wide range of environmental and social impacts globally. It is widely understood that these impacts will only continue to increase over time. As a result, there has been a global push to reduce harmful greenhouse gas (GHG) emissions in an effort to avoid the worst effects of climate change.

The agricultural sector is considered to be a major source of GHG emissions. Total emissions of methane from global livestock accounts for an estimated 7.1 gigatons of $CO_2$-equivalent per year, representing 14.5% of all anthropogenic GHG emissions. Therefore, this sector will play a key role in reducing overall GHG emissions.

The main GHGs released by agriculture are methane ($CH_4$) and nitrous oxide ($N_2O$), with the main source of methane emission attributed to livestock. Most methane is emitted when cattle burp. The amount of methane produced for each farm is directly related to the total animal feed intake.

Countries which have a strong agricultural sector such as New Zealand, face challenging goals of reducing agricultural emissions. For instance, the New Zealand government has introduced policies aimed to reduce methane emission by 24-50% before 2050. In New Zealand livestock methane production is estimated to comprise as much as half of the country's total GHG emissions. The reduction of methane is a critical component of meeting targets for emissions of GHGs and reducing the effects of global warming.

Release of GHGs by animals also has adverse effects on animal productivity. Any feed that is converted to a compound which is subsequently expired or released by the animal is an energy source that has not been converted to a productive use. Accordingly, for efficiency, it is important to optimise conversion of feeds into animal productivity in the form of weight gain or milk production.

OBJECT OF THE INVENTION

It is an object of the present invention to provide improved devices and methods to deliver substances to an animal, e.g. hydrophobic substances and/or methane inhibitors.

It is an object of the invention to provide devices and methods to reduce emission of GHGs.

It is an object of the invention to provide devices and methods to improve or optimise animal productivity.

Alternatively, it is an object of the invention to provide devices and methods to improve animal production gains e.g. through reduction of methane production.

It is an object of the invention to provide a formulation to reduce emission of GHGs by one or more animals e.g. a ruminant animal.

It is an object of the invention to provide devices and methods that can release substances at different rates over a period of time.

Alternatively, it is an object of the invention to provide methods of manufacturing devices to deliver substances to an animal e.g. substances to reduce emission of GHGs.

Alternatively, it is an object of the invention to overcome some of the disadvantages of the prior art.

Alternatively, it is an object of the present invention to provide the public with a useful choice.

SUMMARY OF THE INVENTION

According to one aspect of the invention, there is provided a bolus configured for administration to an animal, wherein said bolus is configured to release a hydrophobic substance to the animal over a period of time.

According to one aspect of the invention, there is provided a bolus for administration to a ruminant animal, wherein said bolus is configured to release an effective amount of the substance, wherein the substance is preferably at least one inhibiting agent.

According to a further aspect of the invention, there is provided a method for reducing emission of gas (preferably methane) from a ruminant animal, the method comprising the step of administering to said ruminant animal a bolus comprising at least one inhibiting agent.

According to another aspect of the invention, there is provided a use of a methane inhibitor and a carrier in a bolus for reducing methane production in a ruminant animal.

According to another aspect of the invention, there is provided a use of a methane inhibitor and a carrier in a bolus for reducing methane emission from a ruminant animal.

According to another aspect of the invention, there is provided a use of a haloform in the manufacture of a bolus for reducing the emission of one or more greenhouse gases ("GHGs") from a ruminant animal.

In a preferred embodiment, the bolus may be configured to be administered to a ruminant, the ruminant may include beef or dairy cows, sheep, goats, buffalo, deer, elk, giraffes or camels.

In one embodiment, the bolus may be adapted to reduce the release of one or more greenhouse gases ("GHGs") from the ruminant.

In another embodiment, the bolus may be a slow-release bolus, configured to release the at least one inhibiting agent in the ruminant animal over a period of time e.g. in the animal's rumen.

According to a further aspect, there is provided a bolus for administration to a ruminant animal, wherein the bolus comprises:
- a core, wherein the core includes at least one substance to be administered to the ruminant animal mixed with a carrier; and
- a housing which covers at least a portion of the core;
- wherein, the bolus is configured to release the substance through the housing over a period of time.

In another aspect of the invention, there is provided a bolus comprising
- a core which contains a substance to be administered to an animal, and
- a housing which at least partially covers a portion of the core;
- wherein the housing is formed from at least one polylactic acid (PLA).

In a further aspect of the invention, there is provided a bolus comprising
- a core,
- wherein the core comprises a mixture of at least one wax and a haloform.

The inventors have surprisingly found that the technology described herein may provide a number of benefits. These benefits may be the result of the unique synergistic interactions between different aspects of the technology. The technology of the present invention is therefore described based on the inventor's current understanding of these interactions. It should be appreciated any aspect described herein, or the interaction of two or more aspects, may form a distinct invention.

Throughout the present specification reference will be made to the term "substance" or "substance to be administered to an animal". This should be understood as meaning any substance which provides benefits to the animal e.g. a drug for treatment or prevention of disease, which improves animal productivity, or mitigates at least one adverse effect of agriculture.

In preferred embodiments, the substance may be hydrophobic substance.

In particularly preferred embodiments the hydrophobic substance may be an inhibiting agent. Reference will be made herein to the substance as an inhibiting agent. However, this should not be seen as limiting on the scope of the present invention and alternatives are envisaged for the e.g. it may be a hydrophilic substance.

In an embodiment, the at least one inhibiting agent may be a methane inhibitor. The use of a methane inhibitor may provide a number of advantages. For instance, a methane inhibitor will reduce, or eliminate, production of methane by the ruminant e.g. in the rumen. As a result, there is less methane in the rumen which could be emitted by the ruminant and therefore emission of GHGs are effectively reduced.

In addition, reducing production of methane may provide animal production benefits. For instance, reduction of methane ensures that relatively more of the feed ingested is available for digestion and conversion into protein (either milk or meat). As a result, farmers may be able to improve efficiency by either securing greater productivity for a given feed volume or reduce feed accordingly.

In an embodiment, the methane inhibitor may be a haloform.

In a preferred embodiment, the methane inhibitor may be selected from the list of chloroform, bromoform, iodoform, or combinations thereof.

In a particularly preferred form, the haloform may be bromoform ($CHBr_3$). The use of bromoform may provide a number of advantages. For instance, it has a high efficacy for a relatively small dose, which enables one device to deliver sufficient amounts of the inhibiting agent over an extended period of time. In addition, bromoform also has a relatively high density which adds to the overall weight of the bolus and allows for the bolus to be retained in the rumen i.e. it sinks to the ventral part of the rumen rather than floats reducing regurgitation.

However, despite these advantages the inventors have faced a number of challenges and problems to developing a bolus for the controlled release of a haloform, particularly bromoform, to a ruminant.

In a further embodiment, the bolus may comprise a core. The core may be formed by the inhibiting agent mixed with a carrier.

However, in alternative embodiments, the inhibiting agent may be provided in a substantially pure form e.g. is not mixed with a carrier.

In embodiments, the carrier may have a structure which promotes or facilitates affinity for the carrier by the inhibiting agent. For instance, the carrier may have polar functional groups.

In embodiments, the carrier may be a relatively polar substance e.g. it has a relatively high % w/w of polar functional groups. The inventors have surprisingly found that the carrier and the inhibiting agent can interact with each other, and the interaction can affect the release rate of the inhibiting agent from the bolus. This aspect of the invention should become clearer from the following description.

Examples of suitable functional groups for the carrier to include are ester, fatty acids, fatty alcohols, carbonyls and fatty amines. Without being limited to a specific mechanism, the inventors believe that the inhibiting agents may interact with polar functional groups in waxes, potentially via creation of hydrogen bonds. The amount of polar functional groups present in the carrier will affect the affinity of the carrier and the inhibiting agent for each other.

The inventors have found that a range of substances may be suitable for use as a carrier in the present invention. For instance, the carrier may be selected from the list of waxes, myristic acid, stearic acid, steryl alcohol, cetyl alcohol, cetosteryl alcohol or a combination thereof.

In a particularly preferred embodiment, the carrier may be a waxy substance. For example, the carrier may be selected from the list of bee's wax, paraffin wax, PEG4000, Carnauba, castor wax, Candellila, Jojoba, or Lanolin or a combination thereof.

In a particularly preferred embodiment, the carrier may comprise paraffin wax and castor wax.

In a particularly preferred embodiment, the carrier may comprise paraffin wax and castor wax in a ratio of about 50:50 (parts by weight).

In another embodiment, the carrier may comprise a mixture of two or more components. For example, the carrier may comprise a mixture of at least one relatively polar substance with a relatively non-polar substance. For instance, in some forms the carrier may include a mixture of paraffin wax (a mixture of alkanes with no polar functional groups) and castor wax and/or carnauba wax (which have a relatively high amount of polar functional groups). As a result, the overall polarity of the carrier may be adjusted to achieve the desired affinity for the inhibiting agent. This can be used to achieve a desired release rate for the inhibiting agent.

Additionally, to the above, solid carriers such as powdered activated carbon, zeolite or bentonite may also be used as a carrier. Accordingly, the discussion herein should not be seen as limiting on the scope of the present invention.

In a further embodiment, the carrier may also include one or more additional components. For example, additional components such as elemental zinc or zinc oxide may be incorporated. Preferably, a high density material, such as a piece of metal (preferably steel) may be comprised in the carrier. The additional components may be used to achieve a desired density for the core and/or bolus.

It should also be understood that additional components may be added to a cavity of the bolus separate to, and not mixed with, the carrier. This may be particularly beneficial to form a core having a desired release profile, where the density of the bolus can be adjusted to a desired amount by including the additional components.

Other suitable additives for incorporation into the carrier may also include colloidal silicon dioxide, charcoal, bentonite and zeolite(s).

Further aspects of the carrier and its effect on the release of the inhibiting agent from the bolus, together with the interaction of the carrier and housing, should become clearer from the following description.

In a preferred embodiment, the carrier may have a melting point between substantially 50-90° C.

In a particularly preferred embodiment, the carrier has a melting point which is less than the boiling point of the inhibiting agent. This may be useful as the carrier can be melted and mixed with the inhibiting agent without substantial loss of the inhibiting agent due to evaporation.

In a preferred embodiment, the core may have a melting point greater than 37° C.

In a particularly preferred embodiment, the core may have a melting point greater than 40° C.

The melting point of the core may be beneficial to the function of the present technology in several ways. For instance, having a melting point above 37° C., and more preferably 40° C., can assist the carrier in stabilising the inhibiting agent when the bolus is in the rumen. This could be beneficial to control release of the inhibiting agent e.g. movement of the inhibiting agent through the material forming the housing.

In an embodiment, the bolus may be adapted to reach a maximum release rate of approximately 0.05 g to 2 g of bromoform per day into the rumen.

In an embodiment, the bolus may be adapted to release bromoform in an amount of between 0.02 g and 0.5 g per day into the rumen.

In a particularly preferred embodiment, the bolus may be adapted to reach a maximum release rate of approximately 0.1 to 0.5 g of bromoform per day into the rumen.

In a preferred embodiment, the bolus is configured to release bromoform in the amount of between 0.02 g and 0.3 g per day into the rumen.

In an embodiment of the invention, the core of the bolus may comprise the haloform, preferably bromoform, in an amount of 30% (by weight) to 80% (by weight), preferably in an amount of 55% (by weight) to 75% (by weight), more preferably in an amount of 50% (by weight).

In a particularly preferred embodiment, the core comprises the haloform, preferably bromoform, in a concentration of no more than 55% (by weight).

The inventors have found that the rate of release of the inhibiting agent into the rumen increases overtime. This may be the result of several factors. Therefore, the rate of release starts from zero on administration of the animal and increases to a maximum. However, the foregoing should not be seen as limiting, and other release rates are envisaged as within the scope of the present invention.

In a further embodiment, the bolus may include a housing.

Throughout the present specification, reference to the term "housing" should be understood as meaning a structure which can receive and hold a core containing the at least one inhibiting agent.

In preferred embodiments, the housing comprises a body which has a cavity in which a core is located.

However, it should also be understood that the housing may take other forms. For instance, the housing may include two or more cavities which can each receive and hold a separate core.

In one embodiment, the housing may include an open end.

The bolus may be used with an open end e.g. administered to an animal with the end open. As a result, in these embodiments the open end provides an opening to in use expose the contents of the core to fluids in the rumen.

In yet a further and preferred embodiment, the housing may completely cover and surround the core e.g. it has a sealed cavity in which the core is located.

For instance, the bolus may include a housing with a cavity in which at least a portion of the core can be located, and an open end to facilitate insertion of the core into the cavity. A cap can be used to cover the open end.

The cap may be formed separately of the housing and releasably or permanently secured thereto. Alternatively, the cap may be formed integrally to the housing.

In yet a further embodiment, the housing may be provided in at least two-parts, each of which has a cavity to receive a respective portion of the core. Together the at least two parts completely surround the core and define a closed and sealed cavity in which the core is located.

In yet further embodiments, the housing may be formed around the core e.g. by moulding. Alternatively, the housing and cap may together define a substantially closed and sealed cavity in which the core is located.

The inventors believe that the provision of a substantially or completely closed and sealed cavity is preferred because it can assist in achieving a desired controlled release of the inhibiting agent from the bolus of the present invention. For instance, in such an embodiment, the inhibiting agent can pass through the material forming the housing e.g. by mass diffusion.

In embodiments, the housing may be configured to have sufficient structural integrity to remain intact for a predetermined period of time.

In a preferred embodiment, the housing may be configured to degrade over a predetermined period of time.

Throughout the present specification, reference to the term "predetermined period of time" should be understood as meaning the period of time over which the inhibiting agent is to be released to the animal.

In a particularly preferred embodiment, the predetermined period of time may be at least two months, preferably six months, and more preferably 12 months.

The inventors have surprisingly found that housings of the present invention may assist with the controlled release of the inhibiting agent. For instance, the housing is able to withstand the conditions in the rumen for the predetermined period of time. During this time, the housing protects the core from fluid in the rumen, yet can facilitate or contribute to the controlled release of the inhibiting agent. However, the design of the housing may allow the housing to disintegrate or degrade over the predetermined period of time. This can contribute to mitigating adverse effects of device administration to an animal, and could also ensure that an animal can be treated with multiple bolus e.g. a second bolus is administered at or towards, or after, the end of the predetermined period of time.

In embodiments of the invention, the thickness of the housing may be selected to contribute to the rate of release of the inhibiting agent. For instance, the inventors have identified that thickness of the housing can affect the rate of release of the inhibiting agent from the bolus.

In these embodiments, a relatively thicker housing will have a relatively slower release rate than a relatively thinner housing.

In a preferred embodiment, the housing may have a thickness of at least 1 mm.

In yet a further preferred embodiment, the housing may have a thickness of less than 3 mm.

In yet another preferred embodiment, the housing may have a thickness of between 1.5 to 2 mm, or between 0.5 to 2 mm.

In a particularly preferred embodiment, the housing has a thickness of 1 mm.

The thickness of the housing may be particularly important for achieving a desired controlled release for the inhibiting agent in embodiments such as those where the core is entirely encapsulated by the housing. This should become clearer from the following discussion.

In an embodiment, the dimensions of the cavity may vary along the length of the housing.

In a preferred embodiment, the cavity includes at least two regions which have a different cross-sectional area to each other e.g. a first region having a first cross-sectional area and a second area having a second cross-sectional area.

In a particularly preferred embodiment, the first region has a relatively smaller cross-sectional area and the second region has a relatively larger cross-sectional area.

In yet a further preferred embodiment, the first region may be located closer to the open end than the second region.

Having a cavity with regions having different cross-sectional areas to each other may facilitate more controlled release of the inhibiting agent(s) to better meet an animal's requirements. For instance, a relatively smaller across-sectional area can be provided closer to the open end to deliver a relatively smaller dose of the inhibiting agent(s), whereas the relatively larger cross-sectional area may be provided closer to the distal end; this may be useful where the dose of the inhibiting agent needs to increase over time e.g. due to animal growth.

It should also be understood that the reverse arrangement may be provided e.g. the relatively larger cross-sectional area is provided closer to the open end and the relatively smaller cross-sectional area may be provided closer to the distal end. This arrangement may be useful where an initially higher dose of the inhibiting agent(s) is desired, to be followed by a subsequently smaller dose at a subsequent time. For instance, this arrangement may be used where an animal has a high demand for the inhibiting agent e.g. at periods of relatively high feed intake and energy requirements such as during milking but to be followed by a period of relatively low feed intake e.g. during the dry-period.

Furthermore, it should be understood that the cross-sectional area of the cavity may increase gradually and continuously from the first region to the second region e.g. there is no defined "step" between the first region and the second region.

In other embodiments, the housing may include a third region having a third-cross sectional area. This may be further used to control the dose of the inhibiting agent(s) to the animal. Accordingly, the foregoing should not be seen as limiting on the scope of the present technology.

In an embodiment, the thickness of a wall of the housing may vary along the length of the housing. In such an embodiment, the wall thickness at or towards one end of the housing may be thicker than at the distal end. For example, the thickness of the wall at or towards the open end may be thinner in size than that of the distal end.

This arrangement may be particularly beneficial in assisting to control release of the inhibiting agent(s) over time. For instance, the relatively thinner wall(s) will degrade relatively quicker than the relatively thicker wall(s). This structure can be used to control the rate of degradation of the housing along its length. For instance, it may be used to ensure that the open end is the only site at which fluids in the rumen are able to come into contact with, and erode, the core.

In preferred embodiments, the housing made be made from a material through which the inhibiting agent can migrate in use e.g. by a mass diffusion process.

In a preferred embodiment, the housing may be made from at least one plastic material. For instance, the housing may be made from a degradable plastic or material that degrades over time in the rumen.

In a particularly preferred embodiment the housing may be made from a material selected from the list of one or more of poly lactic acid (PLA), poly glycolic acid (PGA), poly lactic glycolic acid (PLGA), polypropylene, Polycaprolactone (PCL), poly(d-lactic acid) (PDLA), Polybutylene succinate (PBS), Polybutylene adipate terephthalate (PBAT), SLA polymer, ABS, or a combination thereof. In a particularly preferred embodiment, the housing comprises PLA and PBS.

The material for the housing may comprise PLA, PBAT and/or PBS in different ratios as shown in examples 1 through 7 in the table below (% by weight):

|   | PLA (w %) | PBS (w %) | PBAT (w %) |
|---|-----------|-----------|------------|
| 1 | 100       |           |            |
| 2 | 70        | 30        |            |
| 3 | 40        | 60        |            |
| 4 | 20        | 80        |            |
| 5 | 70        |           | 30         |
| 6 | 40        |           | 60         |
| 7 | 20        |           | 80         |

In a particularly preferred embodiment, the material for the housing comprises PLA and PBS in a weight ratio ranging from 100:0 to 40:60 PLA:PBS.

In a particularly preferred embodiment, the housing comprises PLA and PBS in a weight ratio ranging from 100:0 to 40:60 PLA:PBS, wherein the housing has a thickness of between 0,4 and 1.5 mm.

In a further embodiment the core of the bolus of the invention is covered by multiple housings which are arranged concentrically (e.g. akin to an onion). Such multiple housings (e.g. 2 or 3 or even more housings) have the advantage that the bolus will be degraded (e.g. by abrasion)

in the rumen less quickly. As a consequence, the haloform in the core will last longer in the rumen and methane production is reduced for a longer time. In embodiments comprising multiple housings the material and thickness of the housing can be as described herein for other embodiments. In preferred embodiments a bolus of the invention comprises at least two housing layers, one outer housing and one inner housing, the material of each housing comprising a biodegradable polymer and preferably a biodegradable polymer selected from the group consisting of polylactic acid (PLA), polybutylene succinate (PBS), polybutylene adipate terephthalate (PBAT) and combinations thereof.

In addition, the housing may also be made from a non-biodegradable material, such as EVA, silicons, acrylates etc. As a result, the discussion herein should not be seen as limiting on the scope of the present invention.

In addition, the material from which the housing is made may include one or more other compounds e.g. plasticisers, hardeners, colourants etc.

However, in alternate embodiments, the housing may be made from one or more non-adsorbent materials i.e. a material into which, or through which, the inhibiting agent does not migrate. Using a non-absorbent material for the housing can assist with controlling the rate of release of the inhibiting agent(s) in certain embodiments such as an open-ended bolus. For instance, in these embodiments, the concentration of the inhibiting agent(s) in the core is not decreased by their absorption into the housing material.

In some embodiments, the bolus may include a barrier layer. In these embodiments, the barrier layer may be positioned between at least a portion of the core and the housing. For instance, the barrier layer can minimise, or completely prevent, contact between the portion of the core and the housing. This can be useful to prevent dissolution of the inhibiting agent (or other compounds) to better control the release of the inhibiting agent(s) and improve the stability of the device. This could be particularly useful where the inhibiting agent(s) has a high solubility in the material(s) from which the housing is made.

Alternatively, in an embodiment where the barrier layer is provided between only a portion of the core and the housing, it may reduce but not completely prevent, migration of the inhibiting agent into the housing. In effect, the barrier layer reduces the contact area between the core and the housing and so therefore may reduce the release rate of inhibiting agent than were the barrier layer not provided.

Alternatively, the bolus may not include a barrier layer. This configuration may be useful where the inhibiting agent(s) has a relatively low solubility in the material from which the housing is constructed. It may also be useful where the composition of the housing and/or carrier are selected to control the release rate e.g. the rate of diffusion of the inhibiting agent through the housing.

In another embodiment, the bolus may be adapted to have rates of dissolution of the core and the housing which provide substantially uniform dissolution of both components in the rumen over time.

In one embodiment, the cavity in the housing may provide a reservoir configured to receive an amount of the inhibiting agent(s). For instance, the reservoir may be a closed cavity in the housing which can receive and hold the amount of the inhibiting agent.

In one embodiment, the bolus may include a dispensing mechanism.

In one embodiment, the carrier may have a relatively higher affinity for the inhibiting agent compared to the affinity of the housing for the inhibiting agent. As discussed elsewhere in this document, this may be achieved by the relative polarity of the substances forming the carrier and the housing, and matching these materials appropriately to the inhibiting agent.

In another embodiment, the housing may be formed from a substance having a Shore D hardness of at least 40. In such an embodiment, it is believed that having a housing with a lower Shore D hardness of 40 to result in a bolus that is too soft, which could hinder administration of the bolus to an animal or lead to it being otherwise damaged or prematurely degraded before the full amount of inhibiting agent is administered.

In a further embodiment, the housing may be formed from a substance having a Shore D hardness of less than 80.

In another embodiment, the housing may be configured to facilitate the controlled release the inhibiting agent from the core. Without being limited to a specific mechanism, the inventors postulate that the inhibiting agent may be released through the housing by the mechanism of mass diffusion.

In a further embodiment, the invention provides a bolus for administration to a ruminant animal, wherein said bolus comprises:
  a core, wherein the core comprises a haloform (preferably bromoform) mixed with a carrier; and
  a housing which covers at least a portion of the core or preferably the entire core; wherein, the bolus is configured to release the haloform.

In a further embodiment, the invention provides a bolus for administration to a ruminant animal, wherein said bolus comprises:
  a core, wherein the core comprises a haloform (preferably bromoform) mixed with a carrier; and
  a housing which covers at least a portion of the core or the entire core;
  wherein, the bolus is configured to release the haloform; and wherein the carrier comprises wax, preferably castor wax, paraffin wax or a mixture thereof.

In a further embodiment, the invention provides a bolus for administration to a ruminant animal, wherein said bolus comprises:
  a core, wherein the core comprises a haloform (preferably bromoform) mixed with a carrier; and
  a housing which covers at least a portion of the core or preferably the entire core; wherein, the bolus is configured to release the haloform; and wherein the carrier comprises wax, preferably castor wax, paraffin wax or a mixture thereof; and wherein the housing comprises a biodegradable polymer and preferably a biodegradable polymer selected from the group consisting of polylactic acid (PLA), polybutylene succinate (PBS), polybutylene adipate terephthalate (PBAT) and combinations thereof.

In a further embodiment, the invention provides a bolus for administration to a ruminant animal, wherein said bolus comprises:
  a core, wherein the core comprises a haloform (preferably bromoform) mixed with a carrier; and
  a housing which covers at least a portion of the core or preferably the entire core; wherein, the bolus is configured to release the haloform; and wherein the carrier comprises wax, preferably castor wax, paraffin wax or a mixture thereof; and wherein the housing has a layer thickness of between 0,4 and 1.5 mm.

In a further embodiment, the invention provides a bolus for administration to a ruminant animal, wherein said bolus comprises:

a core, wherein the core comprises a haloform (preferably bromoform) mixed with a carrier; and a housing which covers at least a portion of the core or preferably the entire core; wherein, the bolus is configured to release the haloform; and wherein the carrier comprises wax, preferably castor wax, paraffin wax or a mixture thereof; and wherein the housing comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the housing has a layer thickness of between 0,4 and 1.5 mm.

In a further embodiment, the invention provides a bolus for administration to a ruminant animal, wherein said bolus comprises:

a core, wherein the core comprises a haloform (preferably bromoform) mixed with a carrier; and a housing which covers at least a portion of the core or preferably the entire core; wherein, the bolus is configured to release the haloform; and wherein the carrier comprises wax, preferably castor wax, paraffin wax or a mixture thereof; and wherein the housing comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the housing has a layer thickness of less than 2 mm.

In a further embodiment, the invention provides a bolus for administration to a ruminant animal, wherein said bolus comprises:

a core, wherein the core comprises a haloform (preferably bromoform) mixed with a carrier; and a housing which covers at least a portion of the core or the entire core;

wherein, the bolus is configured to release the haloform; and wherein the core further comprises at least one metal piece (such as metal pellets and/or a metal rod), preferably the metal being steel or zinc. The advantage of this embodiment is that the bolus density is increased, and the bolus is less likely of being regurgitated by the animal. Preferably the bolus of the invention further comprises a densifier, and preferably said densifier comprises at least one piece of metal, preferably the densifier is provided in the core.

In a further embodiment, the invention provides a bolus for administration to a ruminant animal, wherein said bolus comprises:

a core, wherein the core comprises a haloform (preferably bromoform) mixed with a carrier; and a housing which covers at least a portion of the core or preferably the entire core; wherein, the bolus is configured to release the haloform; and wherein the carrier comprises wax, preferably castor wax, paraffin wax or a mixture thereof; and wherein the housing comprises polylactic acid (PLA); and wherein the housing preferably has a layer thickness of less than 2 mm.

In a further aspect, the invention provides a delayed release dosage form for administration to a ruminant animal, wherein said delayed release dosage form comprises: a core, wherein the core comprises a haloform (preferably bromoform); and a coating which covers at least a portion of the core or preferably the entire core; wherein the delayed release dosage form is configured to release the haloform.

In a further embodiment, the invention provides a delayed release dosage form for administration to a ruminant animal, wherein said delayed release dosage form comprises: a core, wherein the core comprises a haloform (preferably bromoform); and a coating which covers art least a portion of the core or preferably the entire core; wherein the delayed release dosage form is configured to release the haloform; and wherein the core further comprises wax, preferably castor wax, paraffin wax or a mixture thereof.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating comprises a biodegradable polymer and preferably a biodegradable polymer selected from the group consisting of polylactic acid (PLA), polybutylene succinate (PBS), polybutylene adipate terephthalate (PBAT) and combinations thereof.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating has a layer thickness of between 0,4 and 1.5 mm.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the coating has a layer thickness of between 0,4 and 1.5 mm.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the coating has a layer thickness of less than 2 mm.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers the core; wherein the delayed release dosage form is configured to release the haloform; and wherein the core further comprises at least one metal piece (such as metal pellets and/or a metal rod), preferably the metal being steel or zinc. An advantage of this embodiment is that the delayed release dosage form density is increased, and the delayed release dosage form is less likely of being regurgitated by the animal.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers a portion of the core or the entire core; wherein the delayed release dosage form is configured to release the haloform; and wherein the carrier comprises wax, preferably castor wax, paraffin wax or a mixture thereof; and wherein the coating comprises polylactic acid (PLA); and wherein the coating preferably has a layer thickness of less than 2 mm. Experiments have shown that coating layer thickness less than 2 mm are preferably because this thickness lets the haloform permeate from the core material outwardly in an optimal rate.

In a delayed release dosage form or a bolus of the invention preferably less than 50% of the haloform comprised in the core is released over a time of three months. In a preferred embodiment of the delayed release dosage form or a bolus of the invention the core comprises at least 100 grams of haloform. The core of the bolus or of the delayed release dosage form of the invention preferably comprises between 30 wt % and 70 wt % of haloform (preferably bromoform).

At present, it is understood that controlled release of the inhibiting agent through the housing may be influenced by a number of factors. For example, the affinity of the inhibiting agent for the carrier may play a role in the diffusion of the inhibiting agent through the housing. It is understood that more polar carriers or carriers containing a high degree of polar functional groups will have a higher affinity with the inhibiting agent than less polar carriers or carriers with a lower degree of functional groups.

The relative affinity of the materials forming the housing and the core for the inhibiting agent may also affect controlled release of the inhibiting agent from the core. For example, having a housing with a relatively lower affinity for the inhibiting agent compared to the affinity of the carrier for the inhibiting agent, could be a factor in controlling the rate of release of the inhibiting agent from the core. These aspects of the invention should become clearer from the description herein.

Throughout the present specification, reference to the term "release mechanism" should be understood as meaning an arrangement to release a predetermined amount of the inhibiting agent (s) over time. For instance, the release mechanism may comprise a valve arrangement which can release an amount of the inhibiting agent(s) via an outlet. Alternatively, the release mechanism may be a syringe-type mechanism having a plunger and actuator; over time, the actuator moves the plunger in the reservoir to drive the inhibiting agent(s) out of the reservoir.

Also, the following items are according to the invention:

Item 1 provides a bolus for administration to a ruminant animal, wherein said bolus is configured to release an effective amount of at least one inhibiting agent.

Item 2 provides the bolus of any one of item 1, wherein the at least one inhibiting agent is a methane inhibitor.

Item 3 provides the bolus of items 1 or 2, wherein the at least one inhibiting agent is a haloform selected from chloroform, bromoform, iodoform, or combinations thereof.

Item 4 relates to the bolus of any one of items 1-3, wherein the at least one inhibiting agent is bromoform.

Item 5 relates to the bolus of any one of items 1-4, wherein the bolus includes a core which comprises an amount of the inhibiting agent.

Item 6 provides the bolus of item 5, wherein the core includes a carrier mixed with the inhibiting agent.

Item 7 relates to the bolus of item 6, wherein the carrier is a waxy substance, selected from the bee's wax, paraffin wax, PEG4000, Carnauba, Candellila, Jojoba, or Lanolin or a combination thereof.

Item 8 relates to the bolus of any one of items 5-7, wherein the core has a melting point greater than 37° C.

Item 9 relates to the bolus of any one of items 5-8, wherein the bolus includes a housing to receive and hold the core.

Item 10 relates to the bolus of item 9, wherein the housing includes a cavity which can receive and hold the core.

Item 11 relates to the bolus of item 9 or 10, wherein the housing includes an opening to facilitate, in use, exposure of the core to fluid in the rumen of the ruminant.

Item 12 relates to the bolus of item 10 or 11, wherein the cavity includes a first region which has a first cross-sectional area and a second region which has a second cross-sectional area, and wherein the first cross-sectional area and the second cross-sectional area are different to each other to facilitate controlled release of the inhibiting agent from the core.

Item 13 relates to the bolus of any one of items 9-12, wherein the housing is configured to degrade over a predetermined period of time.

Item 14 relates to the bolus of any one of items 9-13, wherein housing is made from one or more non-adsorbent materials selected from the following: poly lactic acid (PLA), poly glycolic acid (PGA), poly lactic glycolic acid (PLGA), polypropylene, SLA polymer, PBS, or a combination thereof.

Item 15 relates to the bolus of any one of items 9-14, further comprising a barrier layer between at least a portion of the housing and the core to isolate the portion of the housing and the core from contact with each other.

Item 16 relates to the bolus of any one of items 1 to 15, wherein the bolus is adapted to release a dose of approximately 0.1 g to 0.5 g of the inhibiting agent per day into the ruminant animal's rumen.

Item 17 relates to the bolus of any one of items 1 to 16, wherein the bolus is adapted to release the inhibiting agent over a period of at least six months.

Item 18 relates to the bolus of any one of items 1 to 17, wherein the bolus is adapted to release the inhibiting agent within two years.

Item 19 provides a method for reducing emission of gas from a ruminant animal, the method comprising the step of administering to said ruminant animal the bolus of any one of items 1-18.

Item 20 provides a method for reducing methane production in a ruminant animal, the method comprising the step of administering to said ruminant animal the bolus as item in any one of items 1-18.

Item 21 provides the use of a methane inhibitor and a carrier in a bolus for reducing methane production in a ruminant animal.

Item 22 provides the use of a methane inhibitor and a carrier in a bolus for reducing methane emission from a ruminant animal.

Item 23 provides the use of a haloform in the manufacture of a bolus for reducing the emission of one or more greenhouse gases ("GHGs") from a ruminant animal.

Item 24 provides a method of manufacture of a bolus of any one of items 1 to 18, comprising:
a. forming a housing which has a cavity;
b. forming a core which includes the inhibiting agent;
c. transferring the core to the cavity.

Item 25 relates to the method of item 24, wherein the step of forming the core involves mixing a carrier material with the inhibiting agent.

Item 26 provides the method of item 25, wherein the step of forming the core involves heating the carrier material to melt the carrier material prior to mixing the carrier material with the inhibiting agent to create a mixture.

Item 27 relates to the method of any one of items 24 to 26, wherein the step of transferring the core to the cavity involves pouring the mixture into the cavity.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which:

FIG. 16A shows tensile specimen shrinkage from injection moulding.

The term "bromet" as used in the figures refers to a bromoform containing bolus.

BRIEF DESCRIPTION OF PREFERRED
EMBODIMENTS OF THE INVENTION

The present invention relates to devices and methods to deliver substances to animals, particularly hydrophobic substances to animals. In preferred forms, the substance is an inhibiting agent such as a methane inhibitor. The present invention is exemplified with reference to a preferred embodiment. However, this should not be seen as limiting on the scope of the invention. One skilled in the art would understand how to apply the teachings herein to devices for delivery of other substances to animals.

Figure 1A:
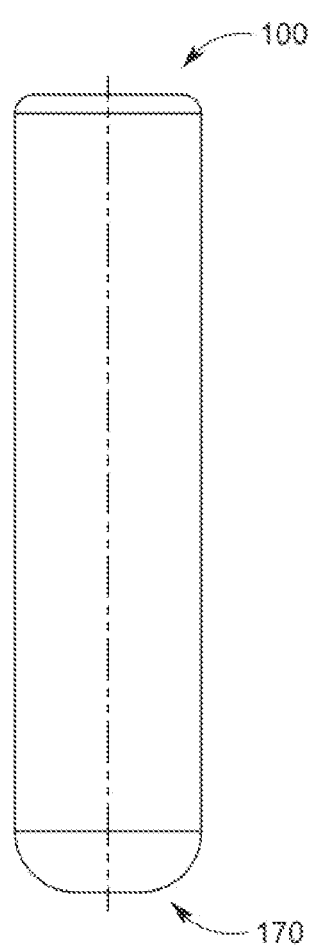
FIG. 1A is a front view of a bolus in accordance with one aspect of the invention.
Figure 1B:
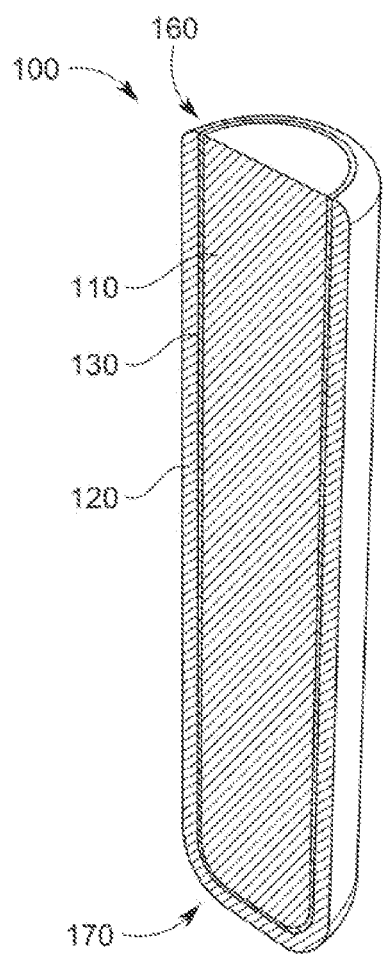
FIG. 1B is a perspective cross sectional view of the bolus of FIG. 1A.

Referring first to FIGS. 1A and 1B, there is provided a bolus (100). The bolus (100) is configured to reduce or eliminate release of one or more greenhouse gases ("GHGs") from a ruminant animal. For instance, the bolus (100) may reduce or eliminate production of GHGs by the ruminant animal, and therefore reduce the gases which are released by the animal.

In addition, or in the alternative, the bolus (100) may improve animal production by preventing the conversion of feed into one or more GHGs from a ruminant animal.

The bolus (100) includes a core (110) and a housing (120).

In some embodiments, the bolus (100) also includes a barrier layer (130). The barrier layer (130) is configured to separate the core (110) from the housing (120).

The housing (120) is generally cylindrical and has an open end indicated generally as (60), and a rounded, closed end (170). The open end (160) can allow fluids in the ruminant animal's rumen to contact the core (110).

Further aspects of the bolus (100) should become clearer from the following discussion.

Core

The core (110) includes at least one inhibiting agent, which can be optionally mixed with a suitable carrier(s). Particularly preferred carriers include PEG4000, PEG400, natural and synthetic waxes, fatty acids, fatty alcohols, fatty amines, phospholipids-lecithin, and adsorbents, and combinations thereof.

Suitable waxes include beeswax, paraffin, castor wax, Carnauba wax, Candellila wax, Jojoba wax, and Lanolin.

In addition, minerals such as zeolite, bentonite, kaolin, activated carbon or a combination thereof may also be suitably mixed with the inhibiting agent. It is also possible to include other compounds such a zinc (i.e. in powdered form) or zinc oxide.

Alternatively, the core (110) may include a concentrated (substantially pure) form of the inhibiting agent.

In a preferred embodiment, the inhibiting agent is a methane inhibiting agent. Particularly preferred forms include haloforms e.g. halomethanes such as bromoform ($CHBr_3$)—as is discussed in more detail below.

It should be appreciated by a person skilled in the art that other carriers may be selected or used depending on the application. It is envisioned that certain carriers can be selected in order to provide a desired release profile for the inhibiting agent, or alternatively provide the desired physical properties of the core material—density or volume etc.

In preferred embodiments the carrier used in the present invention is a natural waxy substance, with a preferred melting point between 50-90° C., or more preferably 60-80° C.

It was found by the inventors that having a carrier with this melting point range allowed for melting of the carrier and mixing with the inhibiting agent(s) to form a homogenous core (110), and to subsequently solidify at room temperature.

A particularly preferred carrier is a mixture containing castor wax with one or more of paraffin wax, beeswax, and carnauba wax. Further preferred, the carrier is a mixture containing castor wax and paraffin wax.

It should be appreciated that the ratio of carrier to inhibiting agent may be chosen to optimise the function of the bolus (100) e.g. to suit the desired release profile for the inhibiting agent(s).

When formed, the core (comprising both the carrier and inhibiting agent(s)) preferably has a melting point of at least 45° C. Having this minimum melting point will assist with ensuring that the core (110) does not melt when the bolus (100) has been administered to the ruminant animal. In addition, it will assist to ensure that the bolus (100) is unlikely to melt on inadvertent exposure to elevated temperatures e.g. those temperatures that could reasonably be experienced during transport and/or storage.

It should be appreciated that the range of melting points for the core (110) may be adapted by varying the ratio of inhibiting agent(s) to carrier forming the core (110).

A preferred ratio of inhibiting agent to carrier may include substantially 80:20 w/w % to substantially 50:50 w/w %, or preferably substantially 70:30 w/w % to substantially 60:40 w/w %, or more preferably substantially 66:33 w/w %.

Inhibiting Agent(s)

In a preferred embodiment, the inhibiting agent is one or more methane inhibiting compounds.

Suitable methane inhibitors include haloforms such as bromoform, chloroform, iodoform and combinations thereof. It is envisioned that any methane inhibitor that is suitable for internal administration to a ruminant animal may be used with the present invention.

The inventors have surprisingly found that bromoform is a particularly well suited for use in a bolus (100) according to the present invention. Accordingly, reference herein will be made to the inhibiting agent(s) as bromoform. However, this should not be seen as limiting on the scope of the present invention as alternatives are also envisaged as being within the scope of the present invention.

Bromoform is reactive and has a short half-life in animals (0.8 hrs in rats, 1.2 hours in mice, US Dept of Health, 2003). It is a liquid at room temperature and is denser than water. Previous trials demonstrated no residues in meat and tissue from slaughtered steers, after 48 hour with holding period (Kinley et al. Mitigating the carbon footprint and improving productivity of ruminant livestock agriculture using a red seaweed, *Journal of Cleaner Production* 259 (2020) 120836), and no significant increase in the level in milk (Roque et al. Inclusion of *Asparagopsis armata* in lactating dairy cows' diet reduces enteric methane emission by over 50 percent; *Journal of Cleaner Production* 234 (2019) 132-138).

Bromoform has a relatively high efficacy e.g. effect per administered dose. This enables sufficient quantities to be provided in a core (110) to manufacture a bolus (100) which can deliver controlled release of the inhibiting agent over an extended term.

Additionally, bromoform also has a relatively high density. This can assist with achieving a higher retention of the bolus (100) in the rumen, as the density of the bolus can be optimised to promote the bolus (100) sinking to the ventral part of the rumen, rather than floating.

The above points notwithstanding, there is a prevailing concern about using bromoform in animals. The compound is thought to have adverse effects such as being carcinogenic at certain exposure levels.

In addition, there are technical challenges which exist when bromoform is administered to animals. These include the volatility of the substance, and its ability to dissolve substances which could be used for its delivery. Furthermore, achieving a precise (and relatively low) dose rate over a period of time is a challenge.

Housing

The housing (120) includes a cavity (not numbered in the Figures) which is sized and dimensioned to receive the core (110). The housing (120) forms the external structure of the bolus (100).

The housing (120) is configured to provide structural integrity for the bolus (100) but yet is also adapted to degrade over time. Degradation of the housing (120) can facilitate release of the inhibiting agent over the predetermined period of time.

The housing (120) is preferably non-toxic and resists erosion in the rumen of the ruminant for a sufficient period of time to facilitate release of inhibiting agent from the core (110) at the desired rate. It should be appreciated by the person skilled in the art that the dissolution rate of the housing (120) and the core (110) can be configured to allow the controlled release of the inhibiting agent in the ruminant animal's rumen.

Preferably, the housing (120) is composed of a biodegradable, non-absorbent material, or a material which is otherwise compatible with waste disposal in slaughter facilities. It should be appreciated that any material that is suitable for internal administration to a ruminant animal with the desired dissolution rates can be used with the present invention.

In a preferred embodiment, the housing (120) is preferably selected from a biodegradable material, particularly preferred biodegradable materials include polymers such as polylactic acid (PLA), polyglycolic acid (PGA), polylactic glycolic acid (PLGA), polypropylene, SLA polymer, PBS and combinations thereof. In a particularly preferred embodiment, the housing (120) is made of a material comprising PLA and PBAT.

In a preferred embodiment the housing (120) is composed of PLA. PLA is available in three forms, D-, L- and a racemic mixture of both D and L. All three types of PLA may be used in the housing (120) of the present invention.

In a preferred form, PLA is preferred as it degrades into lactic acid and is commonly used as medical implants. Depending on the type of PLA used, PLA breaks down inside the body within six months to two years.

It should be appreciated by the person skilled in the art that other suitable biodegradable materials can be used as the housing (120).

In an optional embodiment, further fillers, binders, surfactants, active agents and/or absorbents may be included in the bolus of the present invention.

As can be seen in FIGS. 1A and 1B, the bolus (100) has a substantially cylindrical form. The housing (120) includes a smooth external surface to assist with ingestion of the bolus (100) by the ruminant animal.

It should be appreciated by the person skilled in the art that the size, thickness and/or dimensions of the bolus (100), including the core (110), barrier layer (130) if provided, and the housing (120) can be adjusted depending on the dose of inhibiting agent to be delivered to the ruminant, without departing from the spirit and scope of the invention. For example, a smaller size bolus (100) can be adapted for use in smaller ruminant animals such as sheep or goats, while a larger sized bolus (100) can be used in larger ruminant animals such as cattle. A bolus for a large animal, such as cattle, may have the dimensions of 13 cm length, 3.4 cm diameter and 257 gm in weight (Throughout the application "gm" refers to gram). A bolus for a relatively small animal, such as a sheep, may have the dimensions of 8.5 cm length, 2 cm diameter and 60 gms in weight. Alternatively, a smaller bolus may be administered to a relatively larger ruminant animal, such as cattle; such a relatively smaller bolus may have the dimensions of 3.4-3.8 cm length and 2.6-3.0 cm diameter.

In it also envisaged that multiple smaller boluses may be used in combination. In preferred embodiments, the bolus and the delayed dosage form of the invention has a length of at least 5 cm and most preferably a length of at least 10 cm, preferably 10.3 cm. In preferred embodiments, the bolus and the delayed dosage form of the invention has a diameter of at least 2 cm, preferably 3.4 cm and a length of at least 10 cm, preferably 10.3 cm. Preferably, the bolus and the delayed dosage form of the invention has a weight of at between 100 and 300 grams.

Additionally, the housing (120) may also be configured to control the release rates of the core (110) and/or degradation of the bolus (100). For example, the internal cross-sectional area of the cavity may be adapted to control the amount of the core (110) present in the bolus (100). In such an embodiment, the internal volume of the cavity may be adapted to increase in size from the open end (160) to the closed end (170). This may be useful for increasing the amount of inhibiting agent(s) over time. This may account for animal growth where feed intake. of the animal increases.

Additionally, or alternatively, the cross-sectional thickness of the wall(s) forming the housing (120) may increase along the length of the housing (120). For instance, the wall(s) may be a thicker at one end of the housing (120) than the other. In such an embodiment, the thickness of the wall at the open end (160) may be thinner in size than towards closed end (170). This can assist with providing controlled dissolution of the core formulation from the bolus.

Barrier Layer

The barrier layer (130) is an optional component of the bolus (100) of the present invention and may be included to provide additional stability to the bolus (100). The barrier layer (130) can be configured to partially or completely prevent contact between the core (110) and the housing (120). The barrier layer (130) is preferably selected from a waxy material, epoxy or a silicon material.

It should be appreciated by the person skilled in the art, the barrier (130) layer may be selected dependent on the desired application and/or release profile. For example, where further control of the release rate of the inhibiting agent is desired, choosing a barrier layer (130) material, shape and configuration can facilitate obtaining the desired release profile.

Exemplified Composition

As an exemplified embodiment, the bolus may comprise a core enclosed by a housing. The bolus may be about 13 cm in length and about 3.4 cm in diameter with an approximate weight of 257 gm.

The housing may be made of PLA (3052D, 3001D, 3251D, L130, etc), e.g. by injection moulding, and have a thickness of 1 mm.

The matrix of the core may be made of a blend of castor wax and paraffin wax in a ratio of 50:50 (by weight). This matrix may contain bromoform as an inhibiting agent in a concentration of about 50% (by weight).

Method of Treatment

The bolus (100) is delivered orally into the rumen of the ruminant animal to be treated, entering the rumen via the oesophagus. In the rumen, stomach fluids (and other matter such as plant fibre mat) act to eventually erode or dissolve the core (110) to release the inhibiting agent over time. However, for the duration of the treatment period, the housing is substantially intact.

The open end (160) allows stomach fluids and fibrous matter to come into contact with the core (110). In addition, it assists to control release of the core (110) therefrom to the rumen.

The core (110) and the housing (120) are designed to facilitate release of the inhibiting agent over a period of time for which an animal is to be treated according to a method disclosed herein.

The bolus (100) is adapted to release the inhibiting agent over a period of at least six months, preferably 12 months, and potentially up to two years.

Preferably, the release rates of the inhibiting agent may be calculated based on the weight of the ruminant animal to be treated and the type of inhibiting agent used. As such, it will be appreciated that the desired release rates may vary from animal to animal. Typically, the desired release rates may be calculated on an amount of inhibiting agent/weight of animal. Alternatively, the desired release rates may also be calculated based on the amount of feed consumed by the animal. Particularly preferred release rates for bromoform include from approximately 0.1-approximately 0.5 g/day, and more preferably approximately 0.2 g/day.

Additionally, it should be appreciated by a person skilled in the art that a ruminant animal can be treated by multiple boluses (100) according to the present invention in order to achieve a preferred dosage of the inhibiting agent. This can allow a bolus (100) to be manufactured which has a concentration and total load of the inhibiting agent. Multiple of those bolus (100) can be administered to an animal concurrently or sequentially. This will allow the desired dosage to be provided to the animal. This can be particularly beneficial to allow the bolus (100) to be used with animals requiring different doses of inhibiting agent e.g. larger or smaller animals, or to compensate for natural growth over time.

The bolus (100) is adapted to deliver a dose of inhibiting agent directly into the rumen of the animal. For instance, bromoform may be released at a rate at which it can effectively reduce or eliminate methane production during digestion. That will reduce the emission of greenhouse gases by the animal and therefore reduce the environmental impacts of agriculture.

In addition, the bolus (100) may improve the ruminant's conversion of feed for animal production. For example, by reducing methane production during digestion, it is believed that this may lead to more efficient utilization of ingested feed, and result in improved growth and weight gain, or other production such as milk production. In addition, the compositions for the core and synergistic effects arising from the combination of carrier and inhibiting agent(s) may enable the provision of a slow-release, long term delivery device to improve animal productivity and/or reduce emission of greenhouse gases.

First Alternate Housing Embodiment

Figure 2A:
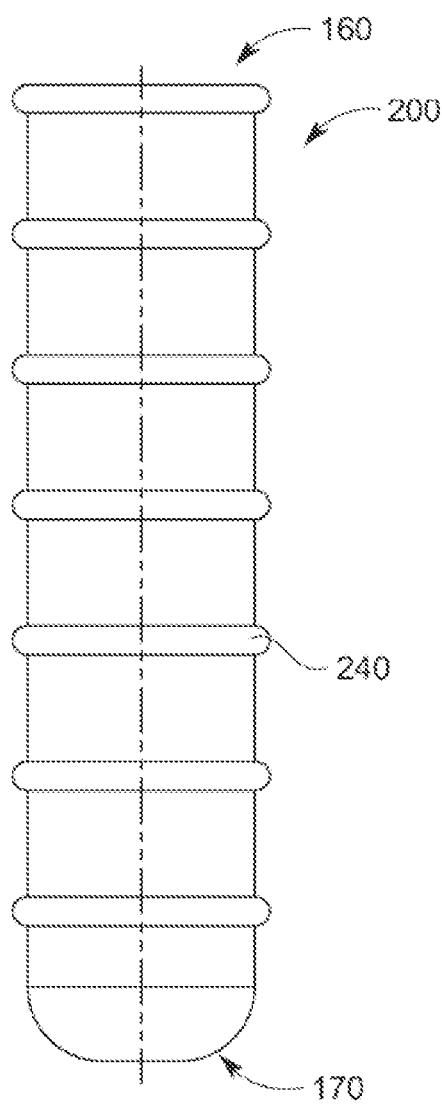
FIG. 2A is a front view of an alternative embodiment of a bolus in accordance with a further aspect of the invention.
Figure 2B:
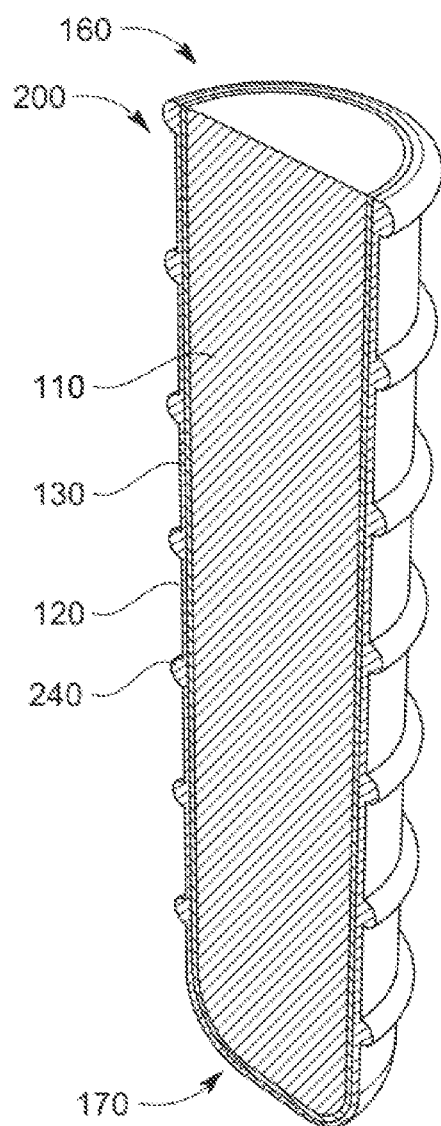
FIG. 2B is a perspective cross sectional view of the bolus of FIG. 2A.

Referring now to FIG. 2A-2B which shows an alternative embodiment of a bolus (200) according to an embodiment of the invention.

Aspects of the bolus (200) are similar to those of the bolus (100), and therefore like references refer to like components.

A series of ribs (240) are provided along an external surface of the housing (120). The ribs (240) may provide additional structural strength to the bolus (200), and can assist to prevent it rupturing if the core (110) were to swell. Additionally, or alternatively, the (240) ribs may also assist the administration of the bolus (200) to the ruminant animal.

As illustrated, the ribs (240) are provided as a series of concentric "hoops". However, the ribs (240) could be a series of parallel or non-parallel ribs (not illustrated) which extend along the length of the bolus (200)

Second Alternate Housing Embodiment

Figure 3A:
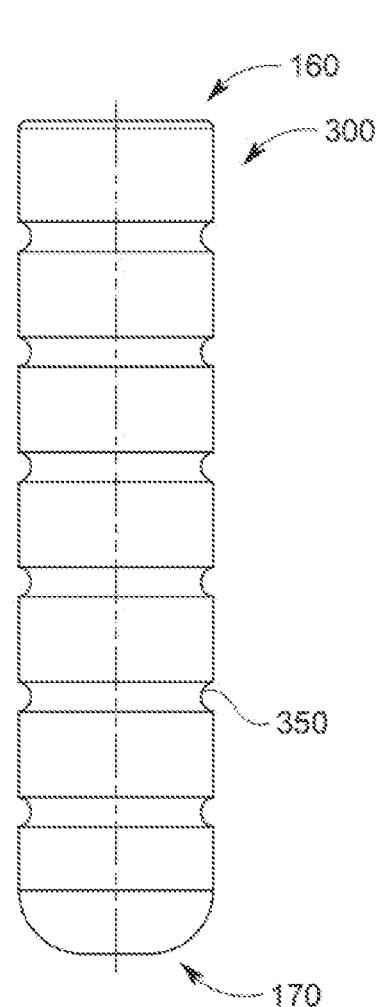
FIG. 3A is a front view of an alternative embodiment of a bolus in accordance with a further aspect of the invention.
Figure 3B:
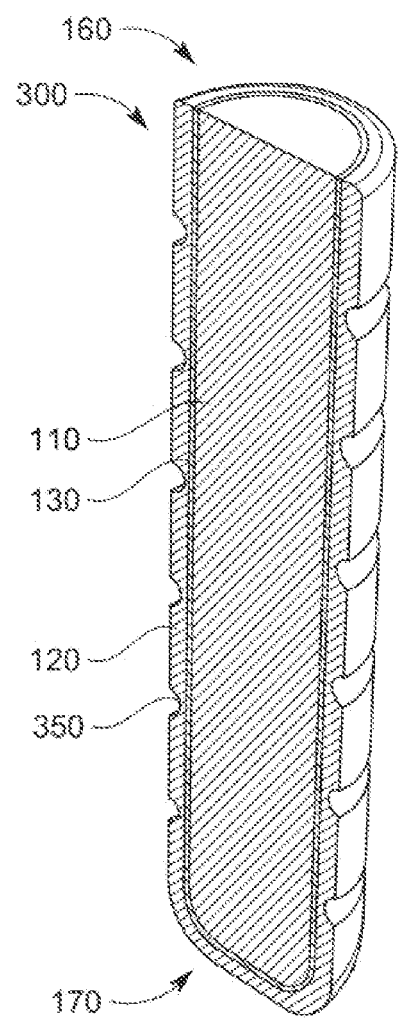
FIG. 3B is a perspective cross sectional view of the bolus of FIG. 3A.

Referring now to FIGS. 3A-3B which show an alternative embodiment of a bolus (300) according to an embodiment of the invention.

Aspects of the bolus (300) are similar to those of the bolus (100) described above, and therefore like references refer to like components.

The bolus (300) includes additional features on the external surface of the housing (120), including depressions or grooves (350).

The grooves (350) may promote portions of the housing (120) breaking away as it degrades. This can be used to further control the release profile for the inhibiting agent.

Third Alternate Housing Embodiment

Figure 4A:
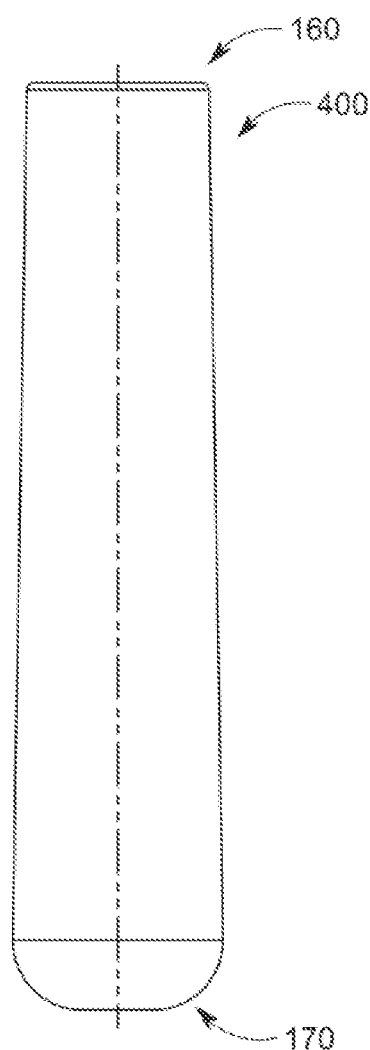
FIG. 4A is a front view of an alternative embodiment of a bolus in accordance with a further aspect of the invention.
Figure 4B:
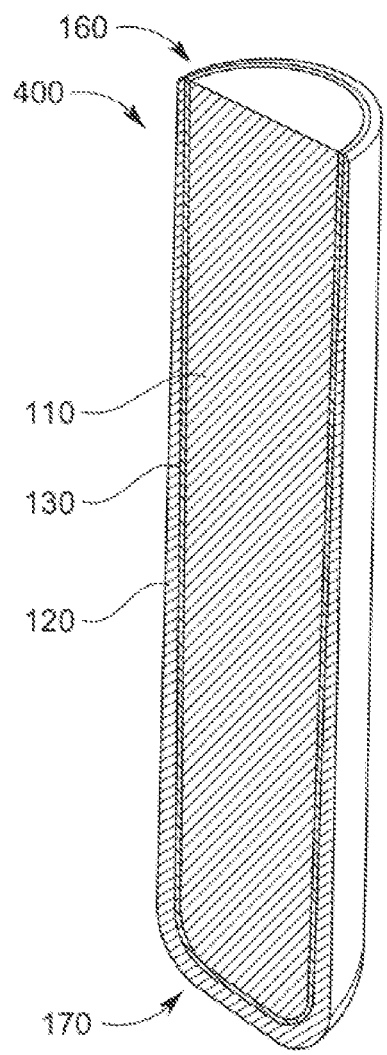
FIG. 4B is a perspective cross sectional view of the bolus of FIG. 4A.

Referring now to FIGS. 4A-4B which show an alternative embodiment of a bolus (400) according to an embodiment of the invention.

Aspects of the bolus (400) are similar to those of the bolus (100) described above, and therefore like references refer to like components.

The bolus (400) includes a housing (120) which has a cavity (not illustrated in the Figures) that is configured to receive and hold the core (110).

The housing (120) tapers along its length. For instance, the distance between the external surfaces of distal sides of the housing (120) increases along the length of the bolus (400). For instance, as is indicated in FIG. 4A, the width (X) is less than the width (Y).

Alternatively, the bolus (400) may have side walls of substantially constant thickness, but which are structured and orientated to define a taper for the bolus (400).

This configuration may allow for better controlled degradation of the core (110) and thereby provide additional control for release of the inhibiting agent.

Fourth Alternate Housing Embodiment

Figure 5:
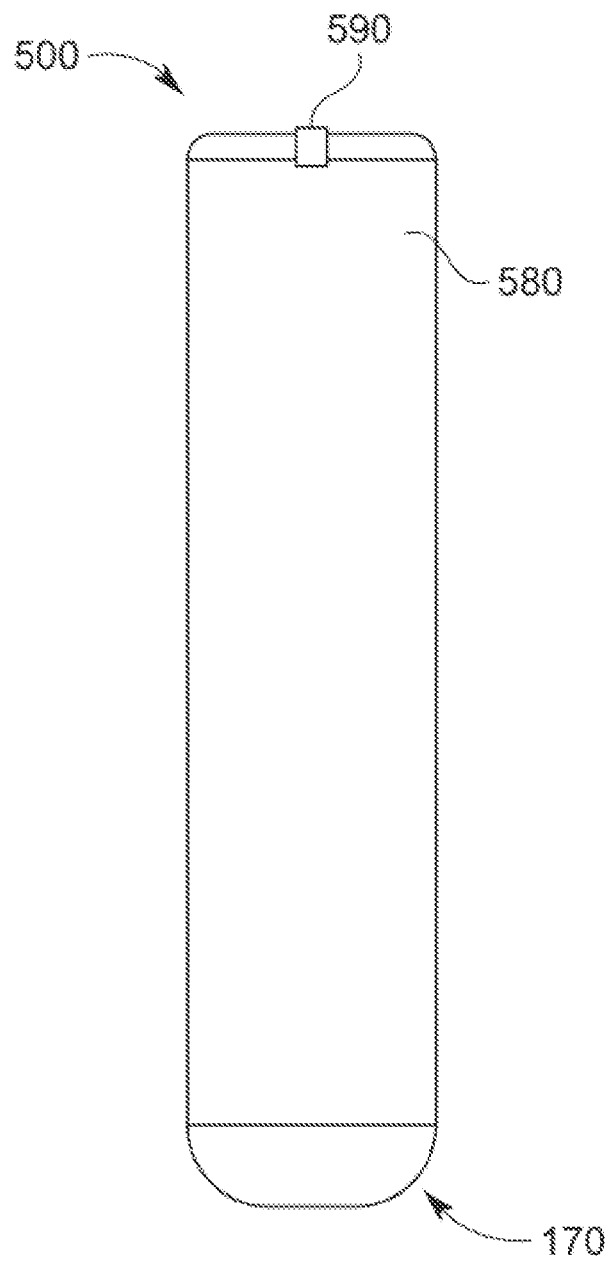
FIG. 5 is a front view of an alternative embodiment of a bolus in accordance with a further aspect of the invention.

Referring now to FIG. 5A which shows an alternative embodiment of a bolus (500) according to an embodiment of the invention.

Aspects of the bolus (500) are similar to those described above, and therefore like references refer to like components.

The bolus (500) includes a reservoir (580) adapted to hold a relatively concentrated form of the inhibiting agent e.g. bromoform in a substantially pure, liquid form.

The bolus (500) includes a dispensing mechanism which is configured to dispense predetermined dose(s) of the inhibiting agent from the reservoir (580).

In the illustrated embodiment, the dispensing mechanism is a pump (590) in communication with a valve. At predetermined times, the pump (590) dispenses a dose of the inhibiting agent via the valve (590), to release the inhibiting agent to the rumen to which the bolus (500) has been administered.

The dispensing mechanism may be configured to release a consistent e.g. the same, amount of the inhibiting agent at defined intervals.

Alternatively, the dispensing mechanism may be configured to vary the amount of inhibiting agent released at different times. This may be useful to enable the bolus (500) to provide an effective amount of inhibiting agent which accounts for growth of the animal. In addition, or alternatively, it may compensate for other factors changes e.g. seasonal variations in methane production which would necessitate a higher dose of inhibiting agent.

In a further embodiment, the bolus (500) may include sensors (not shown). For example, temperature sensors may be included within the bolus (500). Additionally, or alternatively, other sensors may also be included in the bolus, such as locomotion and pH. The addition of such sensors can provide valuable information on the feed intake of the animal and assess whether the amount of inhibiting agent is sufficient for the animal.

Fifth Alternate Housing Embodiment

Figure 6A:
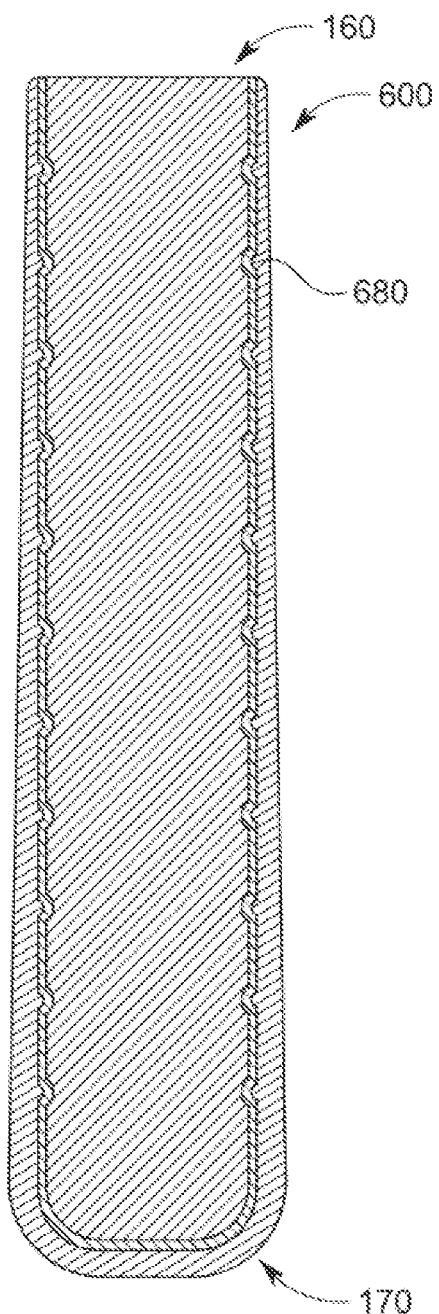
FIG. 6A is a front cross sectional-view of an alternative embodiment of a bolus in accordance with a further aspect of the invention.
Figure 6B:
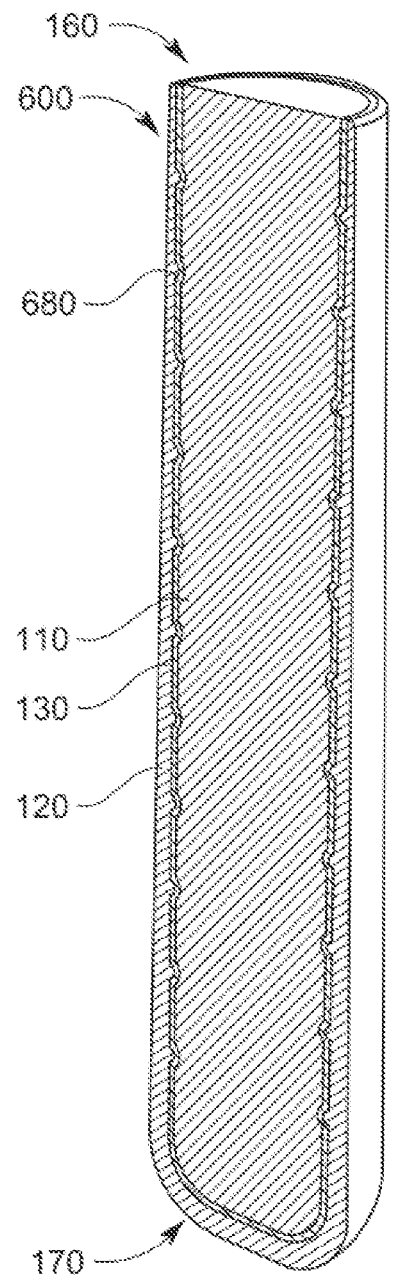
FIG. 6B is a perspective cross-sectional view of the bolus of FIG. 6A.

Referring now to FIGS. 6A and 6B which show an alternative embodiment of a bolus (600) according to an embodiment of the invention.

The bolus (600) can be adapted to include additional features within the cavity of the housing, such as grooves or ribs (680) formed on an inner wall of the housing (120) that defines the cavity.

Aspects of the bolus (600) are similar to those of the bolus (100), and therefore like references refer to like components.

A series of ribs (680) are provided along an internal surface of the housing (120). The ribs (680) may provide additional structural strength to the bolus (600), and/or provide additional means to retain the contents of the core formulation within the cavity of the housing. Additionally, or alternatively, the (680) ribs may also assist with the retention of the core within the housing. Further, the ribs may also provide controlled dissolution of the core formation from the bolus (600) to the ruminant animal.

In one embodiment, the external surface of the housing will remain smooth or uniform.

Sixth Alternate Housing Embodiment

Referring now to FIGS. 15A to 15D which show a further embodiment of a bolus (700) according to an aspect of the present invention. Dimensions of the bolus in the Figure are provided in mm. Preferably, the bolus has a length of 13 cm, a diameter of 3.4 cm and preferably a weight of about 250 gm.

The bolus (700) can be adapted to include additional features with the internal reinforcing structure on the housing.

Aspects of the bolus (700) are similar to those of the bolus (100), and therefore like references refer to like components.

The bolus (700) includes at least one reinforcing rib (710) located inside a cavity (unnumbered) defined by the housing structure. A cap (720) may also be provided e.g. releasably attached to the bolus (700) to close the open end of the bolus (700). Attachment may be provided by a friction fit arrangement, or a screw thread arrangement in which corresponding screw threads on the housing and cap engage each other. Alternatively, the cap may be attached to the housing by an adhesive or other mechanical fastener.

The reinforcing rib(s) (720) may improve the structural integrity of the bolus (700) and assist it to hold its shape.

Method of Manufacture

Figure 7:
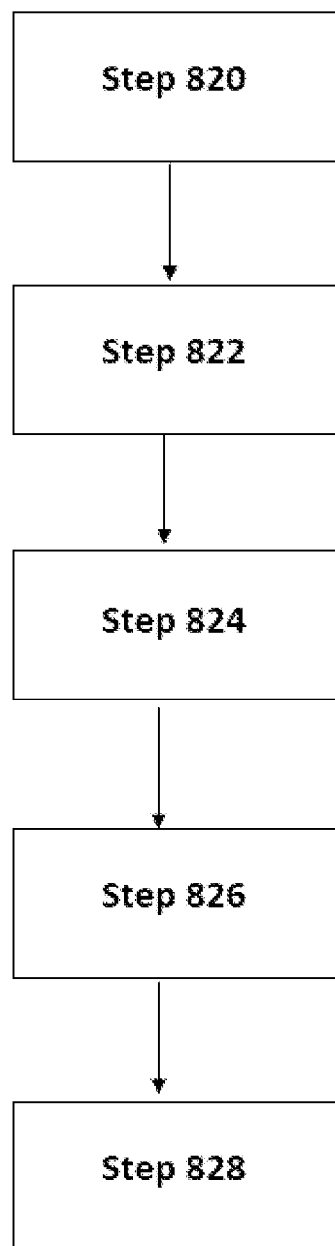
FIG. 7 is a flow diagram showing representative steps in a method of manufacturing a bolus in according with an aspect of the invention.

Referring now to FIG. 7, which is a flow chart showing representative steps in a method of manufacturing (800) a bolus e.g. (100), (200), (300), (400), according to the present invention.

In general terms, the method includes the step (810) of forming the housing (120) and the step (820) forming a core (110).

Housing

Forming the housing (120) may occur using any technique as should be known to one skilled in the art. For instance, a suitable material may be extruded into a desired shape defining a cavity. Alternatively, an additive layering manufacturing process could also be used to build the housing shape defining a cavity. It is also envisaged that a moulding process could be used e.g. a sacrificial moulding or injection moulding process, 3D printing or hot melt extrusion processes may be used.

Core

In step 820, the core (110) is manufactured.

Step 820 may include one or more of the following steps:

Step 822 which involves melting a carrier material to provide a melted carrier material;

Step 824 which involves adding the inhibiting agent(s) to the melted carrier material;

Step 826—which involves mixing the inhibiting agent and the melted carrier material to create a substantially homogenous mixture.

Step 828 which involves forming the substantially homogeneous mixture into a desired shape.

It should be understood that the substantially homogenous mixture contains the inhibiting agent(s) at a concentration sufficient to achieve the desired release profile for the inhibiting agent on administration of the device to a ruminant animal. The concentration can be varied according to the type of ruminant animal to be treated, the shape and dimensions of the device, or the desired release profile to be achieved.

It should be understood that the step of forming the substantially homogeneous mixture into a desired shape may involve providing the mixture to a mould. In a particularly preferred form, the substantially homogeneous mixture is added (poured) into a cavity in a housing (120) manufactured at step 810.

Alternatively, the mould may be a separate component which receives the substantially homogenous mixture. In these embodiments, once the desired shape has been formed, the core can subsequently be provided to a cavity in a housing (120).

The method also includes the step of allowing the substantially homogeneous mixture to cool. As it cools, the carrier material hardens and assumes a shape according to the shape of the mould or housing into which it has been provided.

Example Formulations

The following cores were formulated for use in the bolus of the present invention.

|  | Amount (w/w %) | | | | | | | |
| --- | --- | --- | --- | --- | --- | --- | --- | --- |
| Example | 1 | 2 | 3 | 4 | 5 | 6 | 7 | 8 |
| Bromoform | 20 | 20 | 20 | 25 | 12.5 | 8.3 | 25 | 12.5 |
| Paraffin | 80 | 30 | 30 | 50 | 50 | 50 | — | — |
| Beeswax | — | 50 | — | — | — | — | 50 | 50 |
| PEG 4000 | — | — | 50 | — | — | — | — | — |
| PEG 400 | — | — | — | — | — | — | — | — |
| AC | — | — | — | 25 | — | — | 25 | — |
| Kaolin | — | — | — | — | 37.5 | — | — | 37.5 |
| Zeolite | — | — | — | — | — | 41.7 | — | — |

|  | Amount (w/w %) | | | | | | |
| --- | --- | --- | --- | --- | --- | --- | --- |
| Example | 9 | 10 | 11 | 12 | 13 | 14 | 15 |
| Bromoform | 8.3 | 25 | 12.5 | 8.3 | 20 | 33 | 33 |
| Paraffin | — | — | — | — | — | 66 | — |
| Beeswax | 50 | — | — | — | — | — | 66 |
| PEG 4000 | — | 50 | 50 | 50 | 50 | — | — |
| PEG 400 | — | — | — | — | 30 | — | — |
| AC | — | 25 | — | — | — | — | — |

-continued

| | | | | | | |
|---|---|---|---|---|---|---|
| Kaolin | — | — | 37.5 | — | — | — |
| Zeolite | 41.7 | — | — | 41.7 | — | — |

The following additional high bromoform content cores were also formulated for use in the bolus of the present invention.

| | Amount (w/w %) | | | | | | | | | |
|---|---|---|---|---|---|---|---|---|---|---|
| Example | 16 | 17 | 18 | 19 | 20 | 21 | 22 | 23 | 24 | 25 | 26 |
| Bromoform | 33 | 50 | 67 | 75 | 33 | 50 | 67 | 75 | 33 | 50 | 67 |
| Beeswax | 67 | 50 | 33 | 25 | — | — | — | — | — | — | — |
| Paraffin wax | — | — | — | — | 67 | 50 | 33 | 25 | — | — | — |
| Carnauba wax | — | — | — | — | — | — | — | — | 67 | 50 | 33 |
| Castor Wax | — | — | — | — | — | — | — | — | — | — | — |
| Activated Carbon | — | — | — | — | — | — | — | — | — | — | — |
| Bentonite | — | — | — | — | — | — | — | — | — | — | — |
| Zinc Oxide | — | — | — | — | — | — | — | — | — | — | — |

| | Amount (w/w %) | | | | | | | | |
|---|---|---|---|---|---|---|---|---|---|
| Example | 27 | 28 | 29 | 30 | 31 | 32 | 33 | 34 | 35 | 36 |
| Bromoform | 75 | 33 | 50 | 67 | 75 | 50 | 50 | 50 | 50 | 50 |
| Beeswax | — | — | — | — | — | — | — | — | 25 | 25 |
| Paraffin wax | — | — | — | — | — | — | — | — | — | — |
| Carnauba wax | — | — | — | — | — | — | — | — | — | 25 |
| Castor Wax | 25 | 67 | 50 | 33 | 25 | — | — | — | 25 | — |
| Activated Carbon | — | — | — | — | — | 50 | — | — | — | — |
| Bentonite | — | — | — | — | — | — | 50 | — | — | — |
| Zinc Oxide | — | — | — | — | — | — | — | 50 | — | — |

Validation

Example 1: Release/Diffusion Study

Trials with 2 mm thick 3D printed large capped boluses (LCB2) filled with 66.7% (by weight) bromoform and 33.3% (by weight) beeswax in the RME (Rumen Emulator) (RME trial 2) were conducted to determine the diffusion rate of bromoform from the bolus.

Bolus Design

A reinforced bolus as shown in FIG. 15 was used for this study. It includes an internal reinforcing structure as well as ribs spread apart to support the wall, an upper part was adapted for the attaching a cap. The bolus with reinforcing was found to be more robust and held its shape better than without reinforcing when the molten bromoform/beeswax mixture was poured in and cooled, as well as a more physically robust bolus for the trial.

Method

Materials

Bromoform (reagent grade, Sigma Aldrich, 96% bromoform, 4% ethanol), beeswax (food grade, NZ Beeswax, MP 65° C.) and zinc oxide from Native Ingredients NZ.

Bolus Manufacture

The boluses were drawn in Solidworks, converted to .stl files, opened in FlashPrint to create the print jobs. The boluses were printed in three parts (case, internal structure and cap) on FlashForge Creator Pro 3D printers using E-Sun PLA+ at 100% fill, standard resolution, first layer height 0.27 mm, layer height 0.18 mm, 2 perimeter shells, 3 top solid layers, 3 bottom solid layers, fill pattern hexagon, print speed 60 mm/s, extruder temperature 200° C. and plate temperature 50° C.

Eight LRB boluses were prepared at 67% (by weight) bromoform, eight LRB boluses were prepared at 75% (by weight) bromoform, and six LCB2 boluses with no bromoform (controls). Ingredients are listed below (Table 1). All ingredients were weighed in beakers on a calibrated 4dp electronic balance. Bromoform solutions were covered with parafilm to prevent evaporation. Ingredients were prepared by melting pre-weighed beeswax and zinc oxide in beakers at 100° C. (Thermoprism Oven), letting the mixture cool to 80° C., adding the bromoform and the mixture kept well mixed to prevent the zinc oxide from settling out, before pouring into the boluses. Caps were press fitted and soldered to seal the bolus.

TABLE 1

Preferred compositions for the shortened reinforced boluses

| | | Per bolus | | | Total | | |
|---|---|---|---|---|---|---|---|
| Type | Quantity | Zinc Oxide (g) | Beeswax (g) | Bromoform (g) | Zinc Oxide (g) | Beeswax (g) | Bromoform (g) |
| LCB2 | 6 | 28.0 | 80.4 | 0.0 | 168.0 | 482.7 | 0.0 |
| LRB1 | 8 | 28.0 | 47.3 | 96.1 | 224.0 | 378.8 | 769.0 |
| LRB1 | 8 | 28.0 | 39.7 | 119.0 | 224.0 | 317.3 | 952.0 |
| Total | | | | | 616.0 | 1178.7 | 1721.0 |

The boluses were placed in 500 ml polypropylene bottles with approximately 380 ml 0.02M phosphate buffer (Merck) in distilled water, prepared in 2 L or greater batches, adjusted to pH 6.5 using 1M HCl (Merck) and a pre-calibrated pH meter (using pH 4, 7, and 10 pH buffers). The bottles were sealed and placed in the incubator at 40° C. 10 ml samples were collected and the entire solution changed every 24 hours.

10 ml samples was collected using a 10 ml autopipette in 15 ml Falcon tubes. 1 g of sodium chloride was added to each Falcon tube. For GC-MS analysis, 1 ml of ethyl acetate (analytical grade, Merck) was added to each Falcon tube. When GC-FID was used 2 ml of ethyl acetate was added to each Falcon tube. The Falcon tubes were capped, well mixed using a Vortex, and centrifuged at 4000 rpm for 15 minutes. For GC-MS analysis, all the ethyl acetate was recovered using a graduated glass syringe and the volumes noted.

For GC-FID analysis, 0.5 ml of ethyl acetate was recovered. For GC-FID analysis, 200 ul of sample was injected using an autosampler, and analysed using a ZB5HT 30 m capillary column using a temperature ramp of 30-300° C. over 20 minutes, at 5 ml/min nitrogen gas flow, in splitless mode. Bromoform had a retention time of 7.5 minutes. Peak areas were compared to calibration standards made up in ethylene acetate to determine the mass of bromoform (mg). This was divided by the volume injected to obtain the concentration of bromoform in the ethyl acetate (mg/L). The concentration in ethyl acetate was multiplied by the total volume of ethyl acetate added to the sample and divided by the recovery to obtain mass of bromoform in the sample. This was then divided by the volume of sample collected to obtain a concentration in the solution, which was then multiplied by the volume of solution in the Shott bottle to obtain mass transferred from the bolus to the solution. Bromoform recovery from solution was checked using standard solutions made up to different concentrations of bromoform and was typically 43%. GC-FID performance was checked for each run of ten samples using a calibration sample as a reference.

Results

Figure 8:
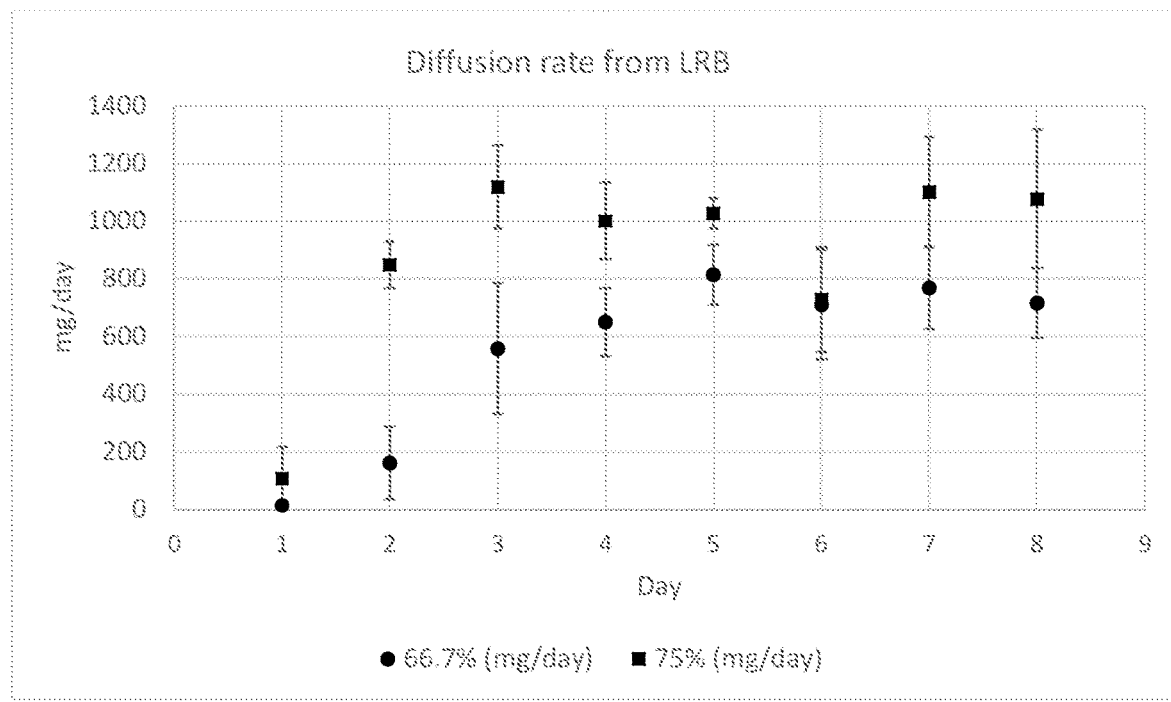
FIG. 8 is a graph showing the daily diffusion/release rate of bromoform from bolus in the media.

A lower diffusion rate followed by a rapid increase in diffusion rate was observed for both boluses (FIG. 8). The 67% bolus had a lag time of 4-5 days before reaching its maximum diffusion rate, whereas the 75% reached maximum diffusion rate with 3 days.

The rate of diffusion was higher for the 75% bolus at 1010 mg/day when compared to 66.7% which was 730 mg/day. This was a surprising, but also good result (as it means that a single bolus could be used to dose 700 kg bulls and achieve methane reduction), as the predicted diffusion rates for an LCB1 bolus for 67% bromoform was 300 mg/day and 462 mg/day for an LCB1 bolus with 75% bromoform. The expectation for the LRB boluses was a lower diffusion rate because it had a reduced surface area at 1 mm thick (about 71% that of a LCB1 bolus) (Table 2). In theory the LRB bolus should only be delivering 220 mg/day for 67% bromoform and 344 mg/day for 75%.

TABLE 2

Expected diffusion rate for an LRB bolus from the different parts of the bolus.

| Bits of the bolus | Quantity | Length (cm) | Width (cm) | Diameter (cm) | Area (cm2) | Tickness (mm) | Espected rates (mg/cm2/day) | |
|---|---|---|---|---|---|---|---|---|
| | | | | | | | 0.67 | 0.75 |
| Cap | 1 | 1.7 | | 3.4 | 27.2 | 2 | 0.357 | 0.49 |
| Ribs | 4 | 0.3 | | 3.4 | 12.8 | 3 | 0.082 | 0.086 |
| Active diffusion area | 3 | 3 | | 3.4 | 96.1 | 1 | 1.999 | 3.042 |
| Eye | 1 | 3.0 | 1.2 | | 3.5 | 3 | 0.082 | 0.085 |
| Curved bit | | | | | 12.2 | 1 | 1.939 | 3.042 |
| | | | | | | | Total [mg/day] | |
| | | | | | | | Actual [mg/day] | |
| | | | | | | | Factor out | |

| | Exposed wax (mg/cm2/day) | | Total (mg/day) | | Contribution (%) | |
|---|---|---|---|---|---|---|
| Bits of the bolus | 0.67 | 0.75 | 0.67 | 0.75 | 0.67 | 0.75 |
| Cap | 85.0 | 116.2 | 9.7 | 13.3 | 4.4 | 3.9 |
| Ribs | 85.0 | 116.2 | 1.1 | 1.1 | 0.5 | 0.3 |
| Active diffusion area | 85.0 | 116.2 | 186.4 | 292.4 | 84.3 | 84.9 |
| Eye | 85.0 | 116.2 | 0.3 | 0.3 | 0.1 | 0.1 |
| Curved bit | 85.0 | 116.2 | 23.7 | 37.3 | 10.7 | 10.5 |
| | | | 221.2 | 344.4 | | Total |
| | | | 731 | 1064 | | Grand total |
| | | | 3.30 | 3.09 | | |

TABLE 3

Calculation of the porous area to achieve the same diffusion rate as what was measured from the LRB boluses using previously determined diffusion rates.

| | 67% bromoform | | | 75% bromoform | | |
|---|---|---|---|---|---|---|
| Proportion area open | mg/day through open area | mg/day through closed area | Proportion area open | mg/day through open area | mg/day through closed area |
| 0.01 | 23.2 | 9.6 | 0.01 | 31.6 | 13.2 |
| 0 | 0.0 | 1.1 | 0 | 0.0 | 1.1 |
| 0.06 | 449.4 | 176.1 | 0.06 | 614.1 | 276.4 |
| 0 | 0.0 | 0.3 | 0 | 0.0 | 0.3 |
| 0.06 | 57.3 | 22.4 | 0.06 | 78.2 | 35.2 |
| Total (mg/day) | 529.8 | 209.6 | | 724.0 | 326.2 |
| Grand total (mg/day) | | 739.4 | | | 1050.2 |

Figure 9:
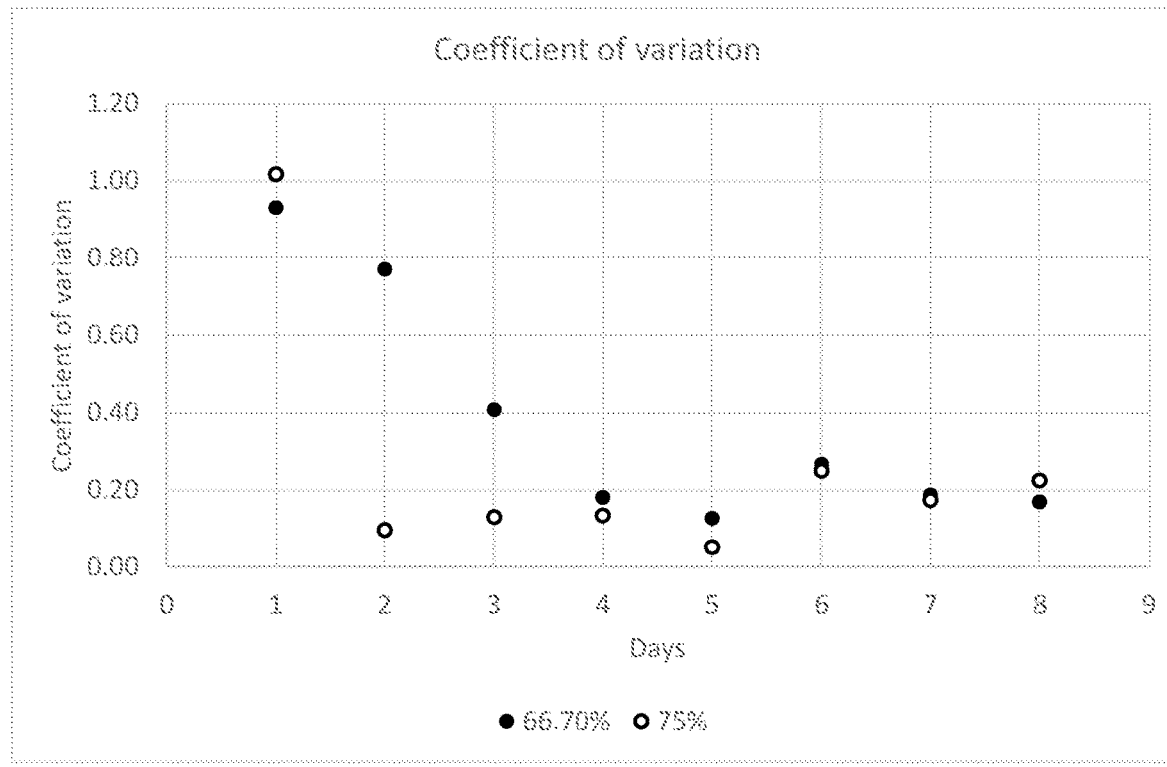
FIG. 9 is a graph showing variability in the diffusion results.
Figure 10:
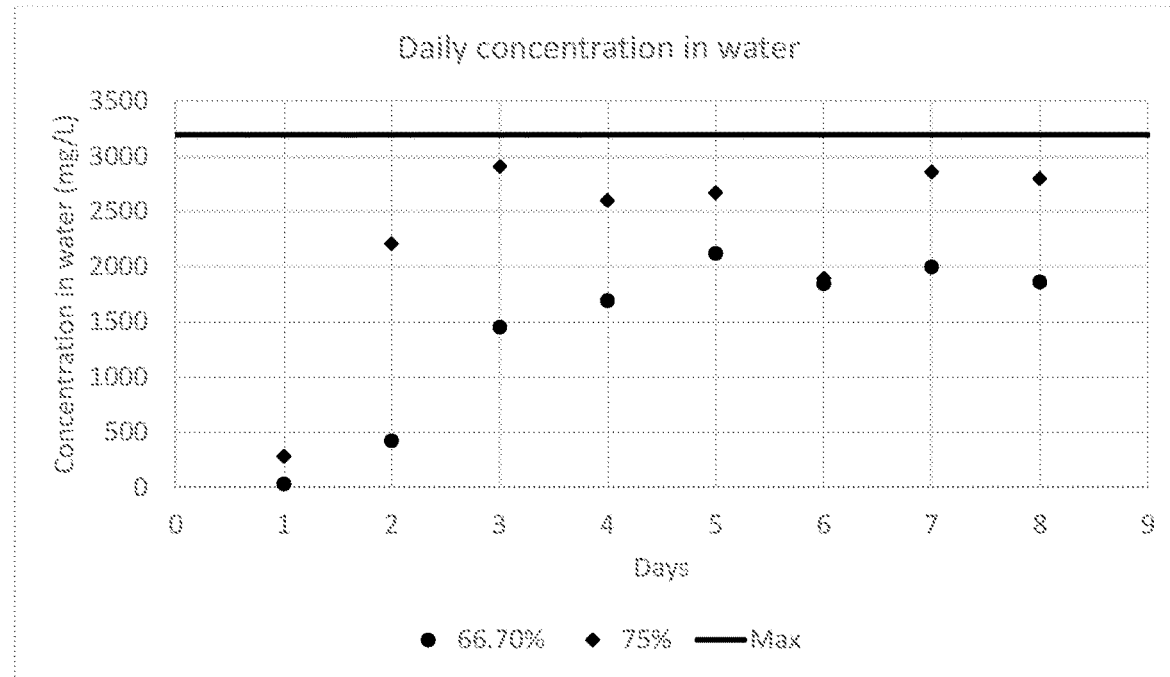
FIG. 10 is a graph showing the concentration of Bromoform in a diffusion media over time.

Variability in diffusion data was high initially with a coefficient of variation of around 1, and this decreased to between 0.05-0.22, as the boluses reached their maximum diffusion rates (FIG. 9). The 75% bolus settled within 2 days, while the 67% bolus settled within 4 days.

Figure 11:
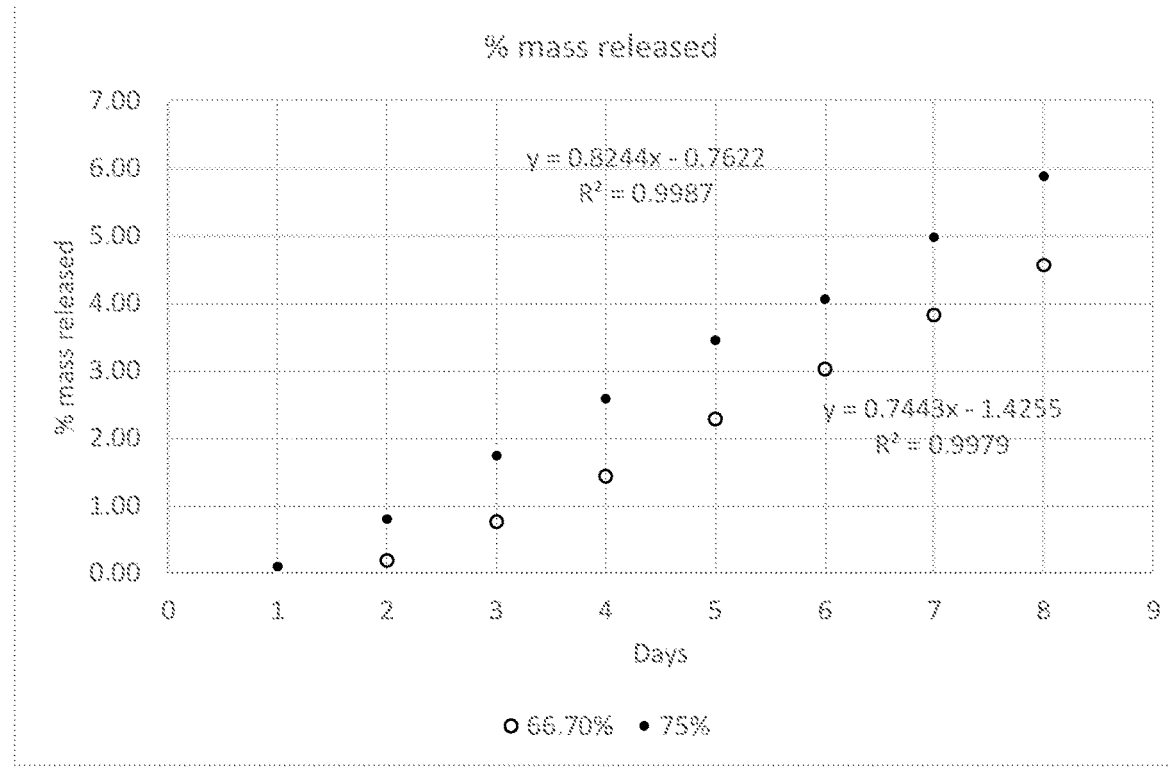
FIG. 11 is a graph showing the mass of Bromoform released (%) over time.

A zero-order release was observed for both boluses indicating the rate of release was independent of concentration of bromoform in the bolus (FIG. 11).

Conclusion

The rate of diffusion for LRB boluses was 1010 mg/day for the 75% bolus, and 730 mg/day for the 66.7% bolus which was higher than predicted from the previous diffusion studies.

The concentration of bromoform in the media for the 75% bolus, is close to the solubility limit of bromoform in water (3.2 g/L), therefore diffusion rates may be higher than measured in this study.

Example 2: Release Testing of Carriers

Release testing of various carriers was undertaken for this study.
Method
Materials Bromoform (reagent grade, Sigma Aldrich, 96% bromoform, 4% ethanol), ruminal fluid (Dairy NZ Trial), paraffin waxes (MPs 46-48, 55 and 65° C., Sigma Aldrich), castor wax (Lotus Oils), carnauba wax (PureNature NZ), zinc oxide (PureNature NZ).
pH and Buffer Capacity of Ruminal Fluid The rumen fluid collected from Dairy NZ was thawed and centrifuged before analysing for pH and buffer capacity. A volume of 10 ml of Rumen fluid received from each cow was taken and titrated against 0.05 N NaOH with continuous pH monitoring. Volume of NaOH to change the pH by a unit was recorded.
Release and Testing of Various Carriers Small capped boluses were prepared as described in example 1 above.

Paraffin waxes, beeswax, carnauba wax and castor wax were mixed with bromoform to 33%, 50%, 67% and 75% by weight bromoform. The mixes were placed in the following:
  a. Paraffin waxes: 2 mm thick small capped boluses and 15 ml falcon tube;
  b. Castor, carnauba and beeswaxes: 1, 2, and 3 mm small capped boluses and 15 ml falcon tubes.

These were placed in 500 ml polypropylene bottles with 400 ml 0.02M phosphate buffer (Merck) in distilled water, prepared in 2 L or greater batches, adjusted to pH 6.5 using 1M HCl (Merck) and a pre-calibrated pH meter (using pH 4, 7, and 10 pH buffers). The bottles were sealed and placed in the incubator at 40° C. 10 ml samples were collected and the entire solution changed every 2 days (Monday, Wednesday, Friday), except for the weekend hours.

Samples were analysed by GC-MS and GC-FID as described in example 1 above.
Results
pH and Buffer Capacity The mean pH and the buffer capacity were 6.9±0.2 (n=4) and 7.47±1.4 mMol/L/delta pH (n=4) respectively. While there has been published literatures for pH values for ruminal fluid, no data for buffer capacity is available. The buffer capacities obtained for ruminal fluid indicates that the rumen environment is resilient as it is 5-6-fold higher than that of phosphate buffer saline. We found the pH of phosphate buffer in diffusion experiment remained stable even around 3 mg/ml of Bromofrom concentration (Report No BR 2021-01, FIG. 4). Given the volume of rumen fluid 91 L, the maximum concentration of bromoform at extreme condition of complete bolus rupture would reach around 1.09 mg/ml, which is lower than observed earlier in PBS. Therefore, with this concentration and given the strong buffer capacity of Rumen fluid, there is a less possibility of pH drop in the event of abrupt bolus rupture.

Release Testing of Carriers

Figure 12:
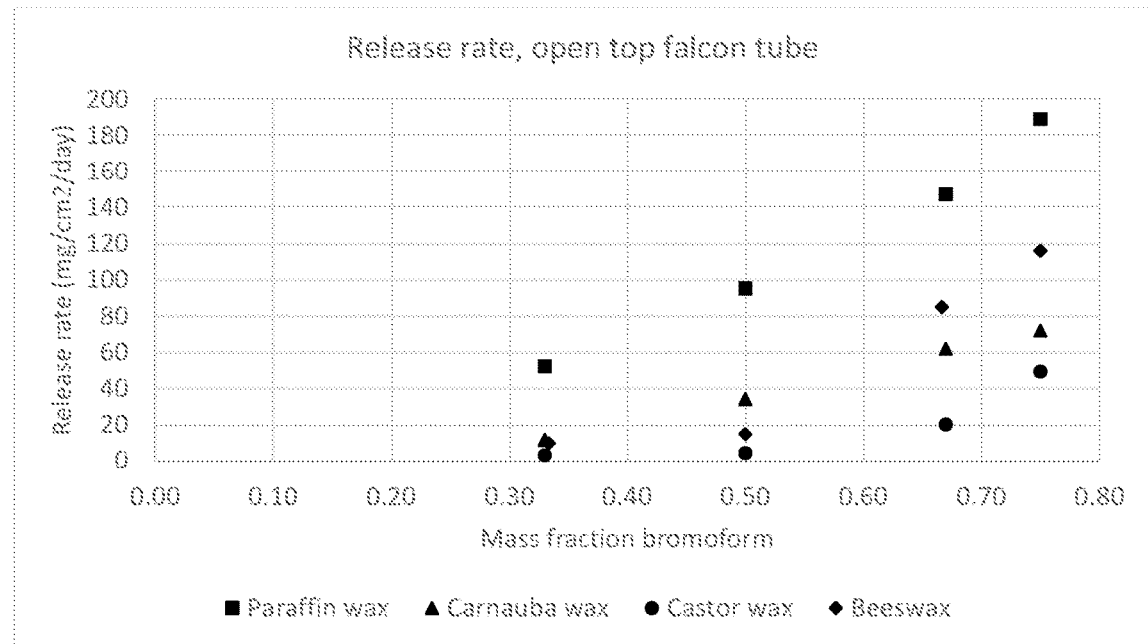
FIG. 12 is a graph showing the release rates of bromoform from different carriers in open top falcon tubes.

Paraffin wax had the highest release rate at 190 mg/cm2/day, followed by beeswax, carnauba and castor wax (FIG. 12). Carnauba and castor wax seem better options for the carrier as the release rate is 50 to 40% less compared to beeswax.

Figure 13A:
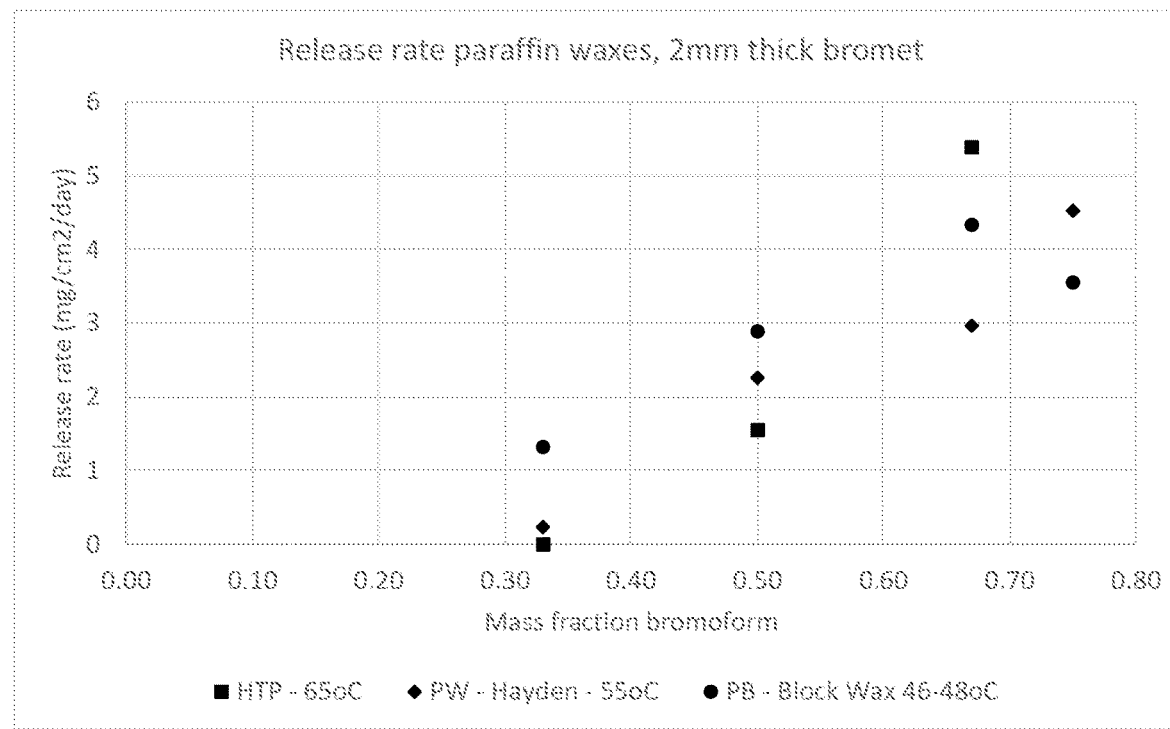
FIG. 13A is a graph showing the release rate of bromoform from paraffin wax as a carrier.
Figure 13B:
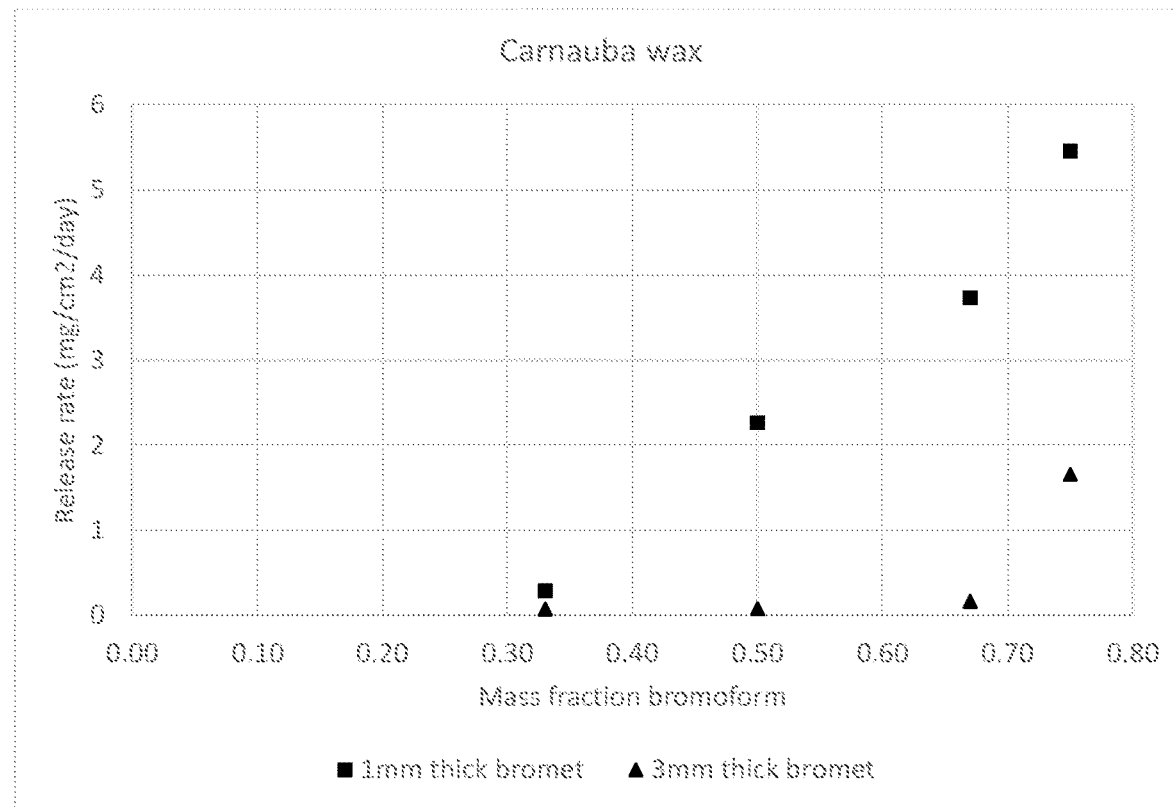
FIG. 13B is a graph showing the release rate of bromoform from carnauba wax as a carrier.
Figure 13C:
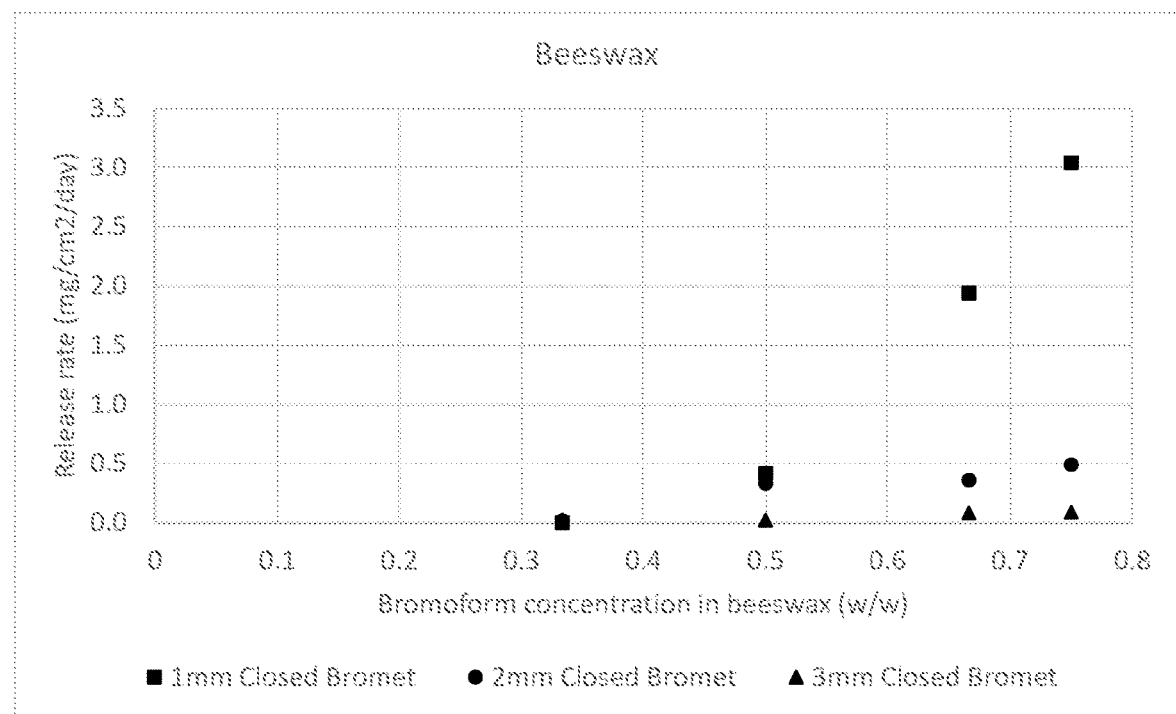
FIG. 13C is a graph showing the release rate of bromoform from Beeswax as a carrier.

Bromoform had the greatest release rate in boluses made with paraffin waxes at 3.5 to 5.4 mg/cm2/day in the 2 mm thick small capped boluses (FIGS. 13A-C).

Boluses made with carnauba wax had release rates up to 5.5 mg/cm2/day in the 1 mm thick bolus and 1.66 mg/cm2/day in the 3 mm thick bolus.

In comparison, boluses made with beeswax had a release rate of 3 mg/cm2/day at 75% (by weight) bromoform (FIG. 13C).

Figure 14:
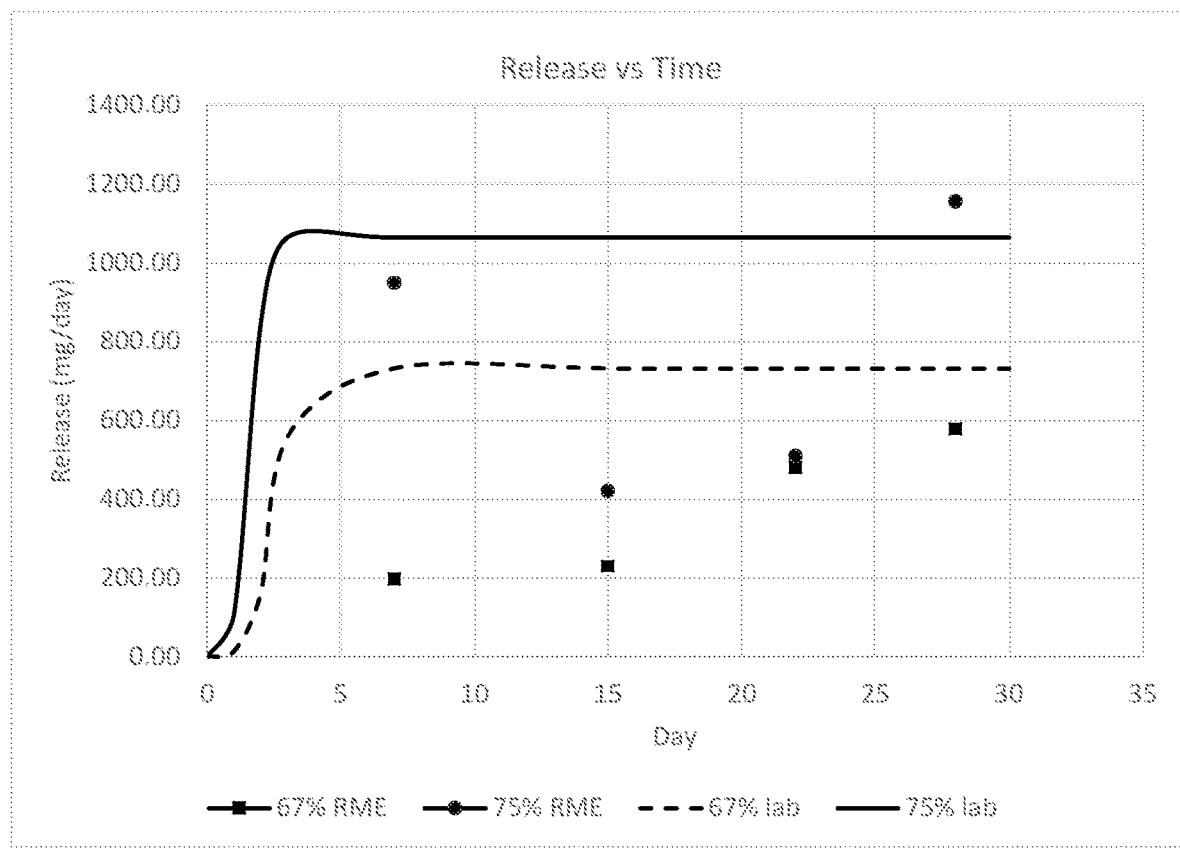
FIG. 14 is a graph showing the average release rate of bromoform for a reinforced bolus in accordance with an embodiment of the present invention.
Figures 15A, 15B:
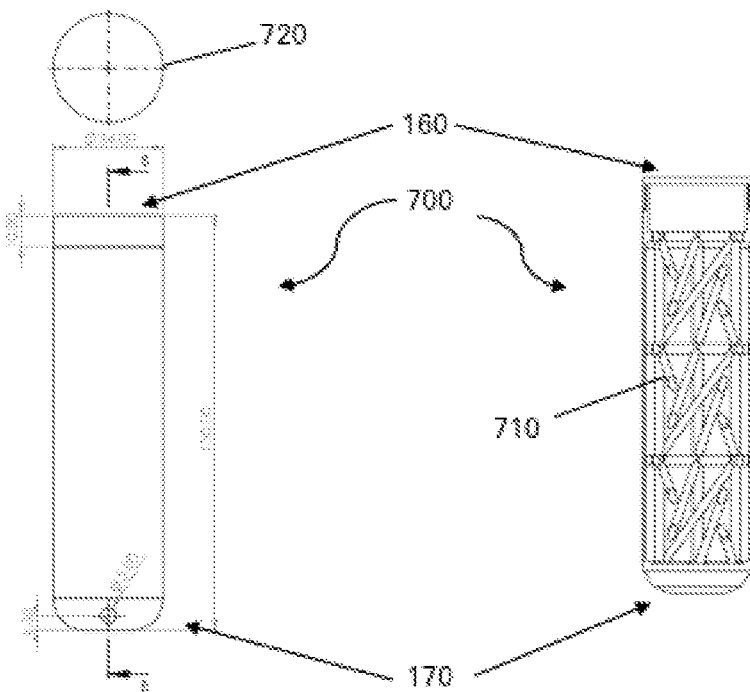
FIG. 15A is a side view showing a reinforced bolus design in accordance with an alternative embodiment of the present invention.
FIG. 15B is a side cross section view of a reinforced bolus design in accordance with an alternative embodiment of the present invention.
Figures 15C, 15D:
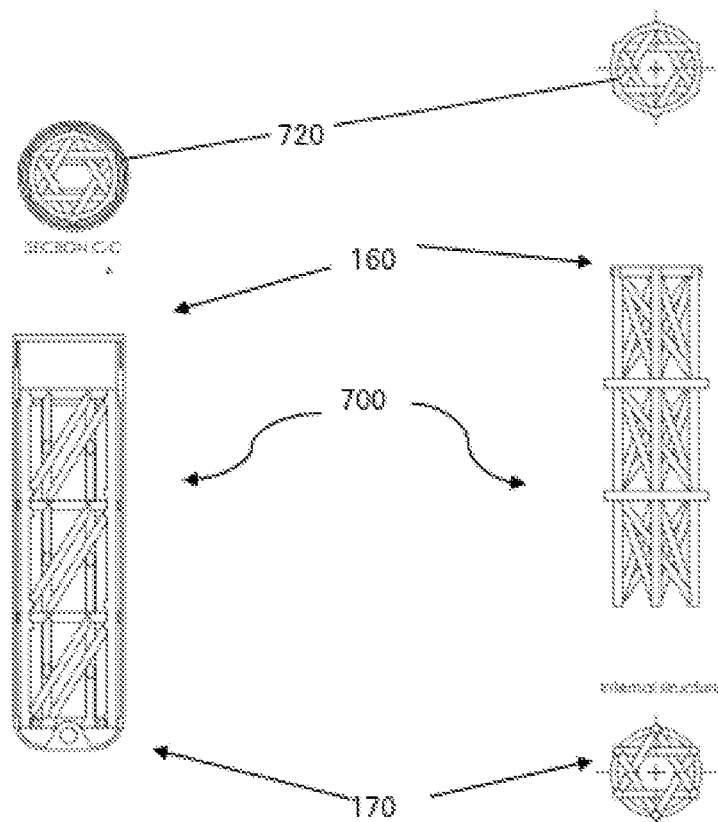
FIG. 15C is a side cross section view of a reinforced bolus design in accordance with an alternative embodiment of the present invention.
FIG. 15D is a cross section view of the internal structure of a reinforced bolus design in accordance with an alternative embodiment of the present invention.

The bromoform had dissolved the castor wax and it had diffused through the bolus and pooled on the bottom of the container, dissolving the container, and no release rates were able to be determined as bromoform was not detected in the water for the samples that had been collected. The trials with castor wax can be repeated in glass bottles.
Release Rates from Reinforced Bolus Average release rates for large reinforced boluses with 67% (by weight) and 75% (by weight) bromoform, prepared as described previously in example 1 above, from another trial are shown in FIG. 14 and compared to release rates from the same boluses measured in the lab. Half of the boluses were in 20 L buckets with 1 kg of sand filled with buffer at pH 6.5, and the other half were in 20 L buckets with 400 g of wood shavings and 1 kg of sand. Release rates are comparable at day 28 to those observed in the lab. Little difference in bromoform concentration was observed between buckets containing wood shavings and buckets without wood shavings. Boluses have largely remained intact, with some compression due to sand, and some have had their lids opened.

Example 3: Animal Study

An animal study was conducted to determine methane emissions from an animal implanted with a bolus of the present invention. The experiment was designed as an unbalanced, completely randomized design with three treatments and three repeated measurements over time in three periods 8 to 12 weeks apart.

Nineteen dairy beef heifers (312±14 kg live weight), including three spare animals, were selected from a mob of 50 based on behaviour traits and liveweight from a research farm in the Manawatu, New Zealand. They were assigned to one of three treatments: a bolus containing no bromoform (CONTROL; n=4); a bolus releasing bromoform at a rate of about 300-400 mg/day (LOW, n=6); or a bolus releasing about 450-580 mg/day (HIGH, n=6). SmaXtec boluses were administered at the same time to monitor rumen temperature as an animal health monitor and to complement the weekly blood samples.

The heifers were transported from research farm to a testing centre for diet adaptation and gas measurements using respiration chambers. The heifers were adapted to the environment of the cattle yards and the fresh cut pasture for 7 days before receiving their allocated treatment bolus. Gas measurements started 13 days after the boluses were administrated. Each heifer was in the respiration chambers for 48 hours during the period of gas measurements, which took two weeks for four measurement groups. At the end of the measurements in respiration chambers, the animals were transported back to research farm.

Bolus Preparation

The boluses were manufactured in accordance with the procedure described in example 1 above. The following formulations used in this trial are shown table 4 below.

TABLE 4

Formulation for the shortened reinforced boluses for the Research Trial

| Type | Bromoform mass fraction in wax | Quantity | Per bolus Zinc Oxide (g) | Per bolus Beeswax (g) | Per bolus Bromoform (g) | Total Zinc Oxide (g) | Total Beeswax (g) | Total Bromoform (g) |
|---|---|---|---|---|---|---|---|---|
| LCB2 | 0 | 6 | 28.0 | 80.4 | 0.0 | 168.0 | 482.7 | 0.0 |
| LRB1 | 0.67 | 8 | 12.1 | 21.3 | 43.2 | 93.4 | 164.0 | 332.9 |
| LRB1 | 0.75 | 8 | 12.1 | 17.8 | 53.5 | 93.4 | 137.4 | 412.1 |

Bolus Administration

The three versions of boluses were made within the first 10 days of the experiment. The first version was a short bolus which was regurgitated by all animals within the 5 days after the boluses were administered. Because the control boluses were longer than the treatment boluses and these had not been regurgitated during the first 3 days, it was assumed that the bolus size was the major factor for regurgitation. All first-version treatment boluses were replaced with second-version boluses on day 5 after administration. However, the longer boluses of the second version were also regurgitated. Therefore, these boluses were then replaced with a third version treatment bolus, which was a significantly heavier bolus of the same size as the second version bolus. The third-version boluses have not been regurgitated to-date. Currently almost all heifers have been dosed with third-version boluses, except for three of the LOW treatment heifers. Details of boluses regurgitation and re-administration are in Table 5.

Two control boluses were regurgitated, but only one was identified because the bolus ID was illegible. None of control boluses were re-administered because it was not possible to identify the heifer-bolus match.

Feed Intake and Liveweight

The heifers were fed cut ryegrass-based pasture offered ad libitum. The forage was harvested daily at approximately 10:00 at research farm and transported to the testing centre. The harvested forage was divided into two allocations, the first allocation was fed in the afternoon at 15:30 and the second allocation was stored at 4° C. until the next morning feeding at 08:30. Samples were collected from each pasture delivery for dry matter determination and feed analysis. Dry matter (DM) was determined from triplicate subsamples by oven drying at 105° C. for 24 h. A separate subsample was oven dried at 65° C. for 48 h for chemical nutrient analyses. Both drying ovens used were forced-air ovens (Avantgarde FED 720, Binder GmbH, Germany).

Two days prior to entering respiration chambers for methane measurements, the cows were put into metabolic crates to adapt them to confined spaces and being tied. When the animals were in metabolic crates or respiration chambers, feed refusals were collected twice daily, and refusal DM was determined as described above. Daily dry matter intake of the heifers was then determined from the difference of the dry matter offered and refused.

Liveweight was recorded pre-trial when animals were grazing at the research farm on two occasions (13 Jul. 2021 and 16 Jul. 2021). The animals were weighed again on 19 Jul. 2021 on arrival at testing farm and every 7-10 days while on site. Initial liveweight was measured on 23 Jul.

TABLE 5

Bolus administration events of the different bolus versions during the first three weeks after initial administration.

| Animal ID | Treatment | V1* bolus ID | V2 bolus ID | V2 bolus administration | V3 bolus ID | V3 bolus administration |
|---|---|---|---|---|---|---|
| 780 | CONTROL | 1 | | | | |
| 782 | CONTROL | 2 | | | | |
| 789 | CONTROL | 3 | | | | |
| 796 | CONTROL | 5 | | | | |
| 797 | CONTROL | 4 | | | | |
| 783 | LOW | 1 | 1 | 30 Jul. 2021 | 1 | 13 Aug. 2021 |
| 787 | LOW | 3 | 3 | 30 Jul. 2021 | | Not regurgitated |
| 788 | LOW | 2 | 2 | 31 Jul. 2021 | | Not regurgitated |
| 790 | LOW | 5 | 5 | 30 Jul. 2021 | 5 | 7 Aug. 2021 |
| 791 | LOW | 5 | 4 | 30 Jul. 2021 | | Not regurgitated |
| 793 | LOW | 6 | 8 | 30 Jul. 2021 | 6 | 13 Aug. 2021 |
| 794 | LOW | 7 | 7 | 30 Jul. 2021 | 7 | 10 Aug. 2021 |
| 784 | HIGH | 9 | 9 | 1 Aug. 2021 | 9 | 10 Aug. 2021 |
| 785 | HIGH | 10 | 10 | 30 Jul. 2021 | 10 | 10 Aug. 2021 |
| 786 | HIGH | 11 | 14 | 30 Jul. 2021 | 8 | 7 Aug. 2021 |
| 792 | HIGH | 12 | 12 | 31 Jul. 2021 | 12 | 13 Aug. 2021 |
| 795 | HIGH | 13 | 13 | 30 Jul. 2021 | 13 | 12 Aug. 2021 |
| 798 | HIGH | 14 | 11 | 1 Aug. 2021 | 11 | 9 Aug. 2021 |
| 781 | HIGH | 15 | 8 | 30 Jul. 2021 | 14 | 13 Aug. 2021 |

*V1: all boluses administred on 27 Jul. 2021

2021 before bolus administration and final liveweight was once animals left the respiration chambers. Final liveweight dates are different for some animals because measurements were undertaken over two weeks.

Gas Measurements

Fermentation gases methane ($CH_4$), carbon dioxide ($CO_2$) and hydrogen ($H_2$) were quantified in four open-circuit respiration chambers at the New Zealand Ruminant Methane Measurement Centre (AgResearch, Palmerston North, New Zealand). Each chamber is 15.4 $m^3$ (3.5 m long×2 m wide×2.2 m high) with an air flow rate of around 1.0 $m^3$/min, which was continuously monitored by measuring differential pressure using a Venturi flowmeter. Temperature inside respiration chambers was approximately 20° C. and the relative humidity was on average approximately 79%. All gases were measured at ~2.8-min intervals using a 4900C Continuous Emission analyser (Servomex Group Ltd, East Sussex, UK) and daily production of each gas was calculated from the difference between concentration flowing in- and out of the chamber (Pinares-Patiio et al., 2012). Respiration chambers were opened twice daily (~20 min each time) for cleaning, feeding, faecal sampling and feed refusal collection. No measurements were performed during the period when chambers were opened, and missing data were interpolated by taking the average of the last 12 values (~45 min) before the doors were opened.

Statistical Analyses

Data from the first period of gas measurements was analysed using the 'predictmeans' and 'lme4' packages in the statistical software R 4.0.3 (R Core Team, 2020). Data for dry matter intake and gas emissions for each heifer were averaged across the two measurement days. Heifer served as the experimental unit. The mixed model included treatment as fixed effect and respiration chamber nested in measurement group as random effect.

Liveweight analyses included treatment as a fixed effect and time as a repeated measurement, with heifer as a subject for the repeated measurements. Only initial and final liveweight were included in this analysis.

Results

Dry Matter Intake and Gas Emissions

Dosing heifers with bromoform at about 300-400 mg/day (LOW) or about 450-580 mg/day (HIGH) did not affect the dry matter intake measured over the two days the animals were in respiration chambers compared with the control group (p=0.42). Both: $CH_4$ production (g/day) and $CH_4$ yield (g/kg unit of dry matter intake) decreased by more than 99% in LOW and HIGH compared with CONTROL (p<0.01). The decrease in $CH_4$ emissions at LOW and HIGH treatments was accompanied by an increase in $H_2$ emissions per day (Table 7). As both treatments decreased methane emissions completely, a lower dose can be used to achieve levels of methane reduction between 30 and 90%. A reduction in the daily dose would ensure that not more bromoform than necessary is used to increase the lifetime of the bolus and would decrease the risk of negative effects on the animal and potential contamination of animal products. Given that methane emissions are fully inhibited, it is noteworthy that dry matter intake was not negatively affected as has been observed when bromoform containing *Asparagopsis* is fed (Roque et al. 2019).

TABLE 7

Dry matter intake (DMI) methane (CH4) and hydrogen (H2) emissions measured in respiration chambers over two days in heifers dosed boluses releasing no bromoform (CONTROL), 300 mg/d (LOW) or 450 mg/d (HIGH) of bromoform

|  | CONTROL | LOW | HIGH | SED | p-value |
| --- | --- | --- | --- | --- | --- |
| DMI [kg/d] | 5.20 | 4.98 | 4.50 | 0.79 | 0.420 |
| $CH_4$ [g/d] | $120.25^a$ | $0.34^b$ | $0.77^b$ | 2.74 | <0.01 |
| $CH_4$ [g/kg DMI] | $23.32^a$ | $0.14^b$ | $0.11^b$ | 0.33 | <0.01 |
| $H_2$ [g/d] | $0.15^b$ | $20.60^a$ | $20.08^a$ | 3.46 | <0.01 |

Conclusion

As observed, the results above indicate treatment using a bolus with the present invention is highly effective a few weeks after the boluses were administered, as demonstrated by the ~99% reduction in methane.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavor in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Example 4

Methods Materials

PLA (3052D), PBS (supplier Convex) and PBAT (supplier Convex) were freeze dried in aluminium foil trays using a Labcono freeze drier before use to reduce water content in the blends.

Manufacture of Boluses

Blends of PLA (3052D), PBS, PBAT were made by mixing the pellets in the following ratios:

TABLE 8

Formulations of blends made (% by weight)

| | PLA | PBS | PBAT |
|---|---|---|---|
| 1 | 100 | | |
| 2 | 70 | 30 | |
| 3 | 40 | 60 | |
| 4 | 20 | 80 | |
| 5 | 70 | | 30 |
| 6 | 40 | | 60 |
| 7 | 20 | | 80 |

Blends were prepared by melt blending in a LabTech corotating twin screw extruder (L/D 44:1) with a screw speed of 200 rpm. Temperature profile increased over 11 barrel heating sections, from 70° C. at the feed throat to 220° C. along the main barrel, and increasing to 230° C. at the die. Blends were granulated using a triblade granulator with a 4 mm plate (Castin Machinery, NZ). The blends were stored in aluminium foil trays and bagged in zip lock bags before use. All blends oven dried overnight at 40° C. before injection moulding. Tensile bars (ASTM D368) and impact bars (ISO 179) were produced in a BOY 35A injection moulding machine, with a temperature profile of 70 to 220° C. from feed to nozzle. Mould temperature was kept constant at 50° C. Lanolin was used as a mould release agent and was sprayed into the mould prior to each tensile bar being produced.

Analysis of Boluses

Shrinkage from injection moulding was determined by measuring the width and thickness of the tensile specimens, subtracting this from the mould width and depth, and dividing by the mould width and depth and multiplying by 100 to obtain a percentage. Tensile bars were cut into ~2 cm lengths using a bandsaw and the edges sanded using 500 grit sandpaper until smooth. 120 cm diameter flat bottom glass petri dishes were filled with beeswax/bromoform mixtures at the following bromoform concentrations: 33, 50, 67, 75% by weight. Three samples of each PLA blend were labelled, weighed in a 4dp electronic balance, and thickness, length and width measured using digital calipers. These were then placed flat and gently pressed into each bromoform/beeswax formulation to ensure good contact between the beeswax and PLA surfaces. Glass lids were then placed on the petri dishes and sealed using insulation tape, before being placed in the incubator at 40° C.

Samples were also tested for hardness using the Shore D hardness tester at a 7 kg weight, and structural properties using the XRD.

Every two or three days samples were removed from the petri dishes, cleaned using tissue paper, weighed using the 4dp electronic balance, and measured using the digital calipers.

Bromoform absorption was determined by measuring the total change in mass of the sample and dividing by the starting mass of the sample. Rate of absorption was determined by dividing the change in mass of the sample between measurements by the area of sample in contact with the bromoform/beeswax mixture and dividing by the change in time between measurements.

Swelling was determined by measuring the change in volume of the sample and dividing by the original volume of the sample.

Results

Injection Moulding

Shrinkage for PLA was around 0.2% and increase to around 1-1.2% for increasing PBS and PBAT blends (FIG. 16). The average skilled person knows how to adjust for shrinkage to produce a bolus of a desired size and dimension. It should be appreciated that various sizes of the bolus are possible, and they are not critical for achieving a delayed release of the haloform in view of the teachings of the present patent application.

Figure 16B:
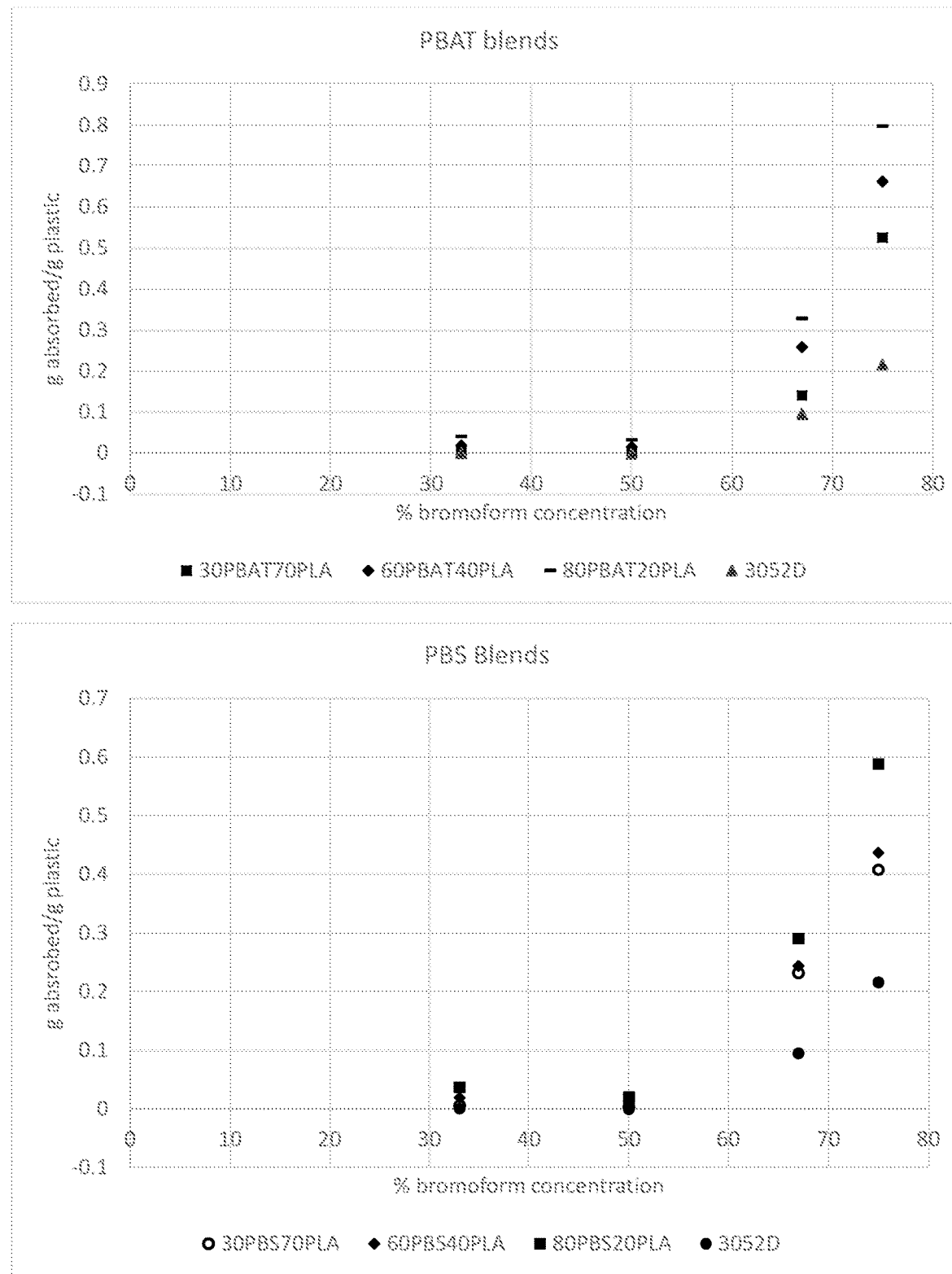
FIG. 16B shows bromoform absorbed vs bromoform composition in beeswax for different compositions of PLA blended with PBS and PBAT.
Figure 16C:
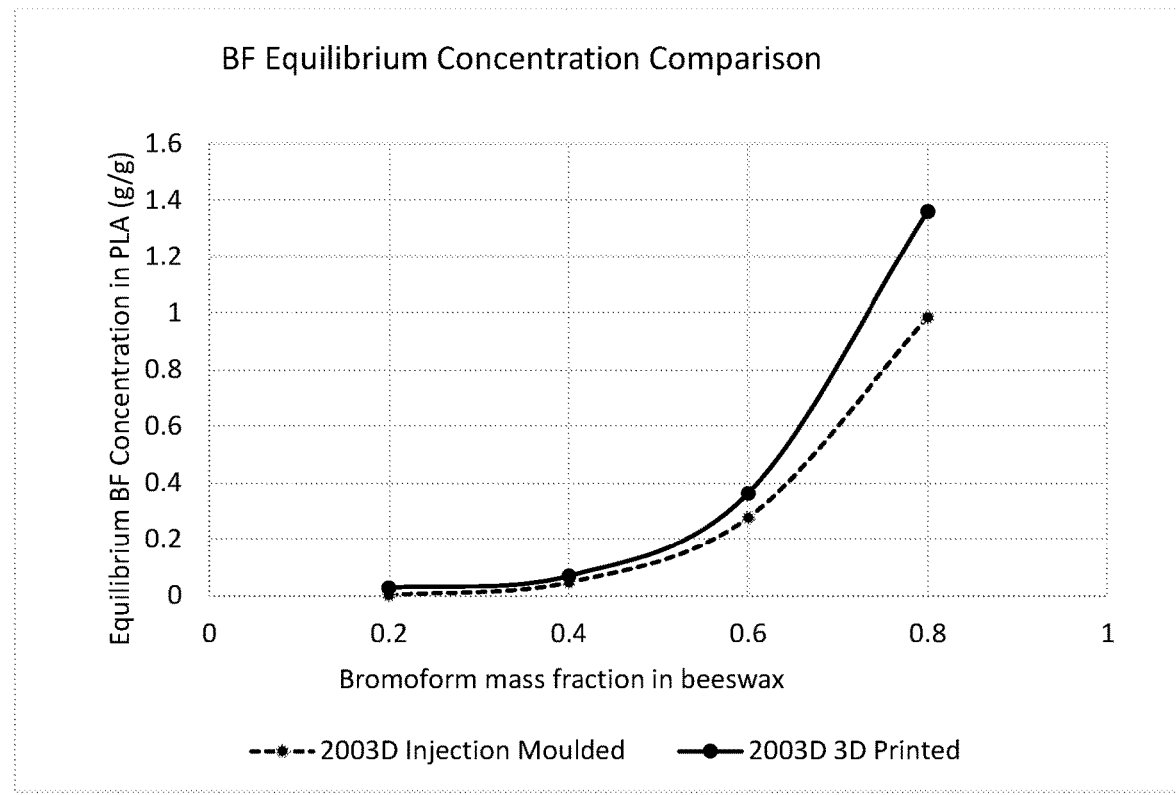
FIG. 16C shows bromoform absorbed vs bromoform composition in beeswax for 3D printed PLA and injection moulded 2003D PLA.
Figure 16D:
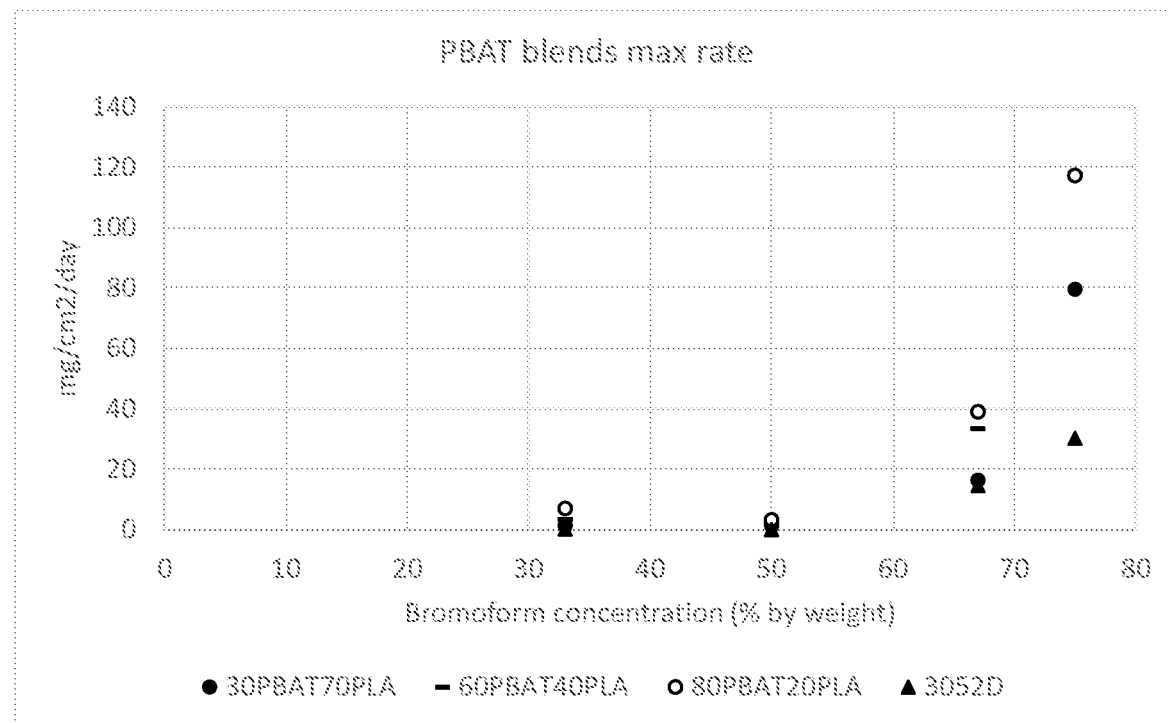
FIG. 16D shows bromoform absorption rate vs bromoform composition in beeswax for different compositions of PLA blended with PBS and PBAT.
Figure 16D:
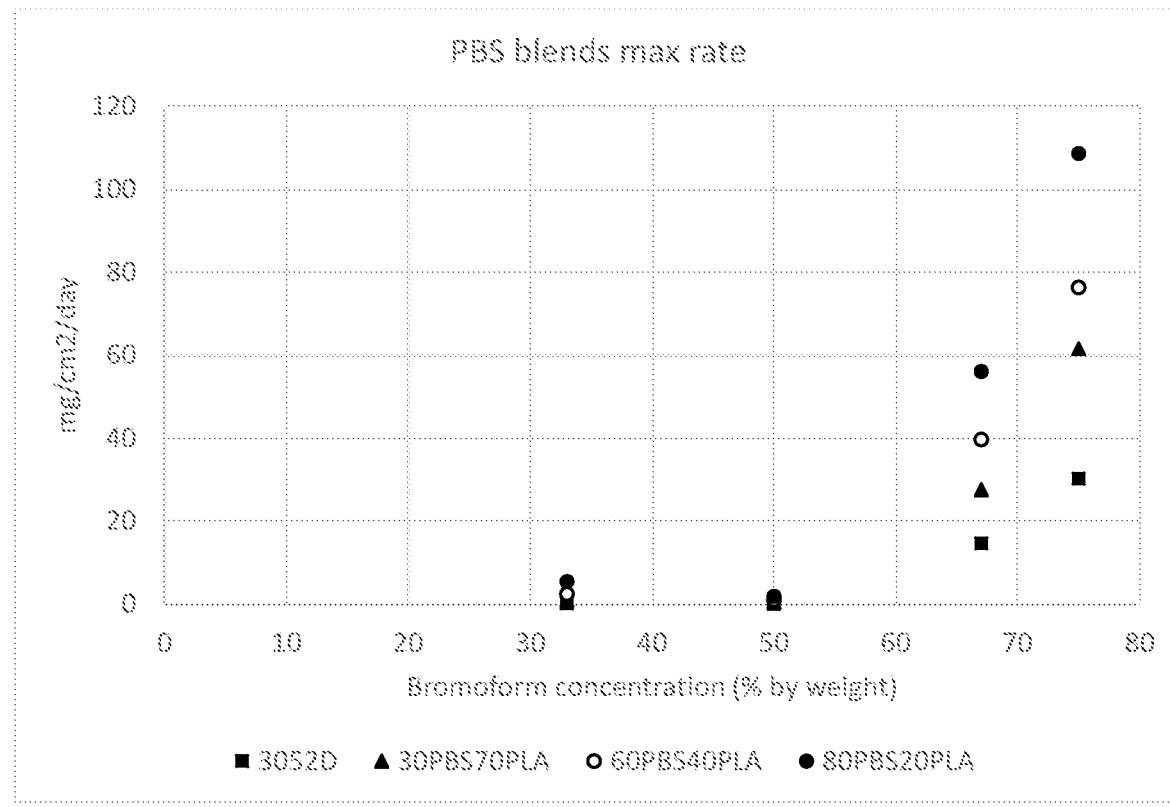
Figure 16E:
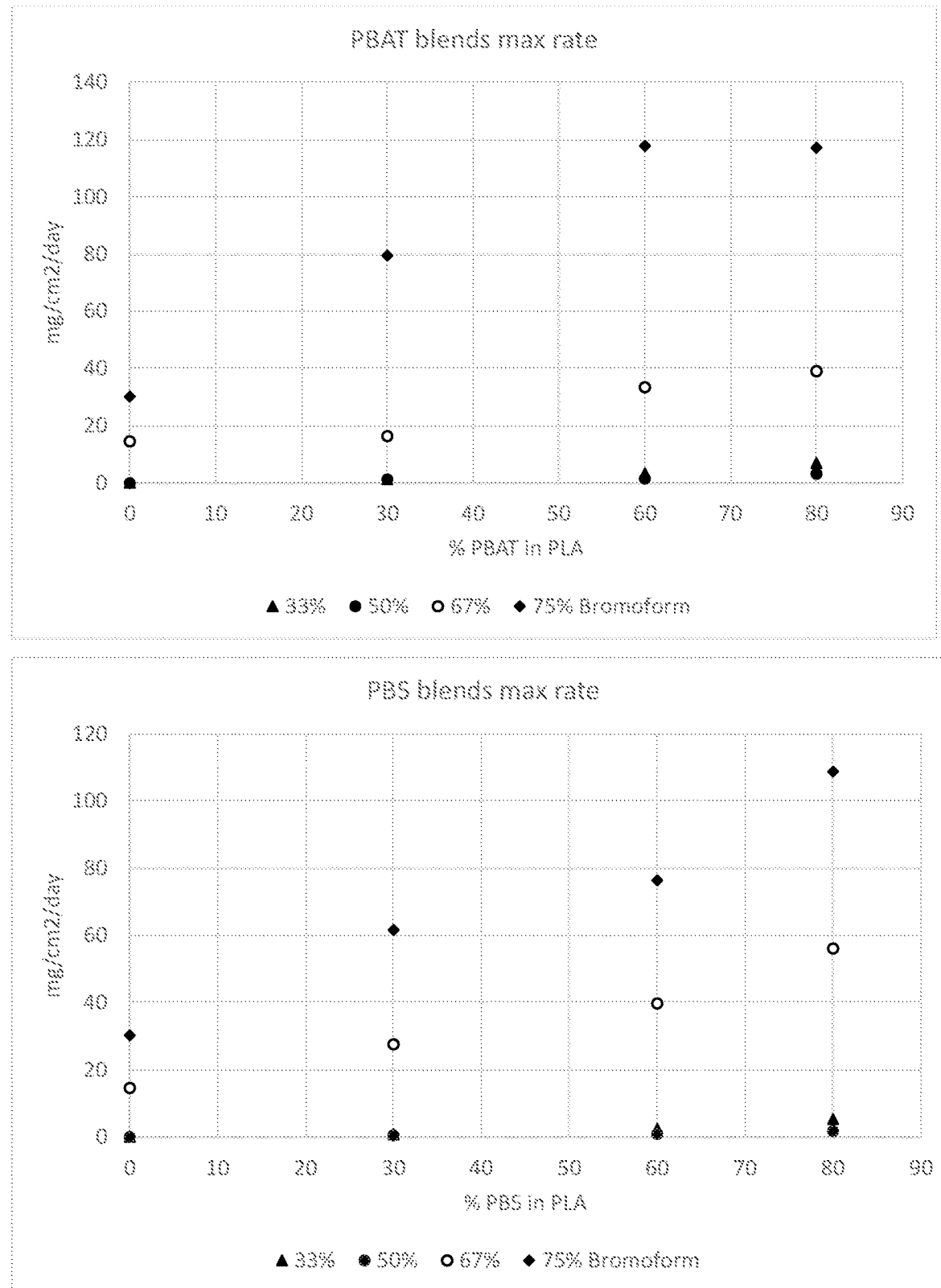
FIG. 16E shows bromoform absorption rate vs PLA composition in beeswax with different concentrations of bromoform.

Less bromoform was absorbed at bromoform concentrations in beeswax below 50% by weight, suggesting limited mobility of bromoform at low concentrations of bromoform in beeswax, and a strong holding capacity of beeswax for bromoform (FIG. 16B). As bromoform concentration increased in beeswax and the mass fraction of PBAT and PBS increased in PLA, the mass of bromoform absorbed increased, and the maximum rate of absorption also increased (FIGS. 16C and D). The masses absorbed for the PLA blends were lower than that for 2003D PLA and 3D printed PLA (FIG. 16E).

Example 5

Methods

Samples were prepared and analysed as described in Example 4, unless indicated otherwise.

Samples were also tested for hardness using the Shore D hardness tester at a 7 kg weight, and structural properties using the XRD before and after exposure to the bromoform/beeswax mixtures.

A PANalytica Empyrean XRD was used for XRD analysis with a flat sample stage holder with an adjustable beam to maintain an exposed area of 1 cm by 5 mm at all angles between 5 and 70 2Theta, with the following configuration:

TABLE 9

| Configuration for XRD analysis: | |
|---|---|
| Configuration | Flat Sample Stage, Owner = User-1, Creation date = 30 May 2013 9:05:47 AM |
| Goniometer | Theta/Theta; Minimum step size 2Theta: 0.0001; Minimum step size Omega: 0.0001 |
| Sample stage | Stage for flat samples/holders |
| Diffractometer system | EMPYREAN |
| Anode material | Cu |
| K-Alpha1 wavelength | 1.540598 |
| K-Alpha2 wavelength | 1.544426 |
| Ratio K-Alpha2/K-Alpha1 | 0.5 |
| Monochromator used | NO |
| Generator voltage | 45 |
| Tube current | 40 |
| Scan axis | Gonio |
| Scan range | 5-70 |
| Scan step size | 0.01313 |
| No. of points | 4417 |
| Scan type | CONTINUOUS |
| Time per step | 39.27 |

XRD data was exported to Excel, smoothed with a 10 point smooth, and baseline corrected between 5 and 60 2theta.

Results

Figure 17:
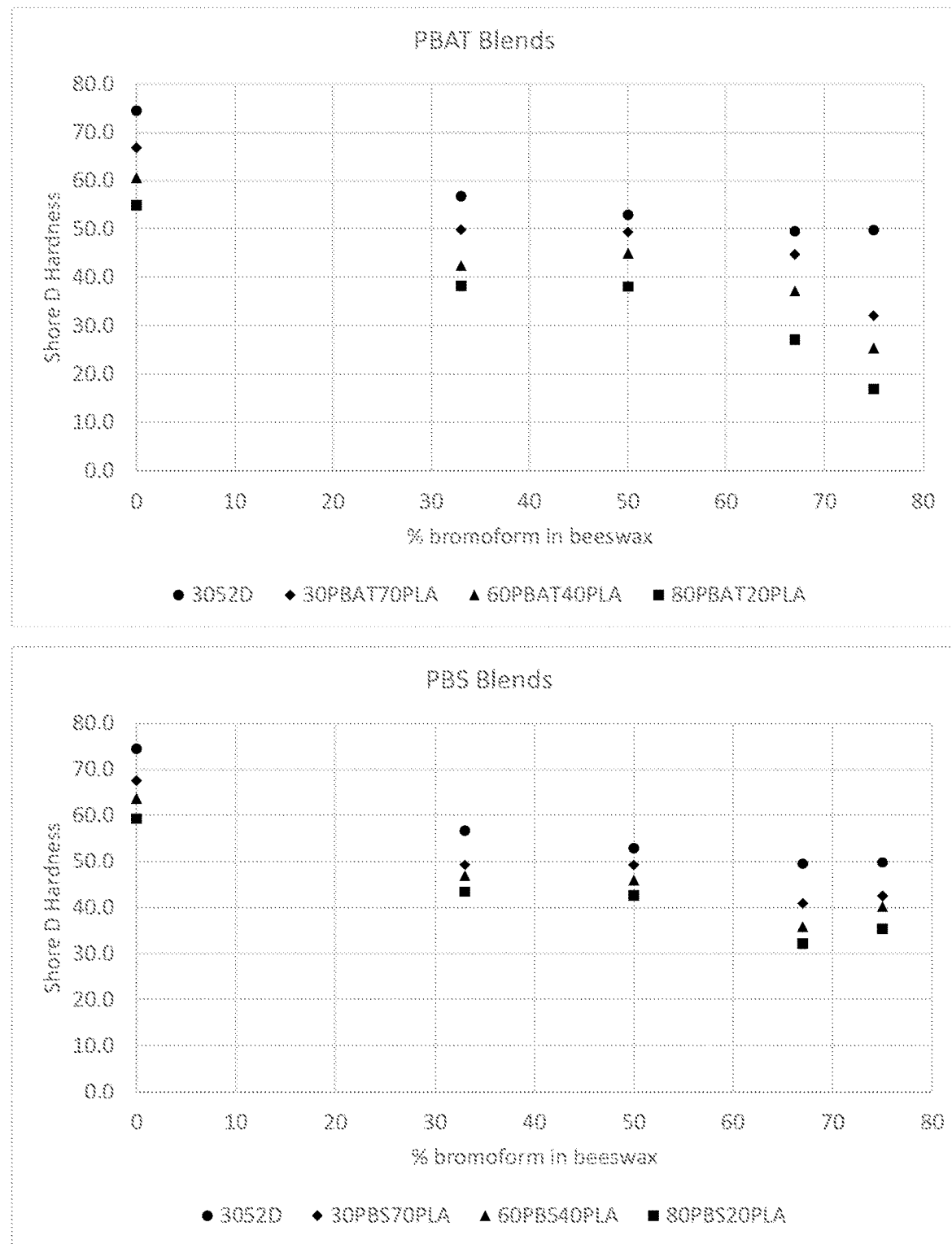
FIG. 17 shows hardness analysis of PLA blends before and after exposure to bromoform.

FIG. 17 shows hardness analysis of PLA blends before and after exposure to bromoform. Thus, by including PBS in the carrier, the mixture becomes less sensitive to bromoform exposure, which may facilitate shelf life.

Example 6

Release Testing of Large, Reinforced Bolus (Rissington Trial)

The boluses were drawn in Solidworks, converted to .stl files, opened in FlashPrint to create the print jobs. The boluses were printed in three parts (case, internal structure, and cap) on FlashForge Creator Pro 3D printers using E-Sun PLA+ at 100% fill, standard resolution, first layer height 0.27 mm, layer height 0.18 mm, 2 perimeter shells, 3 top solid layers, 3 bottom solid layers, fill pattern hexagon, print speed 60 mm/s, extruder temperature 200° C. and plate temperature 50° C.

Two Individual formulations comprising of 67% and 55% (by weight) bromoform in a castor wax: paraffin wax (in this example: the ratio was 50:50) as carrier mixture were prepared. Next, individual bromoform wax mixture was poured into the 1 mm thick casing after inserting a zinc rod as a densifier. The cap was mounted and sealed using the soldering gun. The release test was carried out as per the method described in Example 1 with a slight modification, where a 2 L media was used instead and replaced daily. A volume of 10 ml sample was taken and extracted with ethyl acetate suitably before injecting into the GC to quantify the bromoform release.

Figure 18A:
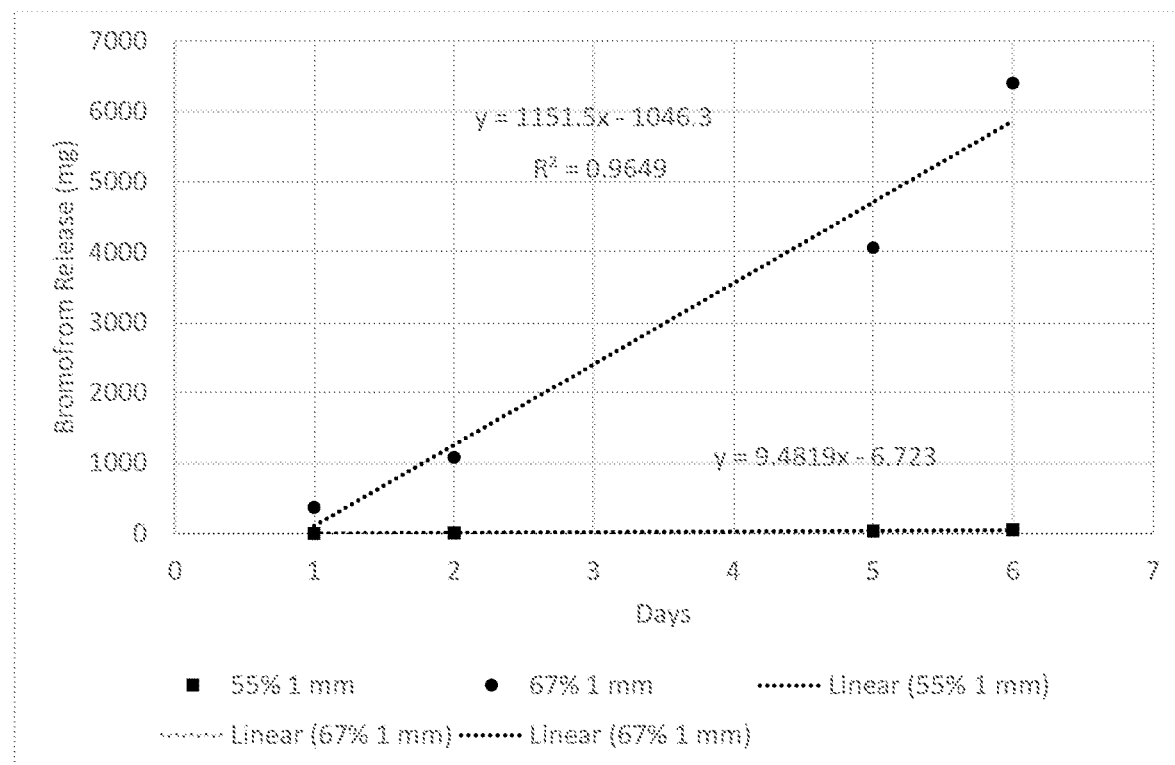
FIG. 18A shows the release of Bromoform from 67% (by weight) and 55% (by weight) Bromoform loaded 1 mm thick boluses.

The Bromoform released at a higher rate from the bolus with 67% (by weight) bromoform (1150 mg/day). Meanwhile, the release rate was slower from the bolus with 55% (by weight) bromoform loading with 9.5 mg/day (FIG. 18A).

Figure 18B:
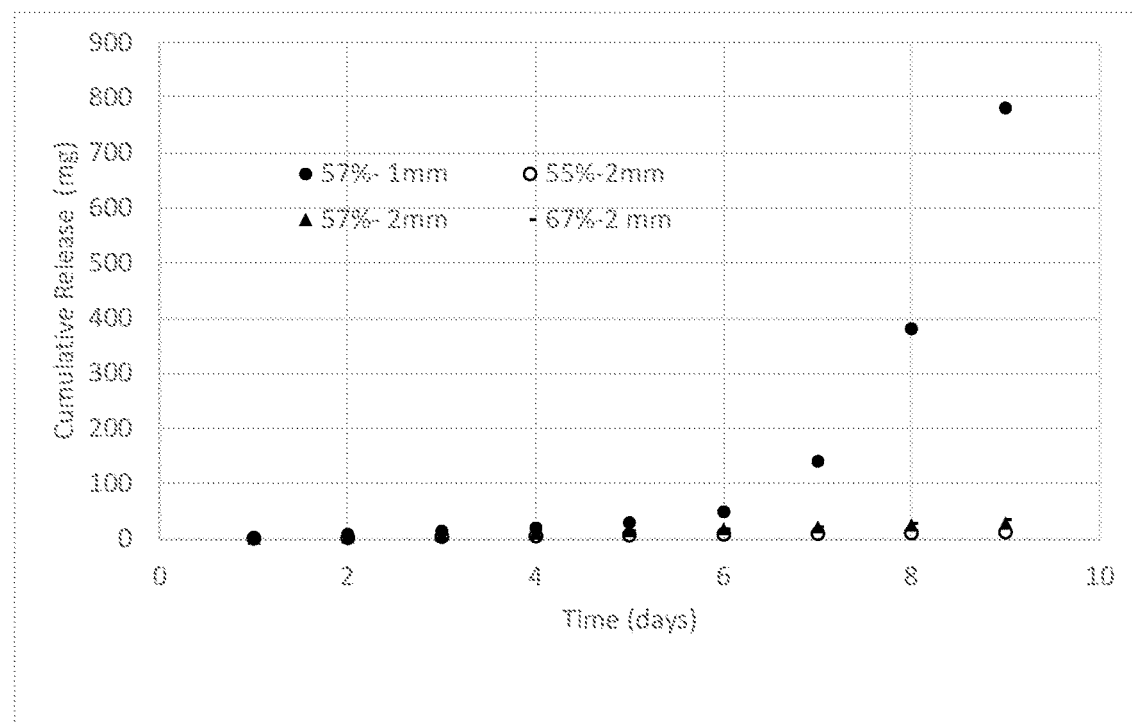
FIG. 18B shows cumulative release of Bromoform from boluses.
Figure 18C:
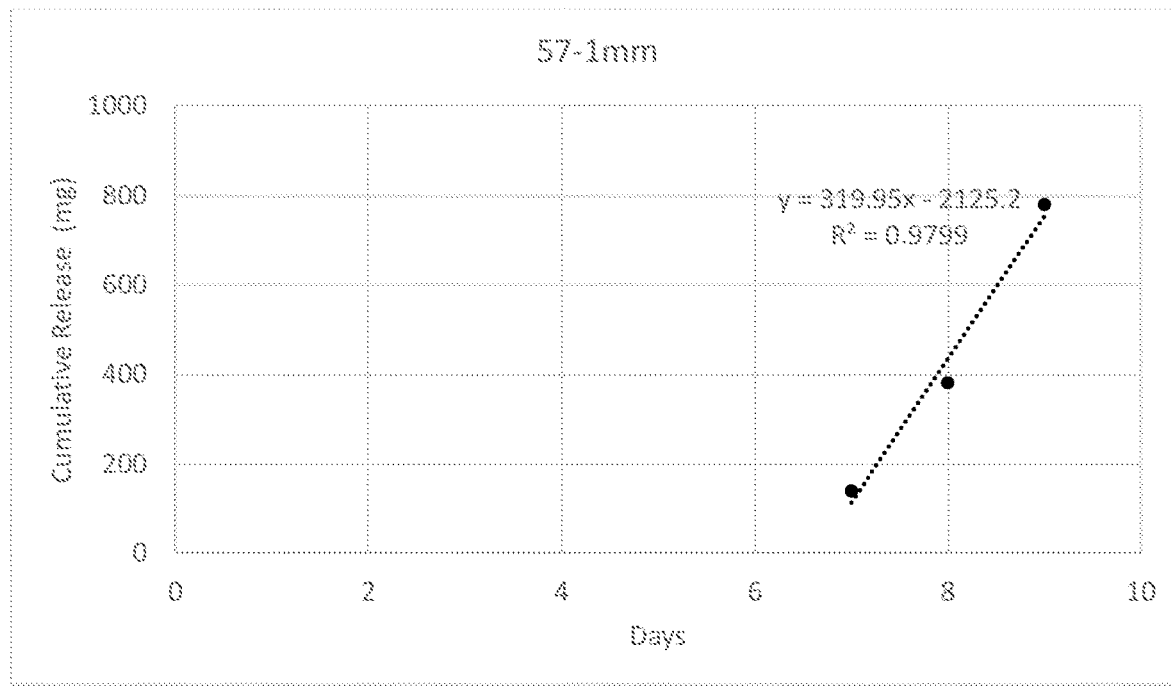
FIG. 18C shows cumulative plot of 7, 8 and 9 days for 57-1 mm bolus.
Figure 18D:
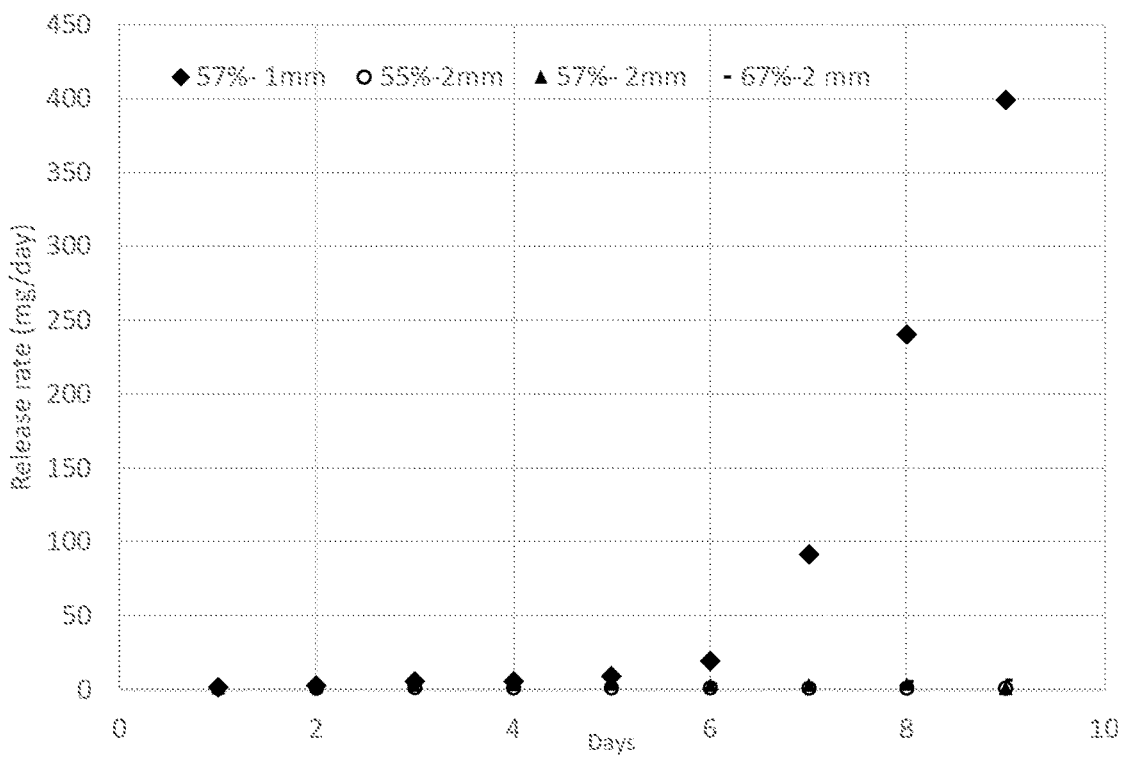
FIG. 18D shows release rate from different boluses.

Next, 4 different types of boluses (2 each) with 57% (by weight) Bromoform with 1 mm and 2 mm casing and 55% (by weight) and 67% (by weight) bromoform with 2 mm casing with similar carrier composition with zinc rod were prepared. The release testing was carried out as per the method described above. It was found that the release rate was slow with 2 mm casing and release rate was slow regardless of the bromoform content (FIGS. 18B-D). Meanwhile, the 1 mm casing bolus with 57% (by weight) bromoform had a lag time for 7 days with reaching 240 mg at 8th day and 400 mg at 9th day (FIG. 18D). Cumulative plot for 7, 8 and 9 days showed best fit indicating release rate of 319 mg/day (FIG. 18C).

Each of the respective boluses were tested in RME as per the method described in the Examples above. The boluses were recovered after 6 days of study and examined visually. The boluses remained intact with no signs of any breakage or deformations.

Example 7

Design of a Bromoform Containing Bolus

In one preferred embodiment tested in this example the bolus comprises a housing and a core composed as defined below:

| | |
|---|---|
| Bolus dimensions | 13 cm length; 3.4 cm diameter; 257 gm weight |
| Housing design | Including a cap; wall thickness: 1 mm; |
| Core matrix | Blend of two or more waxes, e.g. Castor wax/ Paraffin wax blend |
| Bromoform concentration in the core | 33%-75% (by weight) |

Also provided are the following preferred embodiments according to the invention:

Embodiment 1 provides a delayed release dosage form or a bolus configured for administration to an animal, wherein said dosage form and said bolus is configured to release a hydrophobic substance to the animal over a period of time.

Embodiment 2 provides a delayed release dosage form or a bolus for administration to a ruminant animal, wherein said delayed release dosage form and said bolus is configured to release an effective amount of the substance.

Embodiment 3 provides a delayed release dosage form or a bolus for administration to a ruminant animal, wherein said delayed release dosage form and said bolus comprises:
  a core, wherein the core includes at least one substance to be administrated to the ruminant animal mixed with a carrier; and
  a housing which covers at least a portion of the core;
  wherein, the bolus is configured to release the substance through the housing over a predetermined period of time.

Embodiment 4 provides the bolus of any one of embodiments 1-3, wherein the carrier and the substance have a relatively higher affinity for each other compared to the affinity of the housing and the substance for each other.

Embodiment 5 provides the bolus of embodiment 4, wherein the substance is a hydrophobic substance.

Embodiment 6 provides the bolus of any one of embodiments 1-5, wherein the substance is at least one inhibiting agent.

Embodiment 7 provides the bolus of embodiment 6, wherein the inhibiting agent is a haloform, wherein the haloform is preferably selected from the list of bromoform, chloroform, iodoform, and combinations thereof.

Embodiment 8 provides the bolus of embodiment 7, wherein the at least one inhibiting agent is bromoform.

Embodiment 9 provides the bolus of any one of embodiments 7 and 8, wherein the haloform, preferably bromoform, is comprised in the core in an amount of between 30 wt % to 80 wt % and preferably in an amount of between 30 wt % and 70 wt %.

Embodiment 10 provides the bolus of any one of embodiments 7 to 9, wherein the haloform, preferably bromoform, is comprised in the core in an amount of at most 55 wt %.

Embodiment 11 provides the bolus of any one of embodiments 7 to 10, wherein the haloform, preferably the bromoform, is comprised in the core and the carrier comprises or consists of wax.

Embodiment 12 provides the bolus of any one of embodiments 3-11, wherein the carrier is a polar substance.

Embodiment 13 provides the bolus of embodiment 12, wherein the carrier includes polar functional groups such as ester, alcohol or carbonyl groups.

Embodiment 14 provides the bolus of any one of embodiments 3-13, wherein the carrier is selected from the group consisting of myristic acid, stearic acid, steryl alcohol, cetyl alcohol, cetosteryl alcohol, castor wax, bee's wax, paraffin wax, PEG4000, Carnauba, Candellila, Jojoba, Lanolin, and a combination thereof.

Embodiment 15 provides the bolus of embodiment 14, wherein the wax(es) is (are) mixed with said haloform (preferably bromoform), wherein preferably the carrier comprises bees wax, paraffin wax and/or castor wax, and more preferably wherein the carrier comprises castor wax and paraffin wax in a weight ratio of castor to paraffin wax of between 40:60 to 60:40.

Embodiment 16 provides the bolus of either one of embodiments 11 or 12, wherein the carrier comprises paraffin wax and castor wax.

Embodiment 17 provides the bolus of any one of embodiments 13 to 16, wherein the at least one piece of metal.

Embodiment 18 provides the bolus of any one of embodiments 3-17, wherein the housing includes a cavity in which at least a portion of the core is located.

Embodiment 19 provides the bolus of any one of embodiments 3-18, wherein the housing includes an open end.

Embodiment 20 provides the bolus of any preceding embodiment, wherein the bolus includes a cap configured to close the open end.

Embodiment 21 provides the bolus of any preceding embodiment, wherein the housing and the cap substantially or completely cover and surround the core to define a core.

Embodiment 22 provides the bolus of any one of embodiments 3-21, wherein the housing completely covers and surrounds the core.

Embodiment 23 provides the bolus of any one of embodiments 3-22, wherein the housing is formed from a substance having a Shore D hardness of at least 40.

Embodiment 24 provides the bolus of any one of embodiments 3-23, wherein the housing is formed from a substance having a Shore D hardness of less than 70.

Embodiment 25 provides the bolus of any one of embodiments 3-24, wherein the housing is formed from a material through which the inhibiting agent can migrate.

Embodiment 26 provides the bolus of any one of embodiments 3-25, wherein the housing is made from a plastic material.

Embodiment 27 provides the bolus of embodiment 26, wherein the plastic is one or more of poly lactic acid (PLA), poly glycolic acid (PGA), poly lactic glycolic acid (PLGA), polypropylene, SLA polymer, PBS, PBAT or a combination thereof.

Embodiment 28 provides the bolus of any of embodiments 3-27, wherein the housing is made from a material comprising poly lactic acid (PLA) and Polybutylenadipat-terephthalat (PBAT) and the carrier comprises or consists of wax.

Embodiment 29 provides the bolus of embodiment 28, wherein the material comprises poly lactic acid (PLA) and Polybutylenadipat-terephthalat (PBAT) in a weight ratio ranging from 100:0 to a 40:60 poly lactic acid (PLA): Polybutylenadipat-terephthalat (PBAT)ratio and where the carrier comprises wax.

Embodiment 30 provides the bolus of any one of embodiments 3-29, wherein the housing is made from a material that includes one or more excipients.

Embodiment 31 provides the bolus of embodiment 30, wherein the one or more excipients includes plasticisers, hardeners and/or colourants.

Embodiment 32 provides the bolus of any of embodiments 3-31, wherein the housing has a material thickness of below 2 mm and preferably a material thickness in the range of 0.3-1.5 mm.

Embodiment 33 provides the bolus of any one of embodiments 3-32, wherein the housing is configured to degrade over a predetermined period of time.

Embodiment 34 provides the bolus of any one of embodiments 3-33, wherein the core has a melting point greater than 37° C.

Embodiment 35 provides the bolus of any one of embodiments 3-34, further comprising a barrier layer between at least a portion of the housing and the core to isolate the portion of the housing and the core from contact with each other.

Embodiment 36 provides the bolus of any one of embodiments 7-35, wherein the bolus is adapted to reach a maximum release rate of approximately 0.05 g to 2 g of bromoform per day into the rumen.

Embodiment 37 provides the bolus of embodiment 36, wherein the bolus is adapted to reach a maximum release rate of approximately 0.1 to 0.5 g of bromoform per day into the rumen, preferably of about 0.2 to 0.3 g of bromoform per day into the rumen.

Embodiment 38 provides the bolus of any one of embodiments 1-37, wherein the bolus is adapted to release the substance over a period of at least two months.

Embodiment 39 provides the delayed release dosage form of any one of embodiments 1-3, wherein the substance is a substance as defined in any one of embodiments 4-38 (and most preferably bromoform), wherein the core is a core as defined in any one of embodiments 4-38 and the housing is a housing as defined in any one of embodiments 4-38.

Embodiment 40 provides a method for administering a substance to an animal, the method comprising the step of administering to said animal the bolus of any one of embodiments 1-38 or the delayed release dosage form of any one of embodiments 1-3 or 39.

Embodiment 41 provides a method for reducing methane production in a ruminant animal, the method comprising the step of administering to said ruminant animal the bolus of any one of embodiments 1-39 or the delayed release dosage form of any of embodiments 1-3 or 39.

Embodiment 42 provides the use of a methane inhibitor and a carrier in a bolus for reducing methane production in a ruminant animal.

Embodiment 43 provides the use of a methane inhibitor and a carrier in a bolus for reducing methane emission from a ruminant animal.

Embodiment 44 provides the use of a haloform in the manufacture of a bolus for reducing the emission of one or more greenhouse gases ("GHGs") from a ruminant animal.

Embodiment 45 provides a method of manufacture of a bolus of any one of embodiments 1 to 38, comprising:
 a. forming a housing which has a cavity;
 b. forming a core which includes the substance;
 c. transferring the core to the cavity.

Embodiment 46 provides the method of embodiment 45, wherein the step of forming the core involves mixing a carrier material with the substance.

Embodiment 47 provides the method of embodiment 45 or 46, wherein the step of forming the core involves heating the carrier material to melt the carrier material prior to mixing the carrier material with the substance to create a mixture.

Embodiment 48 provides the method of any one of embodiments 45 to 47, wherein the step of transferring the core to the cavity involves pouring the mixture into the cavity.

Embodiment 49 provides a delayed release dosage form adapted to be administered to a ruminant animal, wherein the system comprises a mixture of a wax and a haloform.

Embodiment 50 provides the delayed release dosage form according to embodiment 49 for administration to a ruminant animal, wherein said delayed release dosage form comprises: a core, wherein the core comprises said wax and said haloform (preferably bromoform); and a coating, which covers at least a portion of the core and preferably covers the entire core; wherein the delayed release dosage form releases the haloform.

Embodiment 51 provides the delayed release dosage form according to embodiment 50, wherein the coating is the housing as defined in any of embodiments 4-38 and wherein the core is a core as defined in any of embodiments 4-38.

Embodiment 52 provides the delayed release dosage form according to any one of embodiments 49 to 51, wherein the haloform is bromoform.

Embodiments 53 provides the delayed release dosage form according to any one of embodiments 49 to 52 or the bolus according to any of embodiments 3-38, wherein the carrier comprises or consists of wax and the coating/housing comprises PLA, PBAT or a mixture of both; preferably the coating/housing comprises PLA.

Embodiment 54 provides the delayed release dosage form according to any one of embodiments 1, 2, 39 or 49-53 or the bolus according to any of embodiments 1-38, wherein the core of the delayed release dosage form or the bolus comprises one or more metal particles (preferably steel particles), wherein the particles are preferably rounded and wherein the total of all particles per bolus or per delayed release dosage form has a mass of at least 100 grams.

Embodiment 55 provides the delayed release dosage form or the bolus according to embodiment 54, wherein the particles are granules and/or spheres.

Embodiment 56 provides the delayed release dosage form according to any one of embodiments 49-55, wherein the wax is paraffin and/or carnauba and/or castor wax.

Embodiment 57 provides the delayed release dosage form according to any one of embodiments 49-56, wherein the core comprises between 30 wt % and 75 wt % haloform, preferably bromoform.

Embodiments 58 provides the delayed release dosage form according to any one of embodiments 49-57, wherein the thickness of the coating/housing is less than 2 mm.

Embodiment 59 provides the delayed release dosage form of any one of embodiments 49-58, wherein the delayed release dosage form has the shape of a bolus.

What we claim is:

1. A bolus, comprising:
   a core comprising:
      metal;
      a carrier; and
      bromoform mixed with the carrier; and
   a housing,
   wherein:
      one of the following holds:
         the housing comprises poly lactic acid (PLA) and polybutylene adipate terephthalate (PBAT); or
         the housing comprises poly lactic acid (PLA) and polybutylene succinate (PBS);
      the bolus is configured to be administered to a ruminant animal; and
      the bolus is configured so that, when the bolus is present in the rumen of the ruminant animal, bromoform passes through the housing and an effective amount of bromoform is delivered to the rumen of the ruminant animal over a period of time.

2. The bolus according to claim 1, wherein the carrier and bromoform have a relatively higher affinity for each other compared to an affinity of the housing and bromoform for each other.

3. The bolus according to claim 1, wherein the core comprises between 30 wt % to 80 wt % bromoform.

4. The bolus according to claim 1, wherein the core comprises between 30 wt % and 70 wt % bromoform.

5. The bolus according to claim 1, wherein the carrier comprises a polar substance.

6. The bolus according to claim 1, wherein the carrier comprises at least one member selected from the group consisting of myristic acid, stearic acid, steryl alcohol, cetyl alcohol, cetosteryl alcohol, a wax, PEG4000, Carnauba, Candellila, Jojoba, and Lanolin.

7. The bolus according to claim 1, wherein the carrier comprises beeswax, paraffin wax and/or castor wax.

8. The bolus according to claim 1, wherein the carrier comprises paraffin wax and castor wax in a weight ratio of castor wax to paraffin wax of between 40:60 to 60:40.

9. The bolus according to claim 1, wherein the housing comprises a cavity in which at least a portion of the core is located, and/or the housing has an open end.

10. The bolus according to claim 1, wherein the housing comprises a substance having a Shore D hardness of at least 40 and less than 70.

11. The bolus according to claim 1, wherein the housing comprises PLA and PBAT.

12. The bolus according to claim 11, wherein the PLA and PBAT are present in the housing with a weight ratio ranging from 70:30 to 20:80 PLA:PBAT.

13. The bolus according to claim 1, wherein the housing comprises one or more plasticisers, hardeners and/or colourants.

14. The bolus according to claim 1, wherein the housing has a thickness of below 2 mm.

15. The bolus according to claim 1, wherein the housing has a thickness in the range of 0.3-1.5 mm.

16. The bolus according to claim 1, wherein the core has a melting point greater than 37° C.

17. The bolus according to claim 1, further comprising a barrier layer between at least a portion of the housing and the core to isolate the portion of the housing and the core from contacting each other.

18. The bolus according to claim 1, wherein the bolus is configured so that, when the bolus is present in the rumen of the ruminant animal, the bromoform has a maximum release rate of approximately 0.05 g to 2 g of bromoform per day into the rumen of the ruminant animal.

19. The bolus according to claim 1, wherein the bolus is the bolus is configured so that, when the bolus is present in the rumen of the ruminant animal, the bromoform is released into the rumen of the ruminant animal over a period of at least two months.

20. The bolus of claim 1, wherein the housing comprises PLA and PBS.

21. The bolus of claim 20, wherein the PLA and PBS in the housing have a PLA:PBS weight ratio of between 20:80 to 70:30.

22. The bolus of claim 1, wherein the metal comprises steel particles.

23. The bolus of claim 22, wherein the bolus comprises at most 100 grams of the steel particles.

24. The bolus of claim 1, wherein the bolus comprises at most 100 grams of the metal.

25. The bolus of claim 1, wherein the metal comprises metal pellets.

26. The bolus of claim 25, wherein the metal pellets comprise steel pellets.

27. The bolus of claim 25, wherein the metal pellets comprise zinc pellets.

28. The bolus of claim 1, wherein the metal comprises steel.

29. The bolus of claim 1, wherein the metal comprises zinc.

30. The bolus of claim 1, wherein the metal comprises a metal rod.

31. The bolus of claim 30, wherein the metal rod comprises a steel rod.

32. The bolus of claim 30, wherein the metal rod comprises a zinc rod.

33. The bolus of claim 30, wherein the carrier comprises the metal.

34. The bolus of claim 1, wherein the metal comprises rounded metal particles.

35. The bolus of claim 34, wherein the bolus comprises at most 100 grams of the rounded metal particles.

36. The bolus of claim 35, wherein the rounded metal particles comprise rounded steel particles.

37. The bolus of claim 34, wherein the rounded metal particles comprise rounded steel particles.

38. The bolus of claim 1, wherein the housing completely covers and surrounds the core so that the housing defines a sealed cavity in which the core is located.

39. The bolus of claim 1, wherein the bolus further comprises a cap, and together the housing and the cap together define a closed and sealed cavity in which the core is located.

40. The bolus according to claim 39, wherein the housing comprises a material configured to have the bromoform migrate therethrough.

41. The bolus of claim 38, wherein the housing is completely solid.

42. The bolus of claim 41, wherein, before the bolus is present in the rumen of the ruminant animal, bromoform cannot pass through the housing.

43. The bolus of claim 39, wherein the together the housing and the cap define a completely solid article.

44. The bolus of claim 43, wherein, before the bolus is present in the rumen of the ruminant animal, bromoform cannot pass through the housing or the cap.

45. The bolus of claim 1, one of the following holds:
   the housing completely covers and surrounds the core so that the housing defines a sealed cavity in which the core is located; or
   the bolus further comprises a cap, and together the housing and the cap define a closed and sealed cavity in which the core is located.

46. The bolus of claim 1, wherein the carrier comprises wax.

* * * * *

UNITED STATES PATENT AND TRADEMARK OFFICE
CERTIFICATE OF CORRECTION

| | |
|---|---|
| PATENT NO. | : 12,171,873 B2 |
| APPLICATION NO. | : 17/987983 |
| DATED | : December 24, 2024 |
| INVENTOR(S) | : Mark Christopher Lay et al. |

Page 1 of 3

It is certified that error appears in the above-identified patent and that said Letters Patent is hereby corrected as shown below:

On the Title Page

Column 2 (item (56) Other Publications), Line 1, after "Ecol" insert -- . --.

Page 6, Column 1 (item (56) Other Publications), Line 57, delete "POly" and insert -- Poly --.

In the Drawings

Sheet 15 of 21, Figure 16B, Line 1 (Y-axis), delete "absrobed" and insert -- absorbed --.

Sheet 20 of 21, Figure 18A, Line 1 (Y-axis), delete "bromofrom" and insert -- Bromoform --.

In the Specification

Column 4, Line 51, delete "steryl" and insert -- stearyl --.

Column 4, Line 52, delete "cetosteryl" and insert -- cetostearyl --.

Column 4, Line 56, delete "Candellila," and insert -- Candelilla, --.

Column 7, Lines 18-20, delete "In these embodiments, a relatively thicker housing will have a relatively slower release rate than a relatively thinner housing." and insert the same on Column 7, Line 17 (Approx.), as a continuation of the same paragraph.

Column 7, Line 49, delete "across-" and insert -- cross- --.

Column 8, Line 26, delete "made be" and insert -- may be --.

Column 8, Line 62, delete "0,4" and insert -- 0.4 --.

Signed and Sealed this
Thirteenth Day of May, 2025

Coke Morgan Stewart
*Acting Director of the United States Patent and Trademark Office*

Column 9, Line 14, delete "silicons," and insert -- silicones, --.

Column 10, Line 64, delete "0,4" and insert -- 0.4 --.

Column 11, Line 13, delete "0,4" and insert -- 0.4 --.

Column 11, Lines 59-65, delete "In a further aspect, the invention provides a delayed release dosage form for administration to a ruminant animal, wherein said delayed release dosage form comprises: a core, wherein the core comprises a haloform (preferably bromoform); and a coating which covers at least a portion of the core or preferably the entire core; wherein the delayed release dosage form is configured to release the haloform." and insert the same on Column 11, Line 58, as a continuation of the same paragraph.

Column 12, Line 31, delete "0,4" and insert -- 0.4 --.

Column 12, Line 47, delete "0,4" and insert -- 0.4 --.

Column 13, Line 55, delete "agent (s)" and insert -- agent(s) --.

Column 14, Line 14, delete "Candellila," and insert -- Candelilla, --.

Column 17, Line 26, delete "Candellila," and insert -- Candelilla --.

Column 17, Line 30, delete "a" and insert -- as --.

Column 20, Line 14, delete "intake." and insert -- intake --.

Column 21, Line 47, delete "FIG." and insert -- FIGS. --.

Column 21, Line 61, after "(200)" insert -- . --.

Column 24, Line 12, delete "826—which" and insert -- 826 which --.

Columns 27-28 (Table 2), Line 2, delete "Espected" and insert -- Expected --.

Columns 27-28 (Table 2), Line 4, delete "Tickness" and insert -- Thickness --.

Columns 27-28 (Table 2), Line 8, delete "1.999" and insert -- 1.939 --.

Columns 27-28 (Table 2), Line 9, delete "3.5" and insert -- 3.6 --.

Columns 27-28 (Table 2), Line 9, delete "0.085" and insert -- 0.086 --.

Column 29, Line 60, delete "Bromofrom" and insert -- Bromoform --.

Columns 31-32 (Table 5), Line 15, delete "8" and insert -- 6 --.

CERTIFICATE OF CORRECTION (continued)
U.S. Pat. No. 12,171,873 B2

Columns 31-32 (Table 5), Line 24, delete "administred" and insert -- administered --.

Column 33, Line 18, delete "~2.8-min" and insert -- ~2.8 min --.

Column 33, Line 21, delete "in-" and insert -- in --.

Column 33, Line 22, delete "-Patiio" and insert -- -Patiño --.

Column 34 (Table 7), Line 1, delete "(CH4)" and insert -- (CH$_4$) --.

Column 34 (Table 7), Line 1, delete "(H2)" and insert -- (H$_2$) --.

Column 34, Line 37, delete "that that" and insert -- that --.

Column 34, Line 66, delete "Labcono" and insert -- Labconco --.

Column 36, Line 33, delete "PANalytica" and insert -- Panalytical --.

Column 36, Line 64, delete "2theta." and insert -- 2Theta. --.

Column 38, Line 61, delete "steryl" and insert -- stearyl --.

Column 38, Line 62, delete "cetosteryl" and insert -- cetostearyl --.

Column 38, Line 63, delete "Candellila," and insert -- Candelilla, --.

Column 39, Lines 43-44, delete "Polybutylenadipat-terephthalat" and insert -- Polybutylene adipate terephthalate --.

Column 39, Line 48, delete "Polybutylenadipat-terephthalat" and insert -- Polybutylene adipate terephthalate --.

Column 39, Line 50, "Polybutylenadipat-terephthalat (PBAT)ratio" and insert -- Polybutylene adipate terephthalate (PBAT) ratio --.

In the Claims

Column 42, Line 7, Claim 6, delete "steryl" and insert -- stearyl --.

Column 42, Line 8, Claim 6, delete "cetosteryl" and insert -- cetostearyl --.

Column 42, Line 9, Claim 6, delete "Candellila," and insert -- Candelilla, --.

Column 42, Lines 44-45, Claim 19, delete "the bolus is the bolus is" and insert -- the bolus is --.